(12) United States Patent
Cianci et al.

(10) Patent No.: US 8,362,004 B2
(45) Date of Patent: Jan. 29, 2013

(54) PIPERAZINE ANALOGS AS BROAD-SPECTRUM INFLUENZA ANTIVIRALS

(75) Inventors: Christopher W. Cianci, Madison, CT (US); Samuel Gerritz, Guilford, CT (US); Guo Li, Wallingford, CT (US); Bradley C. Pearce, East Hampton, CT (US); Annapurna Pendri, South Glastonbury, CT (US); Shuhao Shi, Madison, CT (US); Weixu Zhai, Middletown, CT (US); Shirong Zhu, Cheshire, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/225,851

(22) Filed: Sep. 6, 2011

(65) Prior Publication Data
US 2012/0238539 A1 Sep. 20, 2012

Related U.S. Application Data

(60) Provisional application No. 61/380,728, filed on Sep. 8, 2010.

(51) Int. Cl.
| A61K 31/397 | (2006.01) |
| A61K 31/496 | (2006.01) |
| C07D 403/04 | (2006.01) |
| C07D 403/14 | (2006.01) |
| C07D 413/04 | (2006.01) |
| C07D 413/14 | (2006.01) |

(52) U.S. Cl. ........... 514/210.2; 514/254.01; 514/254.04; 514/254.05; 544/359; 544/367; 544/372

(58) Field of Classification Search ............. 514/210.2, 514/254.01, 254.04, 254.05; 544/359, 367, 544/372
See application file for complete search history.

(56) References Cited

FOREIGN PATENT DOCUMENTS
| EP | 1 396 487 | 3/2004 |
| WO | WO 01/02388 | 1/2001 |
| WO | WO 2004/078732 | 9/2004 |
| WO | WO 2007/104558 | 9/2007 |
| WO | WO 2011/015037 | 2/2011 |

OTHER PUBLICATIONS

Chen, J. et al., "Influenza virus antigenic variation, host antibody production and new approach to control epidemics", Virology Journal, vol. 6, No. 30 (2009), doi:10.1186/1743-422X-6-30.
Deyde, V.M. et al., "Detection of Molecular Markers of Drug Resistance in 2009 Pandemic Influenza A (H1N1) Viruses by Pyrosequencing", Antimicrobial Agents and Chemotherapy, vol. 54, No. 3, pp. 1102-1110 (2010).
Moscona, A., "Global Transmission of Oseltamivir-Resistant Influenza", The New England Journal of Medicine, vol. 360, No. 10, pp. 953-956 (2009).
Soepandi, P.Z. et al., "Clinical Course of Avian Influenza A(H5N1) in Patients at the Persahabatan Hospital, Jakarta, Indonesia, 2005-2008", Chest, vol. 138, No. 3, pp. 665-673 (2010).
Zimmer, S.M. et al., "Historical Perspective—Emergence of Influenza A (H1N1) Viruses", The New England Journal of Medicine, vol. 361, No. 3, pp. 279-285 (2009).

*Primary Examiner* — Rebecca Anderson
*Assistant Examiner* — Samantha Shterengarts
(74) *Attorney, Agent, or Firm* — John F. Levis

(57) ABSTRACT

A compound of Formula I is set forth, including pharmaceutically acceptable salts thereof:

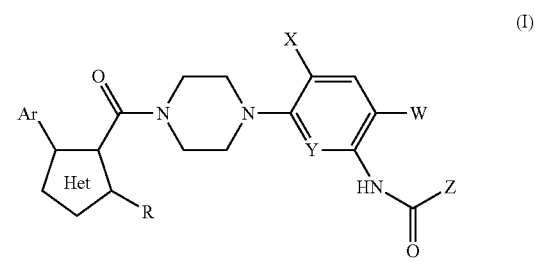

(I)

wherein Het is a 5 or 6-membered heterocycle with —N, —O, or —S adjacent to the —Ar substituent or adjacent to the point of attachment for the —Ar substituent;
Ar is aryl or heteroaryl;
R is —$CH_3$, —$CH_2F$, or —$CH=CH_2$;
W is —$NO_2$, —Cl, —Br, —CHO, —$CH=CH_2$, or —CN;
X is —Cl, —$CH_3$, or —CN;
Y is —CH or —N; and
Z is $C_1$-$C_6$ alkyl, $C_3$-$C_6$ cycloalkyl, substituted aryl, substituted heteroaryl, $OR^1$, or $NHR^1$, wherein $R^1$ is selected from the group of H, aryl, heteroaryl, $C_1$-$C_6$ alkyl and $C_3$-$C_6$ cycloalkyl.
This compound is useful in compositions for the prevention and treatment of influenza virus.

28 Claims, No Drawings

PIPERAZINE ANALOGS AS BROAD-SPECTRUM INFLUENZA ANTIVIRALS

CROSS REFERENCE TO RELATED APPLICATION

This non-provisional application claims the benefit of U.S. Provisional Application Ser. No. 61/380,728 filed Sep. 8, 2010.

FIELD OF THE INVENTION

The present invention relates to novel compounds useful for the prophylaxis and treatment of influenza virus, and to compositions and formulations containing these compounds. The invention also relates to methods for preventing and treating influenza infection utilizing the compounds herein set forth.

BACKGROUND OF THE INVENTION

Influenza virus is a significant causative agent of acute lower respiratory tract infections in humans. It transmits readily, resulting in annual epidemics that can manifest in severe illness and death for high-risk populations. It is one of the RNA viruses of the family Orthomyxoviridae that affects birds and mammals, and is responsible for the illness commonly referred to as the "flu". The most common symptoms of the flu are chills, fever, sore throat, muscle pains, severe headache, coughing, weakness/fatigue and general discomfort. Sore throat, fever and coughs are the most frequent symptoms. In more serious cases, influenza causes pneumonia, which can be fatal, particularly for the young and the elderly. Although it is often confused with other influenza-like illnesses, especially the common cold, influenza is a more severe disease than the common cold and is caused by a different type of virus. Influenza may produce nausea and vomiting, particularly in children, but these symptoms are more common in the unrelated gastroenteritis, which is sometimes called "stomach flu" or "24-hour flu".

Typically, the influenza virus is transmitted through the air by coughs or sneezes, creating aerosols containing the virus. Influenza can also be transmitted by direct contact with bird droppings or nasal secretions, or through contact with contaminated surfaces. Airborne aerosols have been thought to cause most infections, although which means of transmission is most important is not absolutely clear.

Influenza remains a constant threat, as new variants emerge seasonally. Annual epidemics take an economic toll through lost workforce productivity, while straining health service resources. Additionally, influenza virus is responsible for major pandemics every 10-50 years. In 2009, a new H1N1 triple re-assortment of swine influenza emerged in North America and reached pandemic proportion (Zimmer and Burke, 2009). Influenza virus' ability to mutate (antigenic drift), as well as re-assort with other influenza viruses from different mammalian species (antigenic shift), are mechanisms causing seasonal epidemic variation and pandemic virus insurgence, respectively (Chen and Deng, 2009). Moreover, resistance to available anti-influenza agents is increasing. The majority of H3N2 isolates and 2009 H1N1 are resistant to the adamantane M2 ion channel inhibitors (Deyde et al, 2009). Furthermore, 2008 H1N1 has shown resistantance to the neuraminidase inhibitor Tamiflu (Oseltamivir), the standard of care (Moscona, 2009). Neither class has been shown to be effective against highly pathogenic H5N1 avian virus (Soepandi, 2010).

Multiple novel therapeutic and prophylactic agents against influenza virus are therefore currently needed in the art. Also needed are new compositions and formulations containing these agents, as well as new methods for preventing and treating influenza utilizing these agents.

SUMMARY OF THE INVENTION

The invention, in a first embodiment, provides a compound of Formula I, including pharmaceutically acceptable salts thereof:

(I)

wherein Het is a 5 or 6-membered heterocycle with —N, —O, or —S adjacent to the —Ar substituent or adjacent to the point of attachment for the —Ar substituent;

Ar is aryl or heteroaryl;

R is $—CH_3$, $—CH_2F$, or $—CH{=}CH_2$;

W is $—NO_2$, —Cl, —Br, —CHO, $—CH{=}CH_2$, or —CN;

X is —Cl, $—CH_3$, or —CN;

Y is —CH or —N; and

Z is $C_1$-$C_6$ alkyl, $C_3$-$C_6$ cycloalkyl, substituted aryl, substituted heteroaryl, $OR^1$, or $NHR^1$, wherein $R^1$ is selected from the group of H, aryl, heteroaryl, $C_1$-$C_6$ alkyl and $C_3$-$C_6$ cycloalkyl.

Also provided as part of the invention is a pharmaceutical composition which comprises an antiviral effective amount of one or more of the compounds of Formula I, including pharmaceutically acceptable salts thereof, together with one or more pharmaceutically acceptable carriers, excipients or diluents.

In addition, there is provided a method for treating a mammal infected with influenza virus comprising administering to said mammal an antiviral effective amount of a compound of Formula I including pharmaceutically acceptable salts thereof, and one or more pharmaceutically acceptable carriers, excipients or diluents.

Methods for making the compounds of Formula I are also herein provided.

The invention is directed to these and other important ends, hereinafter described.

DETAILED DESCRIPTION OF THE EMBODIMENTS

Since the compounds of the present invention may possess asymmetric centers and therefore occur as mixtures of diastereomers and enantiomers, the present invention includes the individual diastereoisomeric and enantiomeric forms of the compounds of Formula I in addition to the mixtures thereof.

DEFINITIONS

Unless otherwise specifically set forth elsewhere in the application, one or more of the following terms may be used herein, and shall have the following meanings:

The term "$C_{1-6}$ alkyl" as used herein means straight or branched chain alkyl groups such as methyl, ethyl, propyl, isopropyl, butyl, isobutyl, t-butyl, amyl, hexyl and the like.

"Halogen" refers to chlorine, bromine, iodine or fluorine.

"H" or "Hydrogen" refers to hydrogen, including its isotopes such as deuterium.

An "aryl" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthracenyl. The aryl group may be substituted or unsubstituted. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —$NR^xR^y$, wherein $R^x$ and $R^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl. diazinyl, pyrazine, triazinyl, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thioalkoxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —$NR^xR^y$, wherein $R^x$ and $R^y$ are as defined above.

As used herein, a "heteroalicyclic" group refers to a monocyclic or fused ring group having in the ring(s) one or more atoms selected from the group consisting of nitrogen, oxygen and sulfur. Rings are selected from those which provide stable arrangements of bonds and are not intended to encompass systems which would not exist. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —$NR^xR^y$, wherein $R^x$ and $R^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalo-methanesulfonamido, trihalomethanesulfonyl, silyl, guanyl, guanidino, ureido, phosphonyl, amino and —$NR^xR^y$ with $R^x$ and $R^y$ as defined above.

An "alkenyl" group refers to an alkyl group, as defined herein, having at least two carbon atoms and at least one carbon-carbon double bond.

An "alkynyl" group refers to an alkyl group, as defined herein, having at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "Keto" group refers to a —CC(=O)C— group wherein the carbon on either or both sides of the C=O may be alkyl, cycloalkyl, aryl or a carbon of a heteroaryl or heteroalicyclic group.

A "trihalomethanecarbonyl" group refers to a $Z_3CC(=O)$— group with said Z being a halogen.

A "C-carboxy" group refers to a —C(=O)O—R" groups, with R" as defined herein.

An "O-carboxy" group refers to a R"C(=O)O-group, with R" as defined herein.

A "carboxylic acid" group refers to a C-carboxy group in which R" is hydrogen.

A "trihalomethyl" group refers to a —$CZ_3$, group wherein Z is a halogen group as defined herein.

A "trihalomethanesulfonyl" group refers to an $Z_3CS(=O)_2$— groups with Z as defined above.

A "trihalomethanesulfonamido" group refers to a $Z_3CS(=O)_2NR^x$— group with Z as defined above and $R^x$ being H or $(C_{1-6})$alkyl.

A "sulfinyl" group refers to a —S(=O)—R" group, with R" being $(C_{1-6})$alkyl.

A "sulfonyl" group refers to a —$S(=O)_2R$" group with R" being $(C_{1-6})$alkyl.

A "S-sulfonamido" group refers to a —$S(=O)_2NR^XR^Y$, with $R^X$ and $R^Y$ independently being H or $(C_{1-6})$alkyl.

A "N-Sulfonamido" group refers to a $R"S(=O)_2NR^x$— group, with Rx being H or $(C_{1-6})$alkyl;

A "O-carbamyl" group refers to a —OC(=O)$NR^xR^y$ group, with $R^X$ and $R^Y$ independently being H or $(C_{1-6})$alkyl.

A "N-carbamyl" group refers to a $R^xOC(=O)NR^y$ group, with Rx and $R^y$ independently being H or $(C_{1-6})$alkyl.

A "O-thiocarbamyl" group refers to a —OC(=S)$NR^xR^y$ group, with $R^x$ and $R^y$ independently being H or $(C_{1-6})$alkyl.

A "N-thiocarbamyl" group refers to a $R^xOC(=S)NR^y$— group, with $R^x$ and $R^y$ independently being H or $(C_{1-6})$alkyl.

An "amino" group refers to an —$NH_2$ group.

An "amido" group refers to a univalent radical —$NH_2$ when attached via a carboxyl group.

A "C-amido" group refers to a —C(=O)$NR^xR^y$ group, with $R^x$ and $R^y$ independently being H or $(C_{1-6})$alkyl.

A "C-thioamido" group refers to a —C(=S)$NR^xR^y$ group, with $R^x$ and $R^y$ independently being H or $(C_{1-6})$alkyl.

A "N-amido" group refers to a $R^xC(=O)NR^y$— group, with $R^x$ and $R^y$ independently being H or $(C_{1-6})$alkyl.

An "ureido" group refers to a NR" (=O)$NR^yR^{y2}$ group, with $R^x$, $R^y$, and $R^{y2}$ independently being H or $(C_{1-6})$alkyl.

A "guanidino" group refers to a —$R^xNC(=N)NR^yR^{y2}$ group, with $R^x$, $R^y$, and $R^{y2}$ independently being H or $(C_{1-6})$alkyl.

A "guanyl" group refers to a $R^xR^yNC(=N)$— group, with $R^x$ and $R^y$ independently being H or $(C_{1-6})$alkyl.

A "cyano" group refers to a —CN group.

A "silyl" group refers to a —$Si(R")_3$, with R" being $(C_{1-6})$ alkyl or phenyl.

A "phosphonyl" group refers to a $P(=O)(OR^x)_2$ with Rx being $(C_{1-6})$alkyl.

A "hydrazino" group refers to a —$NR^xNR^yR^{y2}$ group, with $R^x$, $R^y$, and $R^{y2}$ independently being H or $(C_{1-6})$alkyl.

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present disclosure are based on the known general principles of chemical bonding. It is understood that the claims do not encompass structures known to be unstable or not able to exist based on the literature.

Physiologically acceptable salts and prodrugs of compounds disclosed herein are within the scope of this disclosure. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris (hydroxymethyl)-aminomethane), or with bases such as piperidine or morpholine.

As set forth above, the present invention is directed to compounds of Formula I, including pharmaceutically acceptable salts thereof:

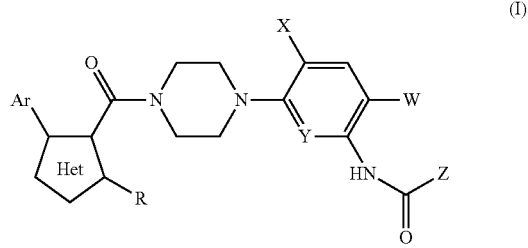

(I)

wherein Het is a 5 or 6-membered heterocycle with —N, —O, or —S adjacent to the —Ar substituent or adjacent to the point of attachment for the —Ar substituent;

Ar is aryl or heteroaryl;

R is —$CH_3$, —$CH_2F$, or —CH=$CH_2$;

W is —$NO_2$, —Cl, —Br, —CHO, —CH=$CH_2$, or —CN;

X is —Cl, —$CH_3$, or —CN;

Y is —CH or —N; and

Z is $C_1$-$C_6$ alkyl, $C_3$-$C_6$ cycloalkyl, substituted aryl, substituted heteroaryl, $OR^1$, or $NHR^1$, wherein $R^1$ is selected from the group of H, aryl, heteroaryl, $C_1$-$C_6$ alkyl and $C_3$-$C_6$ cycloalkyl.

In a preferred embodiment of the invention, the substituent Het is selected from the group of:

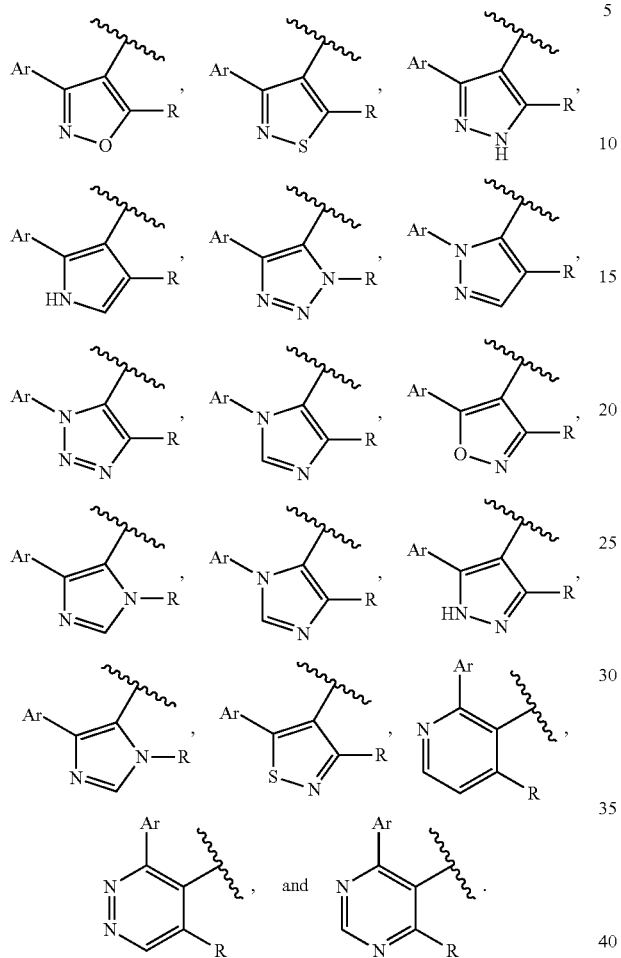

In particular, it is preferred that Het is a 5 or 6-membered heterocycle with —N adjacent to the point of attachment for the —Ar component. Even more preferably, Het is selected from the group of:

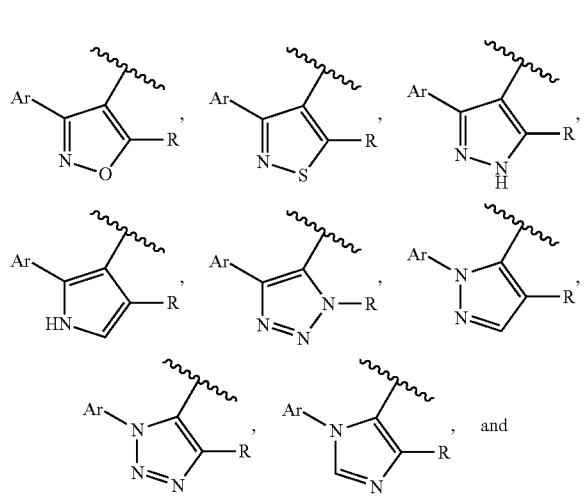

-continued

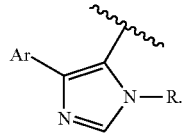

Of the foregoing, the Het substituents

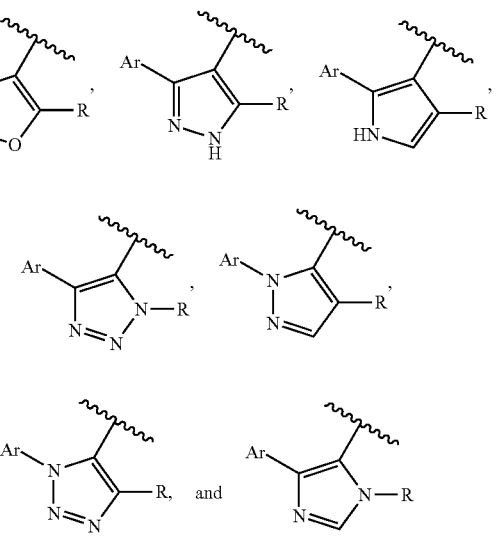

are particularly preferred.

In a further embodiment of the compounds of Formula I, it is preferred that Ar is selected from the group of:

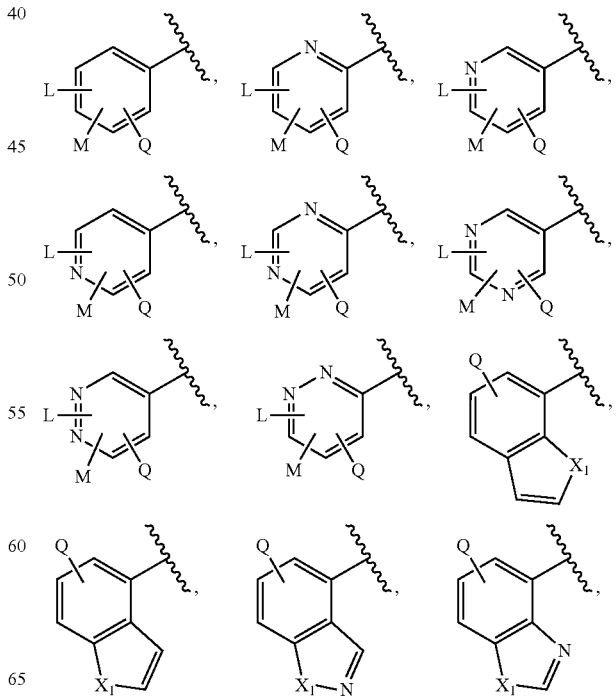

-continued

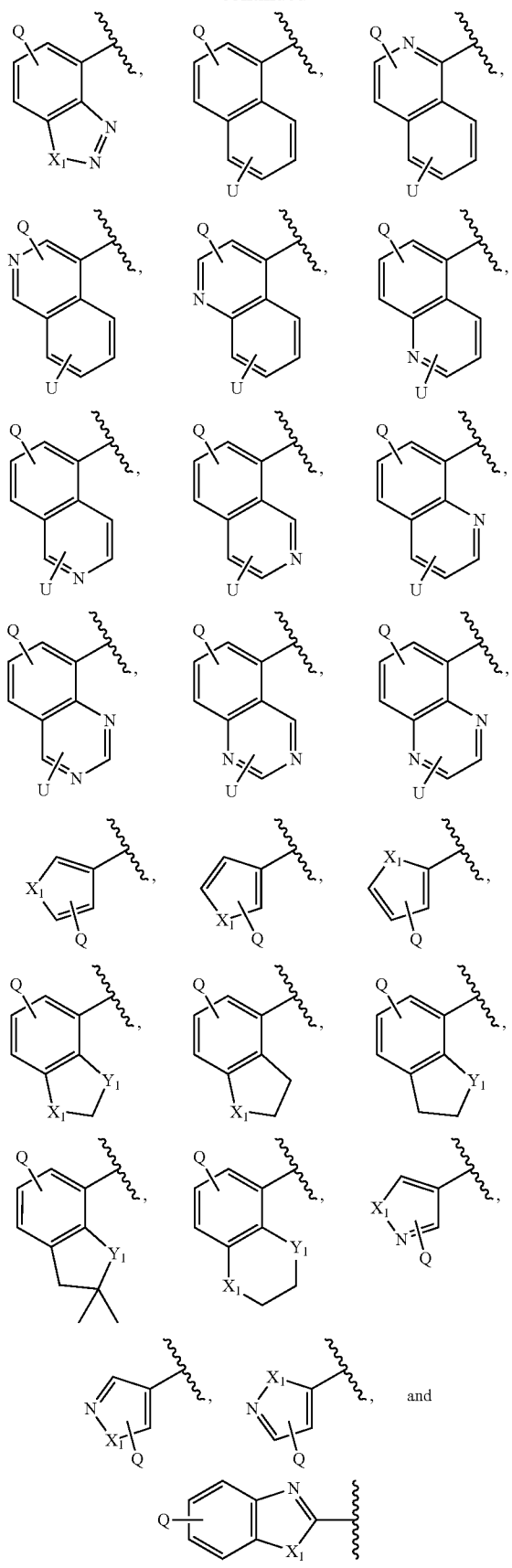

wherein
L is H, halogen, cyano, hydroxyl, amino, alkyl, alkoxy, alkylamino, or amido;
M is H, halogen, cyano, hydroxyl, amino, alkyl, alkoxy, alkylamino, or amido;
Q is H, halogen, cyano, hydroxyl, amino, alkyl, alkoxy, alkylamino, or amido;
U is H, halogen, cyano, hydroxyl, amino, alkyl, alkoxy, alkylamino, or amido;
$X_1$ is O, NH, N-alkyl, N-aryl, S or $CH_2$; and
$Y_1$ is O, NH, N-alkyl, N-aryl, S or $CH_2$.

Even more preferably, the Ar substituent is selected from the group of:

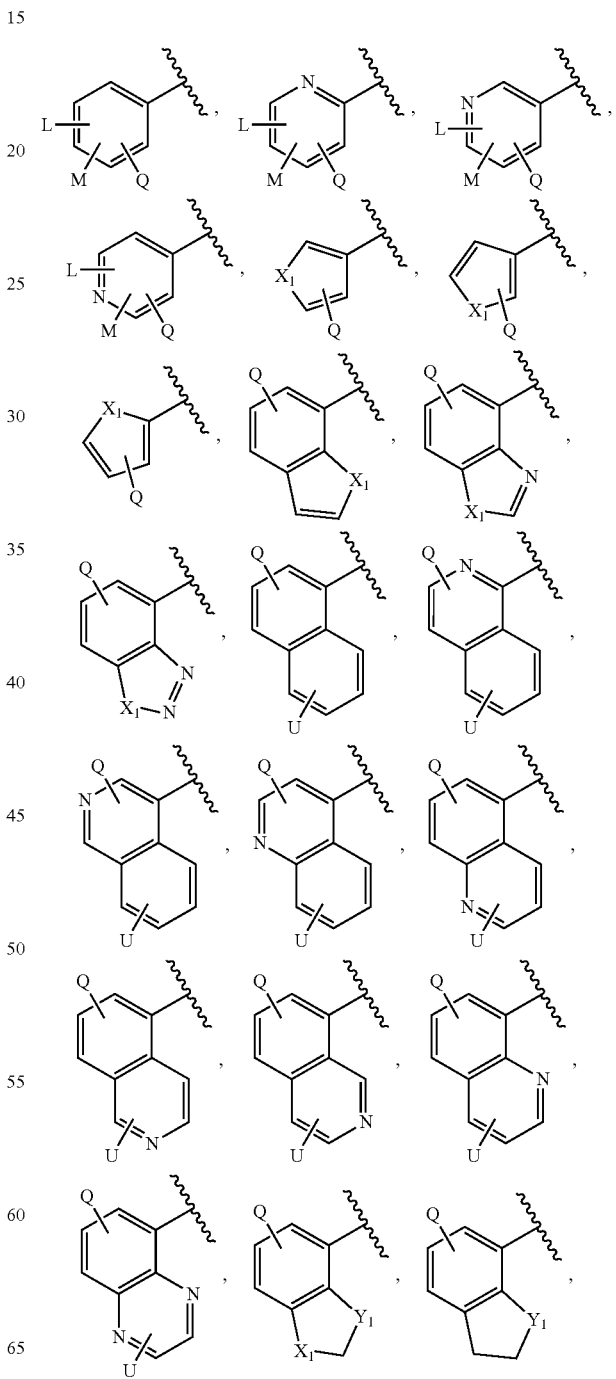

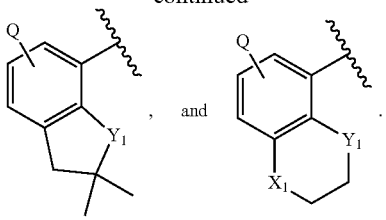

It is even more preferred that Ar be selected from the group of:

It is especially preferred that Ar be a phenyl group, or phenyl which is substituted with methoxy or hydroxyl.

As set forth above, the substituent R is —$CH_3$, —$CH_2F$, or —CH=$CH_2$. Preferably, R is —$CH_3$ or —$CH_2F$. Even more preferably, R is —$CH_3$.

The substituent W is defined as being selected from the group of —$NO_2$, —Cl, —Br, —CHO, —CH=$CH_2$, and —CN. More preferably, W is —$NO_2$, —Cl, —Br, or —CN. It is especially preferred that W be —$NO_2$, —Cl, or —Br, with —$NO_2$ and —Br being even more preferred.

The substituent X is —Cl, —$CH_3$, or —CN. Even more preferably, X is —Cl or —CN, with —Cl being even more preferred.

The substituent Y can be —CH or N. In certain embodiments, it is preferred that Y be —CH. It certain other embodiments, it is preferred both that Y be —CH and that the Ar substituent be phenyl which is substituted with either methoxy or a hydroxyl group.

As defined above, the substituent Z is $C_1$-$C_6$ alkyl, $C_3$-$C_6$ cycloalkyl, substituted aryl, substituted heteroaryl, $OR^1$, or $NHR^1$, wherein $R^1$ is selected from the group of H, aryl, heteroaryl, $C_1$-$C_6$ alkyl and $C_3$-$C_6$ cycloalkyl. It is preferred that Z be substituted aryl or substituted heteroaryl which is selected from the group of:

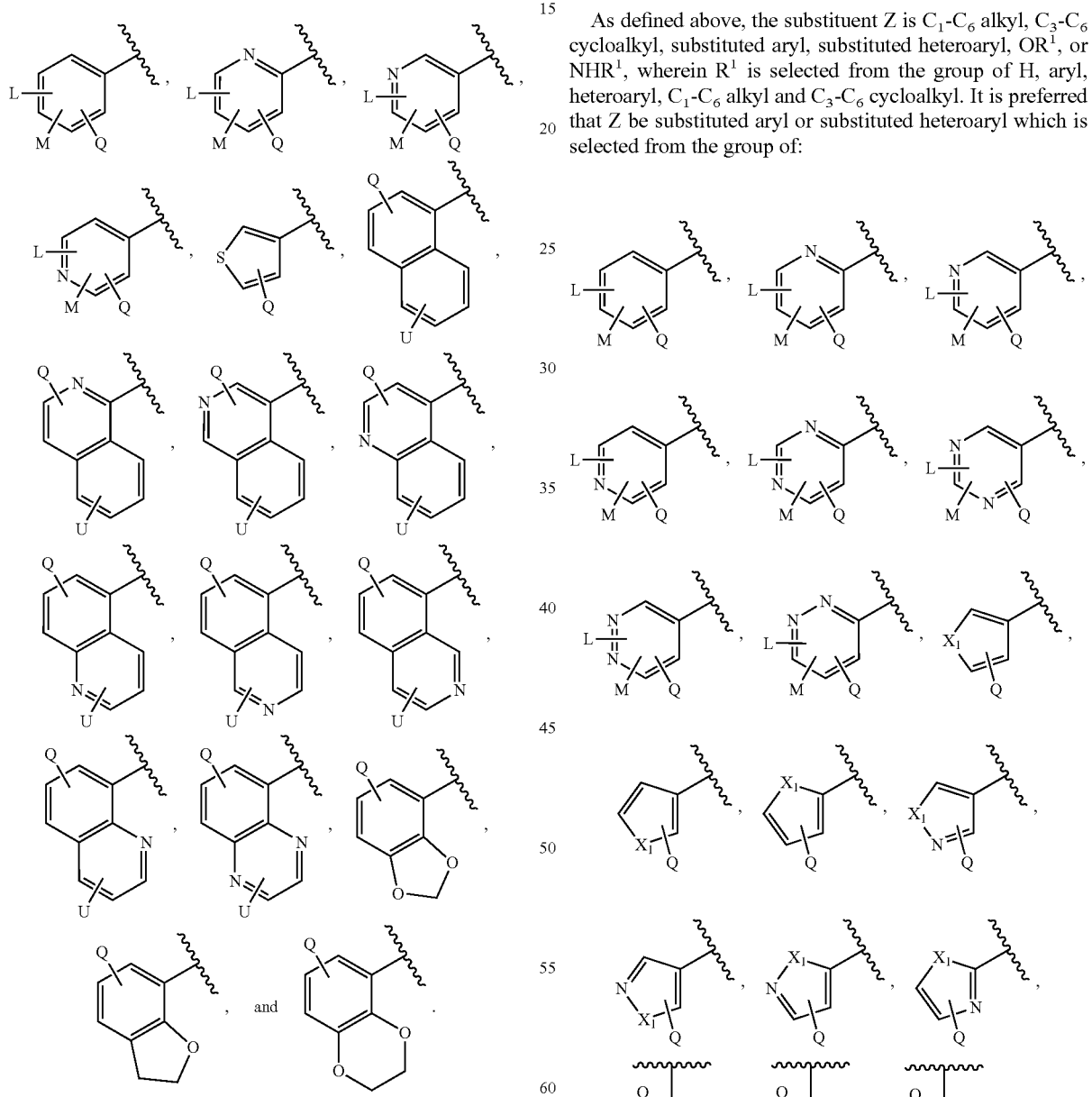

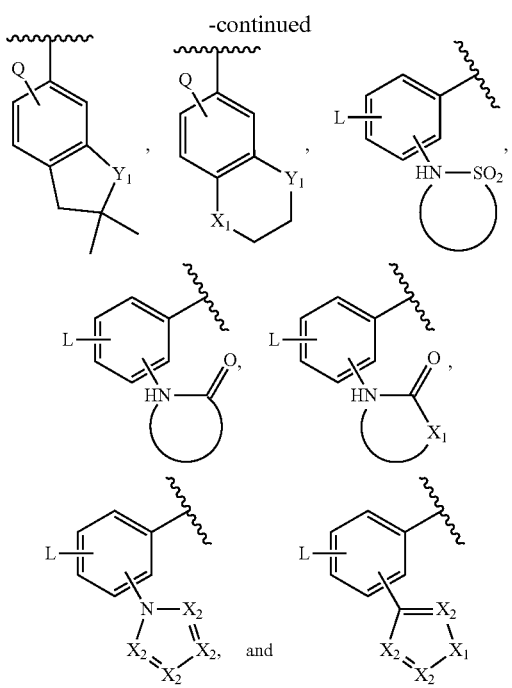

wherein
L is H, halogen, cyano, hydroxyl, amino, alkyl, alkoxy, alkylamino, or amido;
M is H, halogen, cyano, hydroxyl, amino, alkyl, alkoxy, alkylamino, or amido;
Q is H, halogen, cyano, hydroxyl, amino, alkyl, alkoxy, alkylamino, or amido;
U is H, halogen, cyano, hydroxyl, amino, alkyl, alkoxy, alkylamino, or amido;
$X_1$ is O, NH, N-alkyl, N-aryl, S or $CH_2$;
$X_2$ is N or CH; and
$Y_1$ is O, NH, N-alkyl, N-aryl, S or $CH_2$.

Even more preferably, Z is substituted phenyl. It is especially preferred that Z be phenyl which is substituted with a nitrogen-containing component. This nitrogen-containing component can be an amine group, a heteroaryl ring with at least one nitrogen, or a heterocycle with at least one nitrogen, for example.

Preferred compounds of Formula I, including pharmaceutically acceptable salts thereof, include the following:

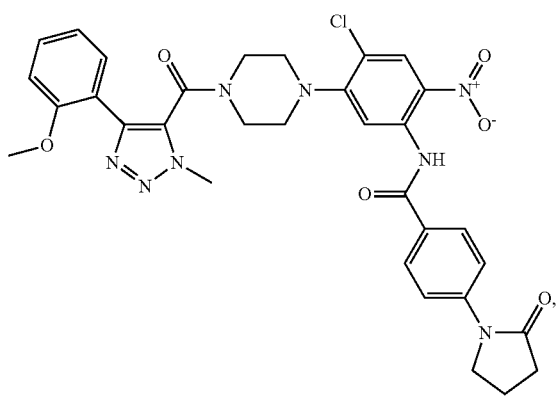

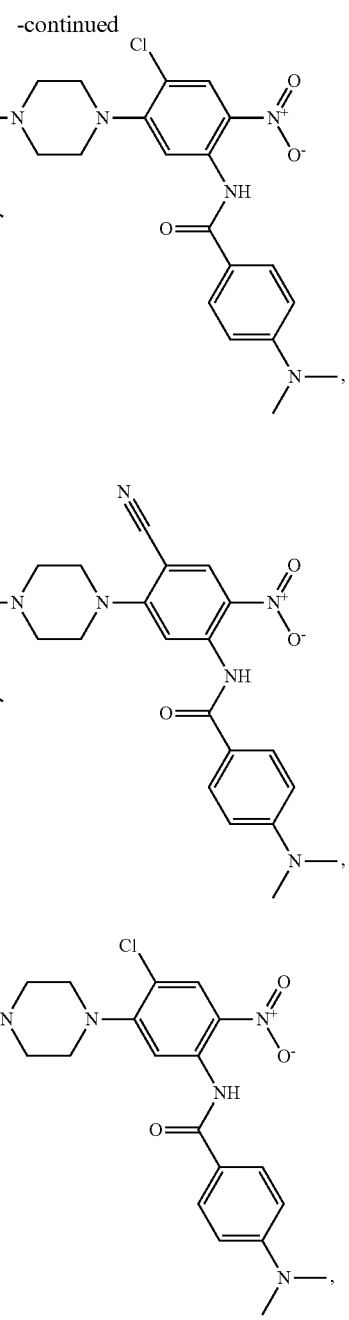

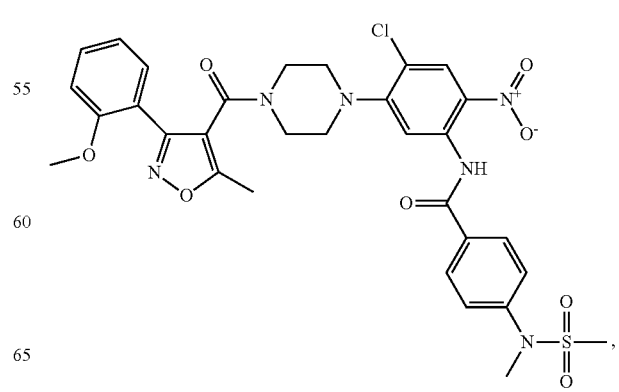

15
-continued
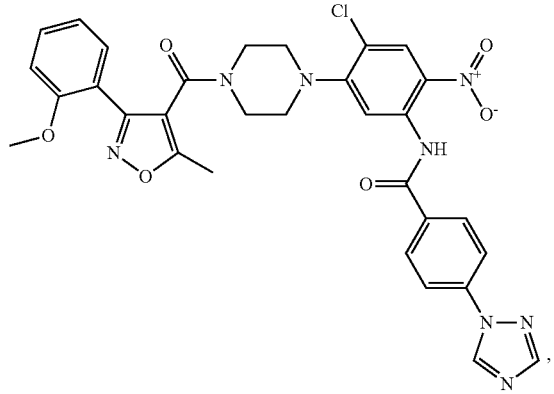
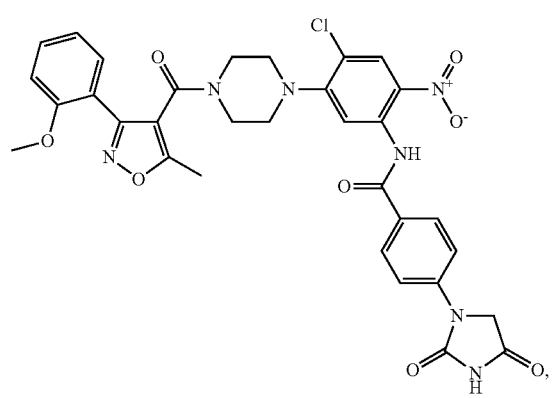
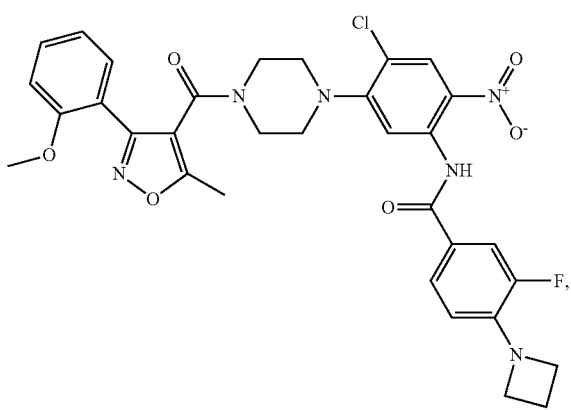
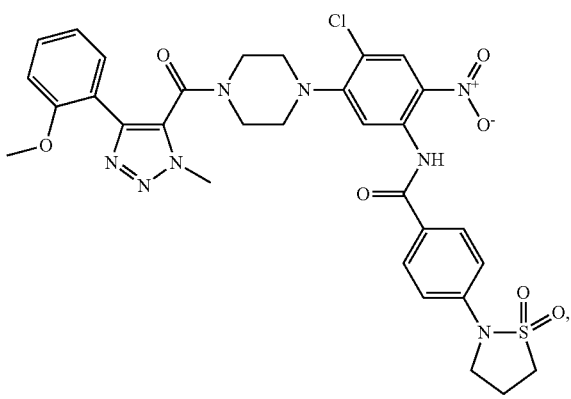
16
-continued
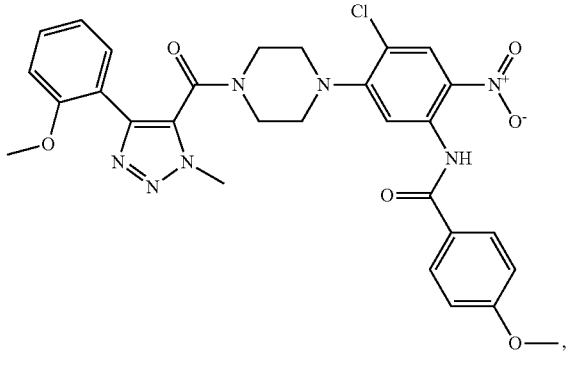
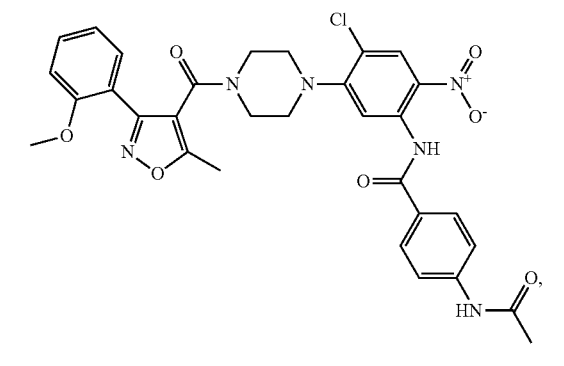
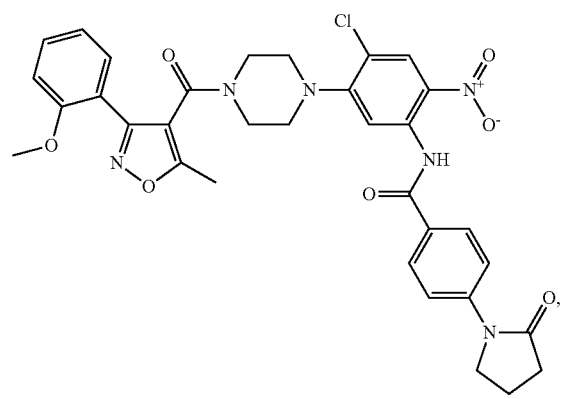

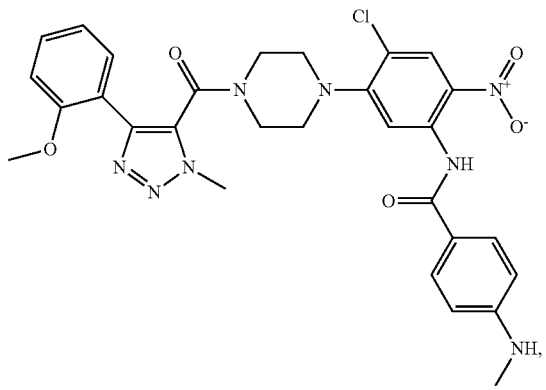

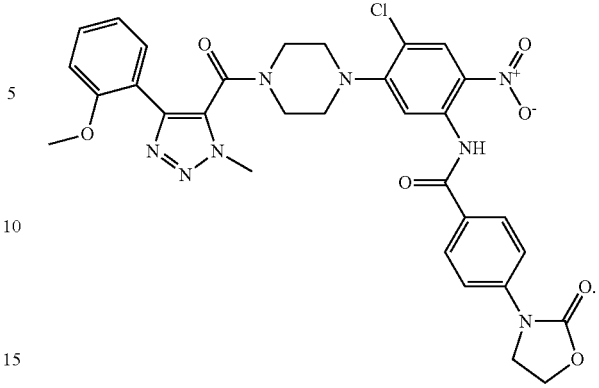

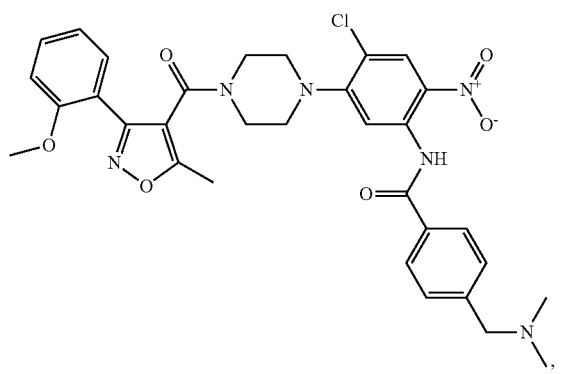

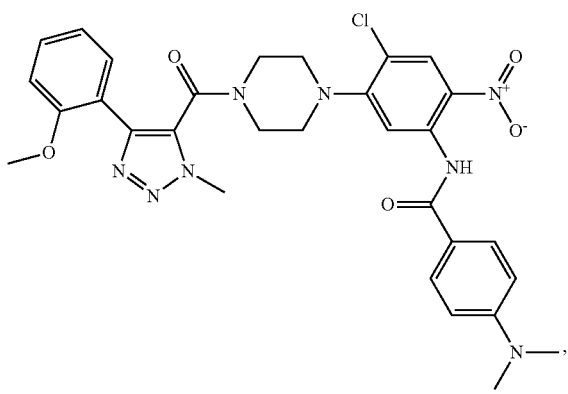

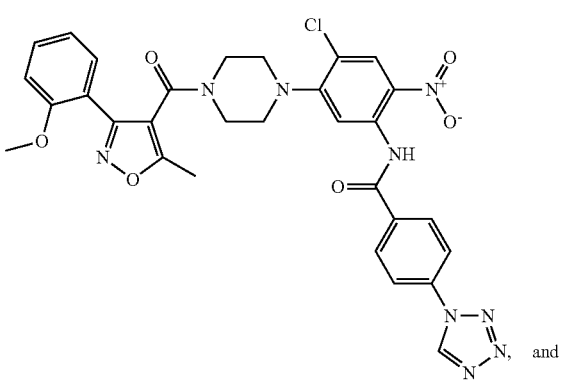

and

The compounds of the present invention may be administered orally, parenterally (including subcutaneous injections, intravenous, intramuscular, intrasternal injection or infusion techniques), by inhalation spray, or rectally or by other means available in the art, in dosage unit formulations containing conventional non-toxic pharmaceutically acceptable carriers, adjuvants and diluents.

Thus, in accordance with the present invention, there is further provided a method of treating and a pharmaceutical composition for treating viral infections such as influenza infection. The treatment involves administering to a patient in need of such treatment a pharmaceutical composition comprising a pharmaceutical carrier and a therapeutically effective amount of a compound of the present disclosure.

The pharmaceutical composition may be in the form of orally administrable suspensions or tablets; nasal sprays, sterile injectable preparations, for example, as sterile injectable aqueous or oleaginous suspensions or suppositories.

When administered orally as a suspension, these compositions are prepared according to techniques available in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds herein set forth can be administered orally to humans in a dosage range of 1 to 100 mg/kg body weight, perhaps in divided doses. One preferred dosage range is 1 to 10 mg/kg body weight orally in divided doses. Another preferred dosage range is 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In the compositions and methods of the present invention herein described, the term "antiviral effective amount" means the total amount of each active compound or component of the composition or method that is sufficient to show a meaningful patient benefit, e.g., prevention of infection by influenza or healing of acute conditions or symptoms characterized by influenza infection. The terms "treat, treating, treatment" as used herein and in the claims means preventing or ameliorating diseases and symptoms associated with influenza infection. When applied to an individual active ingredient, administered alone, the term refers to that ingredient alone. When applied to a combination, the term refers to combined amounts of the active ingredients that result in the therapeutic effect, whether administered in combination, serially or simultaneously.

The present invention is also directed to combinations of the compounds herein described with one or more other agents useful in the treatment of influenza. For example, the compounds of this invention may be effectively administered, whether at periods of pre-exposure and/or post-exposure, in combination with effective amounts of other influenza antivirals, immunomodulators, antiinfectives, or vaccines available in the art.

The following schemata are generalized procedures for making the compounds of the invention by those skilled in the art.

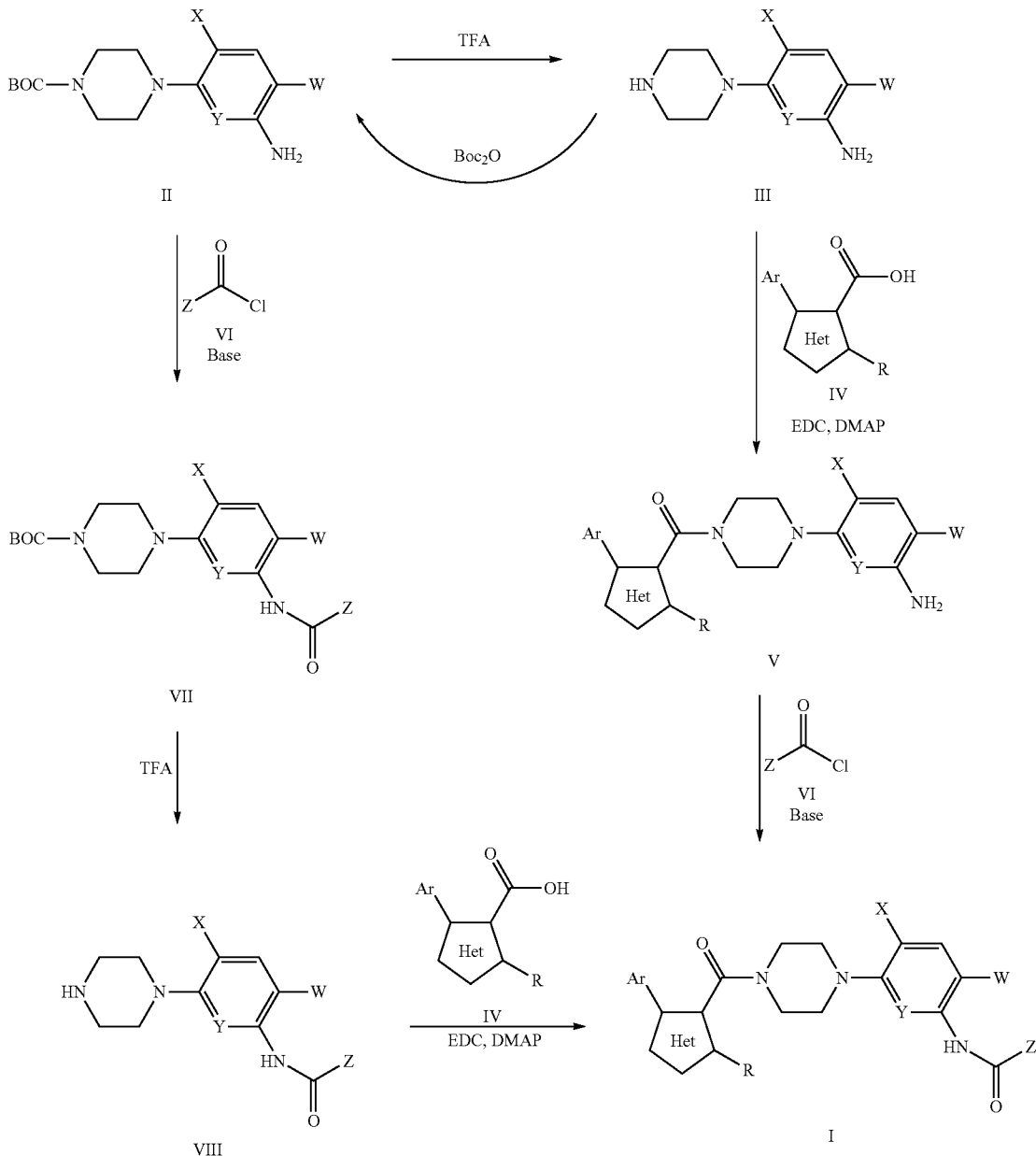

Compounds of formula I were prepared from intermediates of formula II via two complementary routes as illustrated in Scheme 1. In the first route, intermediates of formula II were treated with trifluoroacetic acid to afford intermediates of formula III. Intermediates of formula II can be obtained commercially, can be prepared by methods known in the literature, or can be readily prepared by one skilled in the art. Intermediates of formula III were treated with carboxylic acids of formula IV and an amide-bond forming reagent (i.e. EDC) to provide intermediates of formula V. Carboxylic acids of formula IV can be obtained commercially, can be prepared by methods known in the literature, or can be readily prepared by one skilled in the art. Intermediates of formula V were treated with acid chlorides of formula VI and a strong base to afford compounds of formula I. Acid chlorides of formula VI can be obtained commercially, can be prepared by methods known in the literature, or can be readily prepared by one skilled in the art. In the second route, the synthetic steps described in the first route are reversed. Intermediates of formula II were treated with acid chlorides of formula VI and a strong base to afford intermediates of formula VII. As described previously, intermediates of formula II can be obtained commercially, can be prepared by methods known in the literature, can be prepared by one skilled in the art. In addition, intermediates of formula II can be accessed via introduction of a Boc-protecting group to the piperazine nitrogen of intermediates of formula III. Acid chlorides of formula VI can be obtained commercially, can be prepared by methods known in the literature, or can be readily prepared by one skilled in the art. Intermediates of formula VII were treated with trifluoroacetic acid to afford intermediates of formula VIII. Intermediates of formula VIII were treated with carboxylic acids of formula IV and an amide-bond forming reagent (i.e. EDC) to provide compounds of formula I. Carboxylic acids of formula IV can be obtained commercially, can be prepared by methods known in the literature, or can be readily prepared by one skilled in the art.

Scheme 2

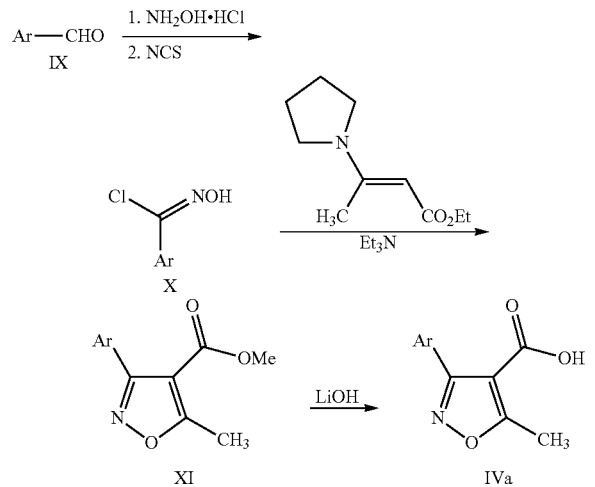

Compounds of formula IVa were prepared as outlined in Scheme 2 and as described in the literature. [See: Gerald W. Zamponi, Stephanie C. Stotz, Richard J. Staples, Tina M. Andro, Jared K. Nelson, Victoria Hulubei, Alex Blumenfeld, and Nicholas R. Natale, J. Med. Chem., 2003, 46, 87-96.] Sequential treatment of aryl aldehyde derivatives of formula IX with hydroxylamine hydrochloride, then n-chlorosuccinimide provided intermediates of formula X. Aldehyde derivatives of formula IX can be obtained commercially, can be prepared by methods known in the literature, or can be readily prepared by one skilled in the art. Intermediates of formula XI were prepared by treatment of chlorooximes of formula XII with (E)-ethyl 3-(pyrrolidin-1-yl)but-2-enoate to afford isoxazoles of formula XI. Hydrolysis of the methyl ester of isoxazoles of formula XI afforded compounds of formula IVa.

Scheme 3

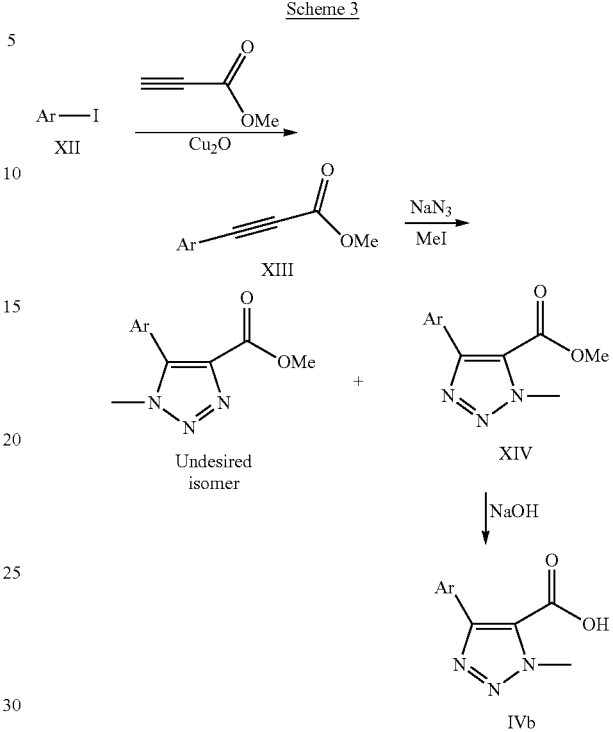

Compounds of formula IVb were prepared as outlined in Scheme 3. Aryl iodides of formula XII were coupled with methyl propiolate in the presence of copper (I) oxide [See: Liliebris, C.; Larsen, S. D; Ogg, D.; Palazuk, B. J; and Pleasdale, J. E. *J. Med. Chem.*, 2002, 45, 1785.] to provide intermediates of formula XIII. Aryl iodide derivatives of formula XII can be obtained commercially, can be prepared by methods known in the literature, or can be readily prepared by one skilled in the art. Intermediates of formula XIII were treated with sodium azide and methyl iodide to afford triazoles of formula XIV after chromatographic separation from an undesired regioisomer. Treatment of triazoles of formula XIV with sodium hydroxide provided compounds of formula IVb.

Scheme 4

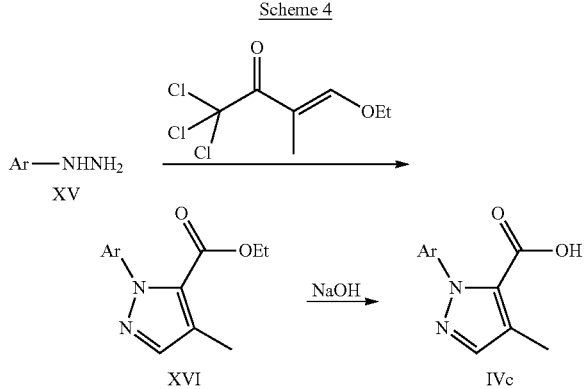

Compounds of formula IVc were prepared as outlined in Scheme 4 and as described in the literature. [See: Martins, M. A. P. et al. *J. Molecular Catalysis A: Chemical*, 2007, 266, 100.] Aryl hydrazines of formula XV were treated with (E)-

1,1,1-trichloro-4-ethoxy-3-methylbut-3-en-2-one to afford pyrazoles of formula XVI after chromatographic separation from the undesired regioisomer. Aryl hydrazines of formula XV can be obtained commercially, can be prepared by methods known in the literature, or can be readily prepared by one skilled in the art. Treatment of pyrazoles of formula XVI with sodium hydroxide provided compounds of formula IVc.

with 1,4-dioxane-2,5-diol and methylamine to afford imidazoles of formula XXII. Isocyanates of formula XXI can be obtained commercially, can be prepared by methods known in the literature, or can be readily prepared by one skilled in the art. Sequential treatment of imidazoles of formula XXII with manganese (IV) oxide and potassium permanganate afforded compounds of formula IVe.

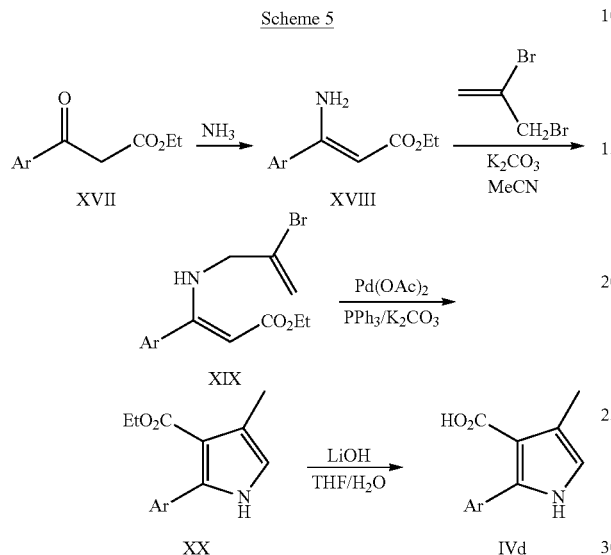

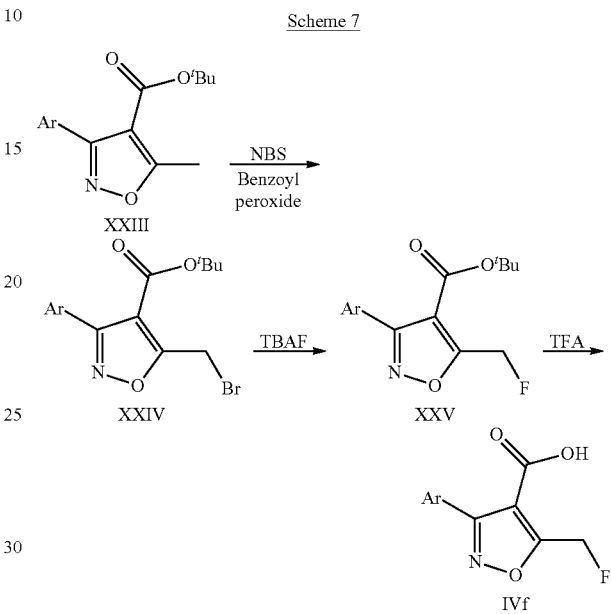

Compounds of formula IVd were prepared as outlined in Scheme 5 and as described in the literature. [See: Grigg, R.; Savic, V. Chem. Commun. 2000, (10), 873-874.] Beta-ketoesters of formula XVII were treated with ammonia to afford enamines of formula XVIII. Beta-ketoesters of formula XVII can be obtained commercially, can be prepared by methods known in the literature, or can be readily prepared by one skilled in the art. Treatment of enamines of formula XVIII with 2,3-dibromoprop-1-ene provided intermediates of formula XIX, which upon treatment with palladium(II) acetate afforded pyrroles of formula XX. Treatment of pyrroles of formula XX with lithium hydroxide provided compounds of formula IVd.

Compounds of formula IVf were prepared as outlined in Scheme 7. Isoxazoles of formula XXIII were brominated under free radical conditions to provide intermediates of formula XXIV. Isoxazoles of formula XXIV can be obtained commercially, can be prepared by methods known in the literature, can be prepared by analogy to Scheme 2, or can be readily prepared by one skilled in the art. Intermediates of formula XXIV were treated with tetrabutylammonium fluoride to afford intermediates of formula XXV. [See: Sun, H.; DiMagno, S. G., J. Am. Chem. Soc. 2005, 127, 2050-2051.] Treatment of intermediates of formula XXV with trifluoroacetic acid provided compounds of formula IVf.

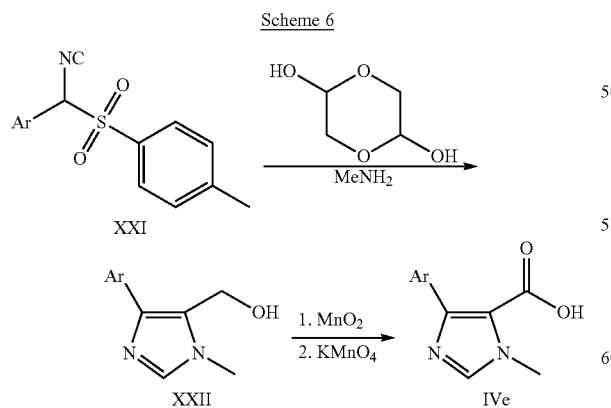

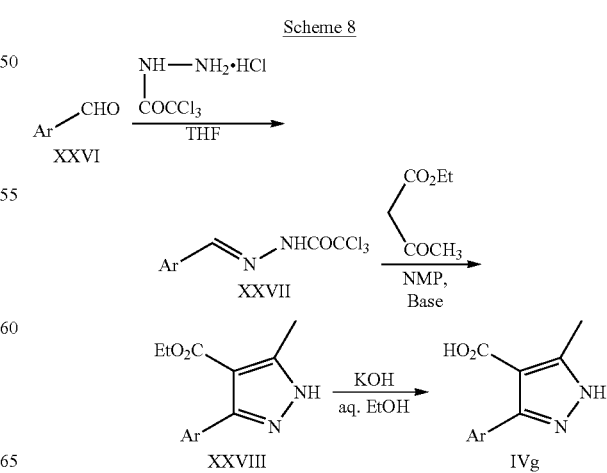

Compounds of formula IVe were prepared as outlined in Scheme 6 and as described in the literature. [See: Luke, R. W. A.; Jones, C. D.; McCoull, W; Hayter, B. R. WO Patent 2004013141, 2004.] Isocyanates of formula XXI were treated Compounds of formula IVg were prepared as outlined in Scheme 8 and as described in the literature. [See: El Kaim, L.; Lacroix, S. *Synlett,* 2000, 3, 353-354.] Aldehydes of formula XXVI were condensed with trichloroacetylhydrazide to afford hydrazones of formula XXVII. Aldehydes of formula XXVI can be obtained commercially, can be prepared by methods known in the literature, or can be readily prepared by one skilled in the art. Treatment of hydrazones of formula XXVII with ethyl acetoacetate under basic conditions afforded pyrazoles of formula XXVIII, which were hydrolyzed in a subsequent step to afford compounds of formula IVg.

Scheme 9

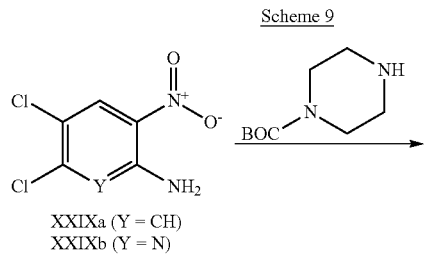

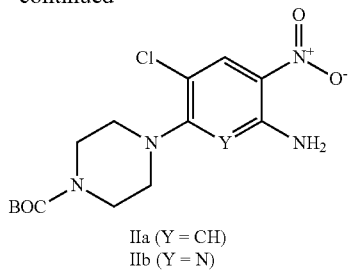

Compounds of formula IIa (Y═CH) and IIb (Y═N) were prepared as outlined in Scheme 9. Treatment of intermediate of formula XXIXa or XXIXb with BOC-protected piperazine afforded compounds of formula IIa and IIb, respectively. Intermediate of formula XXIXa can be obtained commercially, can be prepared by methods known in the literature, or can be readily prepared by one skilled in the art. Intermediate of formula XXIXa can be obtained commercially, can be prepared by methods known in the literature [See: Micheli, F.; Cugola, A.; Donati, D.; Missio, A.; Pecunioso, A.; Reggiani, A.; Tarzia, G. *Bioorg. Med. Chem.,* 1997, 5(12), 2129.], or can be readily prepared by one skilled in the art.

Scheme 10

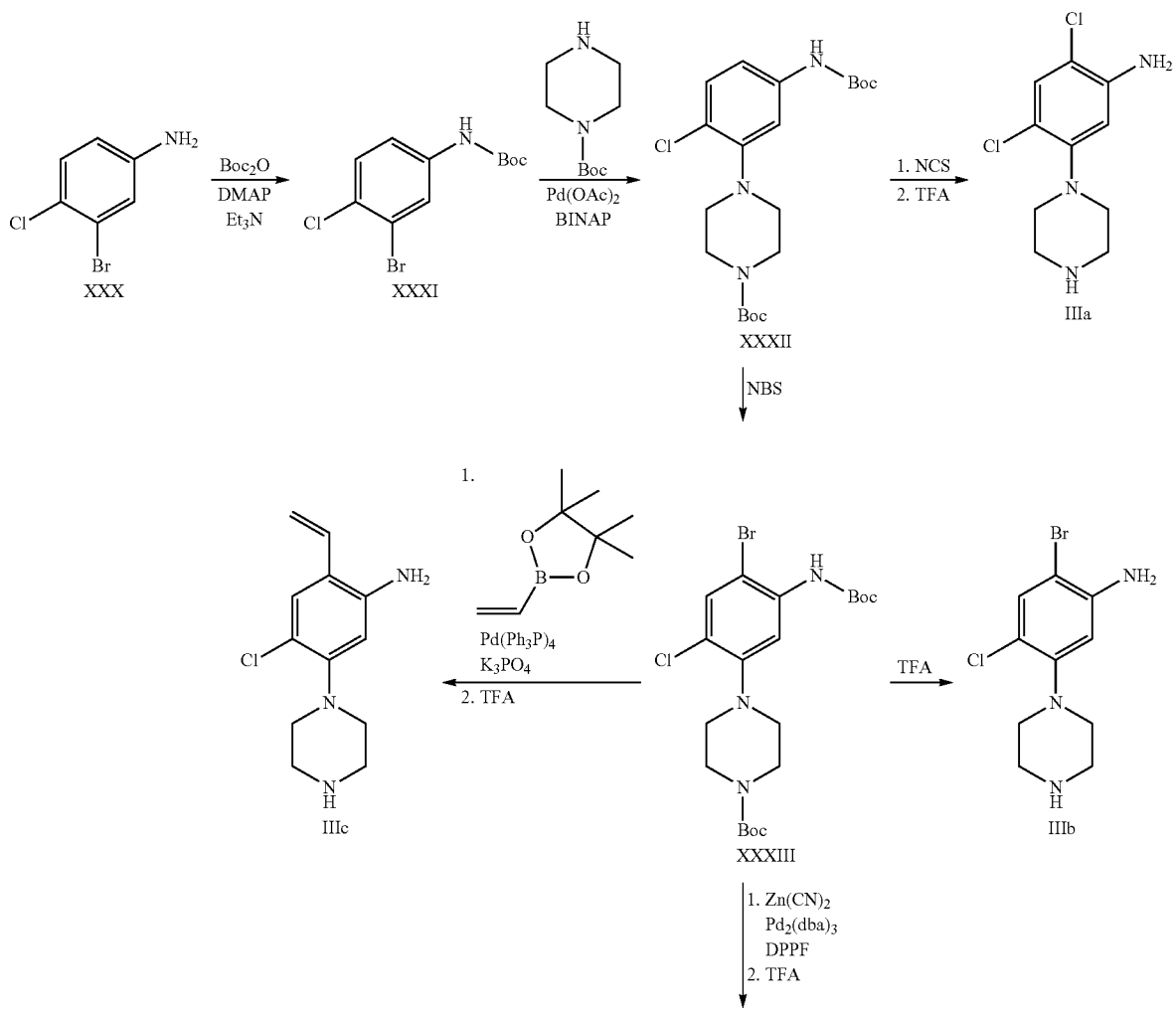

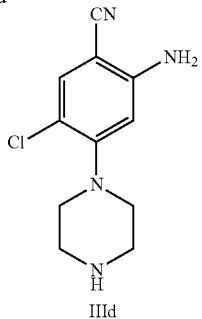

IIId

Compounds of formula IIIa-d were prepared as outlined in Scheme 10. Treatment of 3-bromo-4-chloroaniline (XXX) with Boc anhydride provided BOC-aniline of formula XXXI. Treatment of BOC-aniline of formula XXXI with BOC-piperazine and a Pd(II) catalyst afforded intermediate of formula XXXII, which upon sequential treatment with N-chlorosuccinimide and trifluoroacetic acid provided compound of formula Ina. Alternatively, intermediate of formula XXXII was treated with N-bromosuccinimide to afford intermediate of formula XXXIII. Treatment of intermediate of formula XXXIII with trifluoroacetic acid provided compound of formula IIIb. Alternatively, treatment of intermediate of formula XXXIII with vinyl pinacolboronate and a Pd(0) catalyst followed by trifluoroacetic acid provided compound of formula Inc. Alternatively, treatment of intermediate of formula XXXIII with Zn(II) cyanide and a Pd(0) catalyst followed by trifluoroacetic acid provided compound of formula Ind.

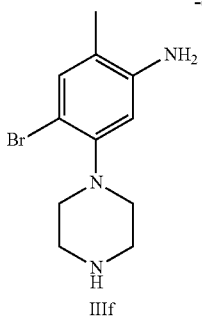

IIIf

Compounds of formula IIIe-f were prepared as outlined in Scheme 11. Boc-protected aniline of formula XXXIV was treated with BOC-piperazine and a Pd(II) catalyst to afford intermediate of formula XXXV. Sequential treatment of intermediate of formula XXXV with N-chlorosuccinimide and trifluoroacetic acid provided compound of formula IIIe. Alternatively, sequential treatment of intermediate of formula XXXV with N-bromosuccinimide and trifluoroacetic acid provided compound of formula IIIf.

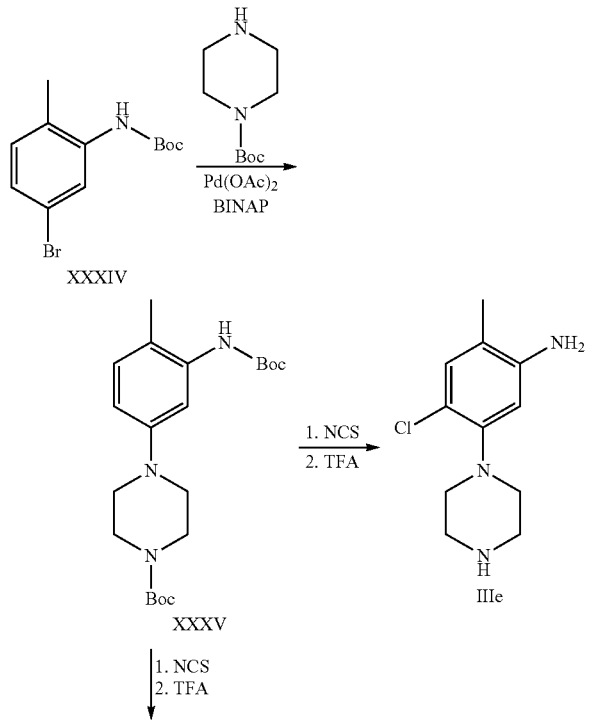

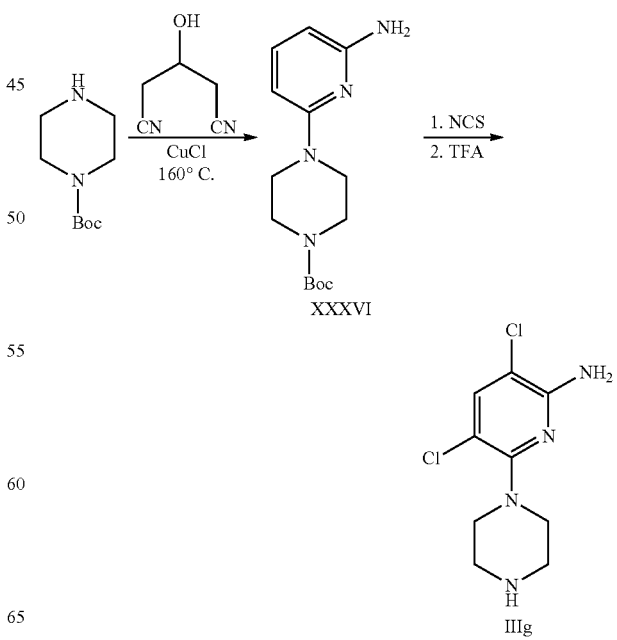

Compound of formula IIIg was prepared as outlined in Scheme 12. Boc-piperazine was heated with 1,3-dicyano-2-propanol to provide intermediate of formula XXVI. Sequential treatment of intermediate of formula XXXVI with N-chlorosuccinimide and trifluoroacetic acid provided compound of formula IIIg.

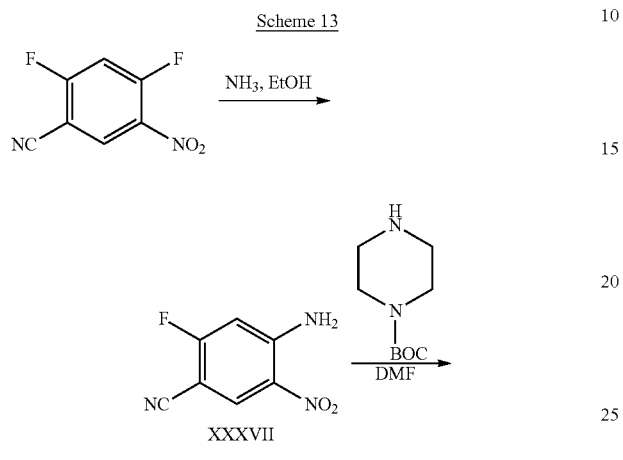

Compound of formula IIc was prepared as outlined in Scheme 13. Treatment of 2,4-difluoro-5-nitrobenzonitrile with ethanolic ammonia provided intermediate of formula XXVII. [See: Ohmori, J.; Sakamoto, S.; Kubota, H.; Shimizu-Sasamata, M. et. al. *J. Med. Chem.*, 1994, 37(4), 467-475.] Treatment of intermediate of formula XXXVII with Boc-piperazine provided compound of formula IIc.

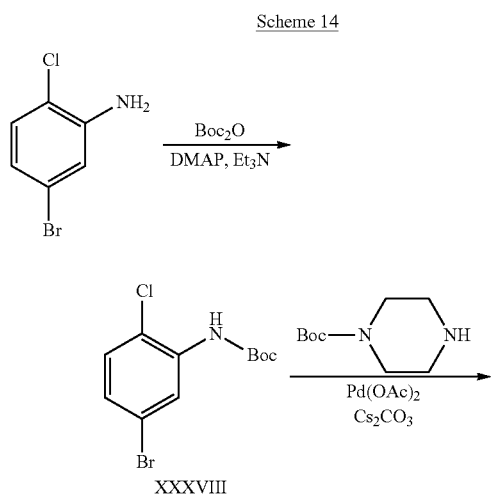

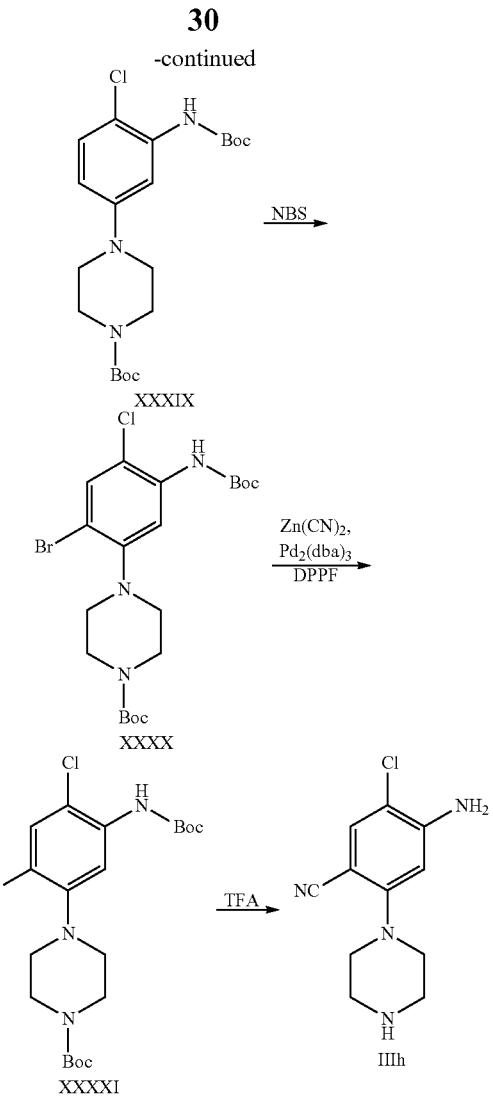

Compound of formula IIIh was prepared as outlined in Scheme 14. Treatment of 3-bromo-2-chloroaniline with Boc anhydride provided BOC-aniline of formula XXXVIII. Treatment of BOC-aniline of formula XXXVIII with BOC-piperazine and a Pd(II) catalyst afforded intermediate of formula XXXIX, which upon treatment with N-bromosuccinimide provided intermediate of formula XXXX. Treatment of intermediate of formula XXXX with Zn(II) cyanide and a Pd(0) catalyst afforded intermediate of formula XXXXI, which upon treatment with trifluoroacetic acid provided compound of formula IIIh.

EXAMPLES

The compounds herein described and set forth and their preparation can be understood further by the following working examples. These examples are meant to be illustrative of the present invention, and are not to be taken as limiting the scope thereof.

Chemical abbreviations used in the Examples are defined as follows:

"Ac" for acetate,
"APCI" for atmospheric pressure chemical ionization,
"BEMP" for 2-tert-butimino-2-diethylamino-1,3-dimethyl-perhydro-1,3,2-diaza-phosphorine, "Boc" or "BOC" for t-butyloxycarbonyl,
"BOP" for benzotriazol-1-yloxytris-(dimethylamino)-phosphonium hexafluorophosphate,
"Cbz" for benzyloxycarbonyl,
"CDI" for 1,1'-carbonyldiimidazole,
"CD$_3$OD" for deuteromethanol,
"CDCl$_3$" for deuterochloroform,
"DCC" for 1,3-dicyclohexylcarbodiimide,
"DCE" for 1,2-dichloroethane,
"DCM" for dichloromethane
"DEAD" for diethyl azodicarboxylate,
"DIEA", "Hunig's base", or "DIPEA" for N,N-diisopropylethylamine,
"DMF" for N,N-dimethylformamide,
"DMAP" for 4-dimethylaminopyridine,
"DMPU" for 1,3-dimethyl-3,4,5,6-tetrahydro-2(1H)-pyrimidone,
"DMSO" for dimethylsulfoxide,
"DPPA" for diphenylphosphorylazide
"EDC" or "EDCI" for 1-(3-dimethylaminopropyl)-3-ethylcarbodiimide hydrochloride,
"Et" for ethyl,
"EtOAC" for ethyl acetate,
"HOAc" for acetic acid,
"HOBt" for 1-hydroxybenzotriazole hydrate,
"HATU" for O-(7-azabenzotriazol-1-yl)-N,N,N',N'-tetramethyluronium hexafluorophosphate,
"HMPA" for hexamethylphosphoramide,
"LDA" for lithium diisopropylamide,
"LiHMDS" for lithium bis(trimethylsilyl)amide,
"NaHMDS" for sodium bis(trimethylsilyl)amide,
"NBS" for N-bromosuccinimide,
"NCS" for N-chlorosuccinimide,
"NMM" for 4-methylmorpholine,
"PyBOP" for benzotriazole-1-yl-oxy-tris-pyrrolidino-phosphonium hexafluorophosphate,
"TMSCH$_2$N$_2$" for (trimethylsilyl)diazomethane,
"TMSN$_3$" for Azidotrimethylsilane,
"TBTU" for O-(1H-benzotriazol-1-yl)-N,N,N',N'-tetramethyluronium tetrafluoroborate,
"TEA" for triethylamine,
"TFA" for trifluoroacetic acid, and
"THF" for tetrahydrofuran.

Abbreviations used in the Examples are defined as follows: "° C." for degrees Celsius, "MS" for mass spectrometry, "ESI" for electrospray ionization mass spectroscopy, "HR" for high resolution, "LC-MS" for liquid chromatography mass spectrometry, "eq" for equivalent or equivalents, "g" for gram or grams, "h" for hour or hours, "mg" for milligram or milligrams, "mL" for milliliter or milliliters, "mmol" for millimolar, "M" for molar, "min" for minute or minutes, "rt" for room temperature, "NMR" for nuclear magnetic resonance spectroscopy, "tlc" for thin layer chromatography, "atm" for atmosphere, and "α", "β", "R", "S", "E", and "Z" are stereochemical designations familiar to one skilled in the art.

"HPLC" is an abbreviation used herein for high pressure liquid chromatography. Reverse-phase HPLC can be carried out using a Vydac C-18 column with gradient elution from 10% to 100% buffer B in buffer A (buffer A: water containing 0.1% trifluoroacetic acid, buffer B: 10% water, 90% acetonitrile containing 0.1% trifluoroacetic acid). If necessary, organic layers can be dried over sodium sulfate unless otherwise indicated. However, unless otherwise indicated, the following conditions are generally applicable. "LC-MS" refers to high pressure liquid chromatography carried out according to the definition for HPLC with a mass spectrometry detector.

Melting points were determined on a Mel-Temp II apparatus and are uncorrected. IR spectra were obtained on a single-beam Nicolet Nexus FT-IR spectrometer using 16 accumulations at a resolution of 4.00 cm$^{-1}$ on samples prepared in a pressed disc of KBr or as a film on KBr plates. Proton NMR spectra (300 MHz, referenced to tetramethylsilane) were obtained on a Varian INOUA 300, Bruker Avance 300, Avance 400, or Avance 500 spectrometer. Data were referred to the lock solvent. Electrospray Ionization (ESI) experiments were performed on a Micromass II Platform single-quadrupole mass spectrometer, or on a Finnigan SSQ7000 mass spectrometer.

| Method | Method Name | Column | Solvent A | Solvent B | Gradient Time (min)* | Flow rate (ml/min) | λ |
|---|---|---|---|---|---|---|---|
| A | GL-2 | XTERRA 3.0 × 50 MM S7 | 5% ACN - 95% H2O - 10 mM NH4Ac | 95% ACN - 5% H2O - 10 mM NH4Ac | 3 | 4 | 220 |
| B | SZ-3 | SunFire C18 5u 4.6 × 50 mm | 90% Water/ 10% ACN/ 0.1% TFA | 10% Water/ 90% ACN/ 0.1% TFA | 3 | 4 | 220 |
| C | SZ-4 | Phenomenex-Luna 3.0 × 50 mm S10 | 5% ACN - 95% H2O - 10 mM NH4Ac | 95% ACN - 5% H2O - 10 mM NH4Ac | 3 | 4 | 220 |
| D | SZ-5 | Phenomenex-Luna 3.0 × 50 mm S10 | 5% ACN - 95% H2O - 10 mM NH4Ac | 95% ACN - 5% H2O - 10 mM NH4Ac | 2 | 4 | 220 |
| E | SZ-6 | Phenomenex-Luna 3.0 × 50 mm S10 | 10% MeOH - 90% H2O - 0.1% TFA | 90% MeOH - 10% H2O - 0.1% TFA | 3 | 4 | 220 |
| F | SZ-8 | Phenomenex-Luna, 2.0 × 50 mm, 3u | 90% H2O - 10% ACN - 0.1% TFA | 10% H2O - 90% ACN - 0.1% TFA | 4 | 0.8 | 220 |
| G | SZ-10 | Luna 3.0 × 50 mm S10 | 5% ACN - 95% H2O - 10 mM NH4Ac | 95% ACN - 5% H2O - 10 mM NH4Ac | 3 | 4 | 220 |

| Method | Method Name | Column | Solvent A | Solvent B | Gradient Time (min)* | Flow rate (ml/min) | λ |
|---|---|---|---|---|---|---|---|
| H | SZ-11 | Phenomenex-Luna 3.0 × 50 mm S10 | 5% MeOH - 95% H2O - 10 mM NH4Ac | 95% MeOH - 5% H2O - 10 mM NH4Ac | 2 | 4 | 220 |
| I | JS-12 | Phenomenex-Luna 3.0 × 50 mm S10 | 90% Water/ 10% ACN/ 0.1% TFA | 10% Water/ 90% ACN/ 0.1% TFA | 2 | 4 | 254 |
| J | JS-15 | Phenomenex-Luna 3.0 × 50 mm S10 | 10% MeOH - 90% H2O - 0.1% TFA | 90% MeOH - 10% H2O - 0.1% TFA | 2 | 4 | 254 |
| K | SZ-16 | XTERRA MS C18 S7 3.0 × 50 MM | 5% MeOH - 95% H2O - 10 mM NH4Ac | 95% MeOH - 5% H2O - 10 mM NH4Ac | 2 | 5 | 220 |
| L | SZ-17 | Phenomenex-Luna 3.0 × 50 mm S10 | 5% MeOH - 95% H2O - 10 mM NH4Ac | 95% MeOH - 5% H2O - 10 mM NH4Ac | 4 | 4 | 220 |
| M | JS-18 | Phenomenex-Luna C18, 30 × 2, 3u | 90% Water/ 10% ACN/ 0.1% TFA | 10% Water/ 90% ACN/ 0.1% TFA | 2 | 4 | 254 |
| N | WZ-19 | Phenomenex-Luna C18, 30 × 2, 3u | 90% H2O - 10% ACN - 0.1% TFA | 10% H2O - 90% ACN - 0.1% TFA | 4 | 1 | 220 |

*All HPLC gradients were run from 0% to 100% B.

Preparatory HPLC: When described as performed under "standard conditions", Samples (approx. 20 mg) were dissolved in methanol (10 mg/mL) and purified on a 25 mm×50 mm Vydac C18 column with a 5 minute gradient elution from 10% to 100% buffer B in buffer A (buffer A: water containing 0.1% trifluoroacetic acid, buffer B: 10% water, 90% acetonitrile containing 0.1% trifluoroacetic acid) at 10 mL/minute.

Synthesis of Intermediates

Preparation A: 3-(2-methoxyphenyl)-5-methylisoxazole-4-carboxylic acid

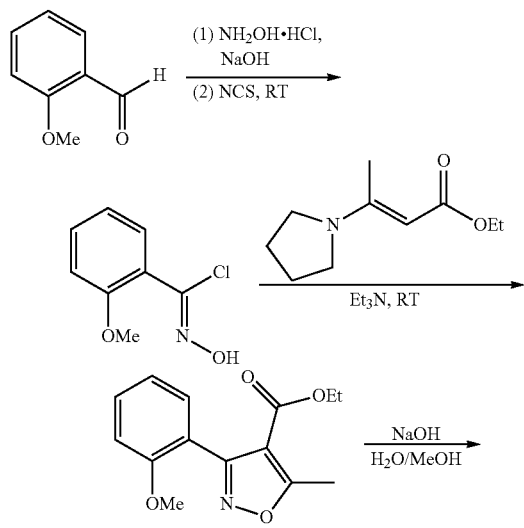

-continued

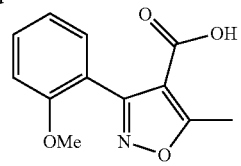

Step A1.

Ethyl 3-(2-methoxyphenyl)-5-methylisoxazole-4-carboxylate was synthesized from 2-methoxybenzaldehyde as described in [Zamponi, G. W.; Stotz, S. C.; Staples, R. J.; Andro, T. M.; Nelson, J. K.; Hulubei, V.; Blumenfeld, A.; Natale, N. R. *J. Med. Chem.* 2003, 46, 87-96.]

Step A2.

The reaction mixture of ethyl 3-(2-methoxyphenyl)-5-methylisoxazole-4-carboxylate (12.85 g, 49.2 mmol) and sodium hydroxide (9.84 g, 246 mmol) in MeOH (100 mL) and Water (10 mL) in a 500-mL round bottom flask was stirred at 65° C. for 20 hours. The MeOH was removed in vacuo, then the concentrated reaction mixture was transferred to a 500-mL separatory funnel with 150 mL of water and 100 mL of ether. The organic layer was discarded. The aqueous layer was acidified by adding concentrated HCl (26 mL). The product precipitated and was separated by filtration and dried under high vacuum to give 10.63 g (93%, theoretical yield 11.47 g). $^1$H NMR (400 MHz, CD$_3$OD) δ 2.69 (s, 3H, CH$_3$), 3.77 (s, 3H, OCH$_3$), 7.00-7.07 (m, 2H, aryl), 7.32-7.34 (m, $^1$H, aryl), 7.43-7.48 (m, $^1$H, aryl).

Preparation B:
5-methyl-3-(naphthalen-1-yl)isoxazole-4-carboxylic acid

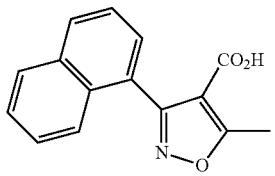 [SMILES: Cc1onc(-c2cccc3ccccc23)c1C(=O)O]

The title compound was prepared by analogy to Preparation A, substituting 1-naphthaldehyde for 2-methoxybenzaldehyde. $^1$H-NMR (DMSO, 400 MHz): δ 7.83-8.22 (m, 3H), 7.4-7.7 (m, 4H), 3.5 (2H, bs), 2.74 (3H, s). m/e 254 (M+H)$^+$.

Preparation C: 3-(2-chloro-6-methoxyphenyl)-5-methylisoxazole-4-carboxylic acid

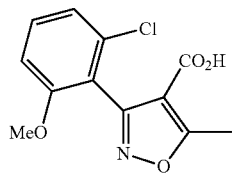 [SMILES: COc1cccc(Cl)c1-c1noc(C)c1C(=O)O]

The title compound was prepared by analogy to Preparation A, substituting 2-chloro-6-methoxybenzaldehyde for 2-methoxybenzaldehyde. $^1$H NMR (CD$_3$OD, 500 MHz,) δ 7.41 (1H, t, J=8.4 Hz), 7.09 (1H, d, J=7.6 Hz), 7.03 (1H, d, J=8.2 Hz), 3.76 (3H, s), 2.74 (3 H, s).

Preparation D: 5-(2-methoxyphenyl)-3-methyl-1H-pyrazole-4-carboxylic acid

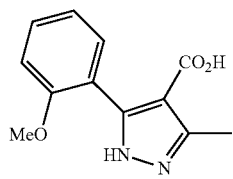

The title compound was prepared according to the literature procedure: El Kaim, L.; Lacroix, S. *Synlett*, 2000, 3, 353-354. $^1$H-NMR (CDCl$_3$, 400 MHz): δ 7.28-7.40 (1H, m), 7.17-7.25 (1H, m), 6.90-7.08 (2H, m), 2.38 (3H, s). m/e 233 (M+H)$^+$.

Preparation E: 3-(2-chlorophenyl)-5-methyl-1H-pyrazole-4-carboxylic acid

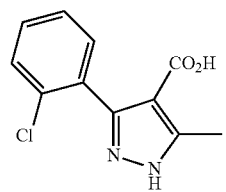 [SMILES: Cc1[nH]nc(-c2ccccc2Cl)c1C(=O)O]

The title compound was prepared by analogy to Preparation D. $^1$H-NMR (CDCl$_3$, 400 MHz): δ 7.45-7.55 (1H, m), 7.28-7.40 (2H, m), 7.25-7.27 (1H, m), 2.44 (3H, s).

Preparation F: 2-(2-Chlorophenyl)-4-methyl-1H-pyrrole-3-carboxylic acid

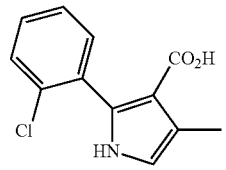 [SMILES: Cc1c[nH]c(-c2ccccc2Cl)c1C(=O)O]

The title compound was prepared according to the literature procedure: Grigg, R.; Savic, V. *Chem. Commun.* 2000, (10), 873-874. $^1$H-NMR (CDCl$_3$, 400 MHz): δ 7.52-7.63 (1H, m), 7.41-7.48 (2H, m), 7.28-7.32 (1H, m), 6.8-6.85 (1H, m), 2.17 (3H, s).

Preparation G: 1-(2-methoxyphenyl)-4-methyl-1H-pyrazole-5-carboxylic acid

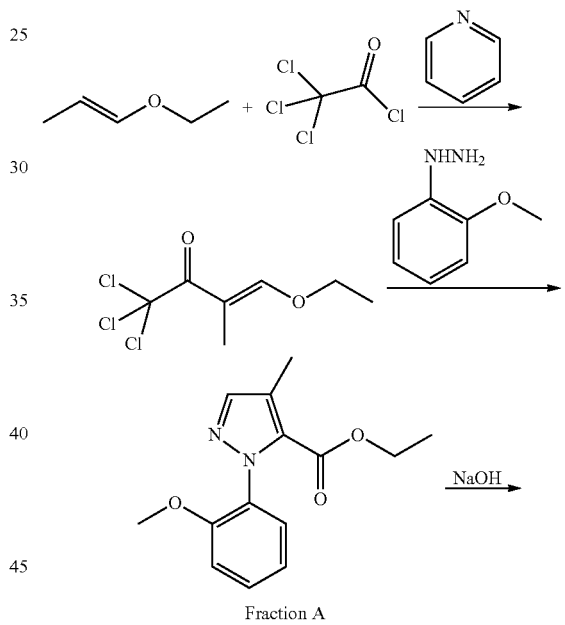

Fraction A

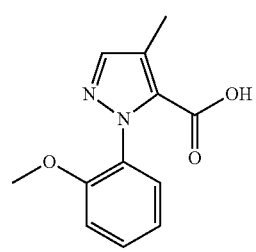

Reference: Martins, M. A. P. et al. *J. Molecular Catalysis A: Chemical*, 2007, 266,100.

Step G1.

A mixture of (E)-1-ethoxyprop-1-ene (6.41 mL, 57.9 mmol) and pyridine (4.68 mL, 57.9 mmol) was added to a soln. of 2,2,2-trichloroacetyl chloride (10.53 g, 57.9 mmol) in DCM (15 mL) at −10° C. at a rate of 6-10 drops/min. After the addition was completed, the mixture was stirred at r.t for 24 hrs. Filtered, and the filtrate was concentrated in reduced pressure (at first the temperature of the water bath was r.t, after most DCM was evaporated off, water bath was warmed to 50° C. to afford (E)-1,1,1-trichloro-4-ethoxy-3-methylbut-3-en-2-one (2.55 g, 10.79 mmol, 18.64% yield). 1H-NMR (500 MHz, CDCl$_3$): δ: 7.96 (s, 1H), 4.21 (q, J=7.1 Hz, 2H), 1.94 (s, 3H), 1.41 (t, J=7.2 Hz, 3H). This material was taken into Step G2 without further purification.

Step G2.

A mixture of (E)-1,1,1-trichloro-4-ethoxy-3-methylbut-3-en-2-one (279 mg, 1.205 mmol) and (2-methoxyphenyl)hydrazine, HCl (253 mg, 1.446 mmol) in EtOH (5 mL) was heated to reflux for 3 hrs. Cooled to r.t. then separated by Pre-HPLC to afford ethyl 1-(2-methoxyphenyl)-4-methyl-1H-pyrazole-5-carboxylate (Fraction A, 30 mg, 0.113 mmol, 9.37% yield) and ethyl 1-(2-methoxyphenyl)-4-methyl-1H-pyrazole-3-carboxylate (fraction B, 41 mg, 0.154 mmol, 12.81% yield).

$^1$H-NMR of fraction A: (500 MHz, CD3OD): δ: 7.58 (s, 1H), 7.48-7.44 (m, 1H), 7.35 (d, J=7 Hz, 1H), 7.14 (d, J=7.2 Hz), 7.10-7.07 (m, 1H), 4.16 (q, J=7.1 Hz, 2H), 3.76 (s, 3H), 2.34 (s, 3H), 1.11 (t, J=7 Hz, 3H).

$^1$H-NMR of isomer B: (500 MHz, CD3OD): δ: 7.91 (s, 1H), 7.61 (d, J=8.2 Hz, 1H), 7.36 (d, J=7 Hz, 1H), 7.23 (d, J=8.2 Hz, 1H), 7.12-7-08 (m, 1H), 4.41 (q, J=7 Hz, 2H), 3.76 (s, 3H), 2.35 (s, 3H), 1.42 (t, J=7 Hz, 3H).

Step G3.

Hydrolysis of Fraction A: To a soln. of ethyl 1-(2-methoxyphenyl)-4-methyl-1H-pyrazole-5-carboxylate (30 mg, 0.115 mmol) in MeOH (2 mL) was added 3 N sodium hydroxide (2 ml, 6.00 mmol). The resulting mixture was stirred at r.t for 2 hrs, then evaporated to remove the solvent. The residue was taken up in EtOAc and water, acidified with 6N HCl to pH=2, partitioned and extracted with EtOAc. The organic layer was dried (Na$_2$SO4) and evaporated to afford 1-(2-methoxyphenyl)-4-methyl-1H-pyrazole-5-carboxylic acid (23 mg, 0.094 mmol, 82% yield), which was taken into the next reaction without further purification.

Preparation H: 4-(2-methoxyphenyl)-1-methyl-1H-imidazole-5-carboxylic acid

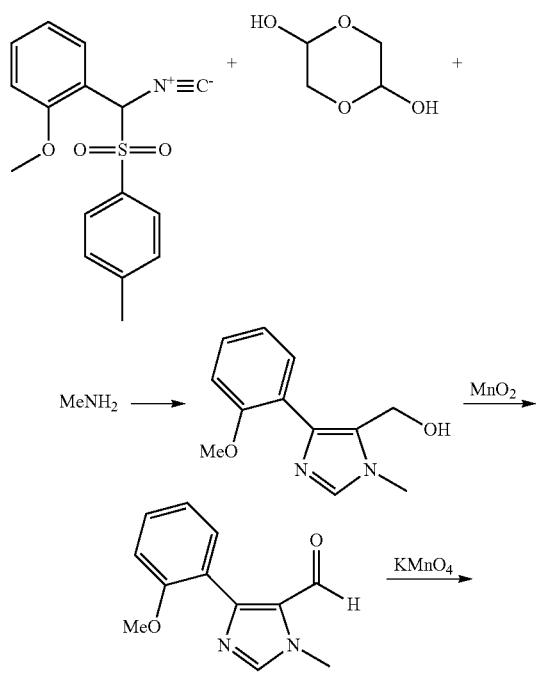

Reference: Luke, R. W. A.; Jones, C. D.; McCoull, W; Hayter, B. R. WO Patent 2004013141, 2004.

Step H1.

To a soln. of 1,4-dioxane-2,5-diol (120 mg, 0.995 mmol) in THF (8 ml) was added methylamine (2.8 ml, 0.664 mmol) at r.t. The resulting mixture was stirred at r.t for 75 min. Then 1-(isocyano(tosyl)methyl)-2-methoxybenzene (200 mg, 0.664 mmol) was added while keeping reaction mixture at <30° C. by a water bath. The reaction mixture was stirred at r.t overnight. Evaporated to leave white solid, dissolved in DMF, and purified by Pre-HPLC to afford (4-(2-methoxyphenyl)-1-methyl-1H-imidazol-5-yl)methanol (84 mg, 0.377 mmol, 38.6% yield) as a colorless oil. $^1$H-NMR (MeOD), δ: 8.97 (1H, s), 7.55 (1H, t, J=7.5 Hz), 7.47 (1H, d, J=8.0 Hz), 7.22 (1H, d, 8.0 Hz), 7.15 (1H, t, J=7.5 Hz), 4.67 (2H, s), 4.05 (3H, s), 3.89 (3H, s).

Step H2.

To a soln. of (4-(2-methoxyphenyl)-1-methyl-1H-imidazol-5-yl)methanol (84 mg, 0.385 mmol) in 1,4-Dioxane (5 ml) was added MnO2 (147 mg, 1.693 mmol). The mixture was heated to 90° C. for 4 hrs or until LC/MS showed the completion of the reaction. The reaction mixture was Filtered through celite, and evaporated to afford 4-(2-methoxyphenyl)-1-methyl-$^1$H-imidazole-5-carbaldehyde (78 mg, 0.325 mmol, 84% yield), which was used for the next reaction w/o purification.

Step H3.

To a soln. of 4-(2-methoxyphenyl)-1-methyl-1H-imidazole-5-carbaldehyde (78 mg, 0.361 mmol) in acetone (5 ml) and water (1 ml) was added potassium carbonate (100 mg, 0.721 mmol). After potassium was dissolved, KMnO4 (123 mg, 0.776 mmol) was added at r.t. The mixture was stirred for 24 hrs. LC/MS showed the completion. The mixture was filtered through celite, washed w/water. The actone was evaporated from the filtrate which was extracted with EtOAc (2x). The aq. layer was acidified w/HOAc to PH=5, reduced the volume to half volume, feezed and lyphilized to leave solid, which was purified by Pre-HPLC to afford the title compound (41 mg, 0.173 mmol, 48% yield). $^1$H-NMR (MeOD), δ: 8.06 (s, 1H), 7.41-7.36 (m, 2H), 7.05-6.99 (m, 2H), 3.98 (s, 3H), 3.80 (s, 3H).

Preparation I: 4-(2-fluorophenyl)-1-methyl-1H-imidazole-5-carboxylic acid

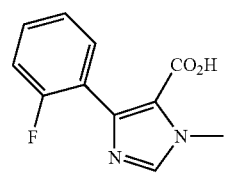 [SMILES: Cn1cnc(-c2ccccc2F)c1C(=O)O]

The title compound was prepared in 61% overall by analogy to Preparation H. $^1$H-NMR (DMSO), δ: 7.93 (s, 1H), 7.45-7.38 (m, 2H), 7.23-7.17 (m, 2H), 3.85 (s, 3H).

Preparation J: 4-(2-methoxyphenyl)-1-methyl-1H-1,2,3-triazole-5-carboxylic acid

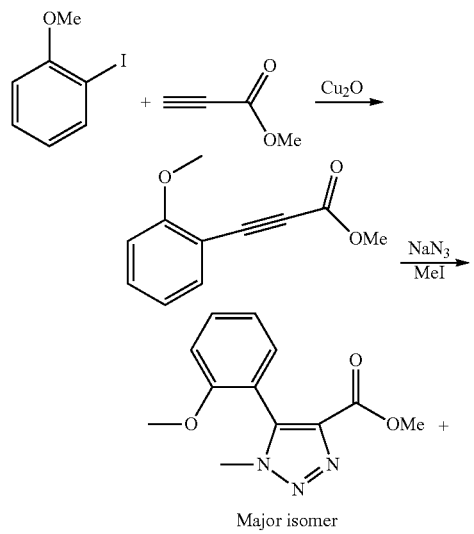

Major isomer

Minor isomer

| NaOH

Step J1:
Reference: Liliebris, C.; Larsen, S. D; Ogg, D.; Palazuk, B. J; and Pleasdale, J. E. *J. Med. Chem.*, 2002, 45, 1785.

To a suspension of methyl propiolate (2, 1.314 ml, 15.41 mmol) and copper(I) oxide (1.086 g, 7.59 mmol) in DMF (20 ml) was added 1-iodo-2-methoxybenzene (1, 1.262 ml, 9.48 mmol). The resulting mixture was heated in a Microwave reactor to 110° C. for 2 hrs. The reaction mixture was filtered through a short pad of silica gel and washed w/EtOAc. The organic layer was washed w/1M HCl, brine and sat'd NaHCO$_3$, dried (Na$_2$SO$_4$) and concentrated to leave an oil as crude product, which was purified by flash chromatography (SiO$_2$, EtOAc/Hexane, 1:2) to afford methyl 3-(2-methoxyphenyl)propiolate 3 (932 mg, 4.66 mmol, 49.1% yield). $^1$H-NMR (500 MHz, CDCl$_3$), δ: 7.54 (1H, dd), 7.44 (1H, td), 6.98-6.92 (m, 2H), 3.92 (s, 3H), 3.86 (s, 3H).

Step J2:
A mixture of methyl 3-(2-methoxyphenyl)propiolate (3, 932 mg, 4.90 mmol), sodium azide (478 mg, 7.35 mmol), and iodomethane (0.458 ml, 7.35 mmol) in Water (7 ml) and DMF (3 ml) was heated to 100° C. in a Microwave reactor for 6 hrs. Purified by Prep-HPLC (Varian, 15-90B in min., B=90% MeOH/10% H2O) to afford methyl 5-(2-methoxyphenyl)-1-methyl-1H-1,2,3-triazole-4-carboxylate (701 mg, 2.69 mmol, 55.0% yield), $^1$H-NMR (500 MHz, CD3OD), δ: 7.52-7.56 (m, 1H), 7.30 (dd, 1H), 7.12, (td, 1H), 7.06, (d, 1H), 3.90 (s, 3H), 3.86 (s, 3H), 3.82 (s, 3H). and methyl 4-(2-methoxyphenyl)-1-methyl-1H-1,2,3-triazole-5-carboxylate (185 mg, 0.711 mmol, 14.51% yield), $^1$H-NMR (500 MHz, CD3OD), δ: 7.49-7.46 (m, 2H), 7.10-7.07 (m, 2H), 4.32 (s, 3H), 3.79 (s, 3H), 3.78 (s, 3H).

Step J3:
To a soln. of methyl 4-(2-methoxyphenyl)-1-methyl-1H-1,2,3-triazole-5-carboxylate (183 mg, 0.74 mmol) in MeOH (5 ml) was added sodium hydroxide (1.3 ml, 3M aq. solution). The mixture was stirred at r.t for 2 hrs, then concentrated in vacuo. The residue was taken up in water, washed w/ether (3×) to remove the possible impurity. The aq. phase was acidified w/6M HCl to pH 3, extracted w/EtOAc (4×). The combined organic layer was dried and evaporated to afford the title compound (164 mg, 0.703 mmol, 95% yield). $^1$H-NMR (500 MHz, CD3OD), δ: 7.46-7.42 (m, 2H), 7.09-7.05 (m, 2H), 4.32 (s, 3H), 3.73 (s, 3H).

Preparation K: 5-(fluoromethyl)-3-(2-methoxyphenyl)isoxazole-4-carboxylic acid

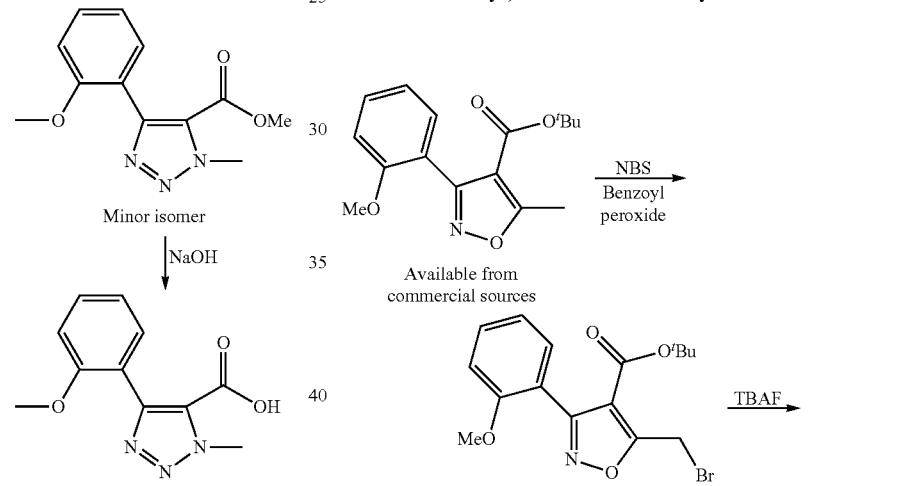

Available from commercial sources

Step K1:
A solution of tert-butyl 3-(2-methoxyphenyl)-5-methyl-isoxazole-4-carboxylate (0.795 g, 2.75 mmol), NBS (0.978 g, 5.50 mmol) and benzoyl peroxide (0.033 g, 0.137 mmol) in CCl$_4$ (10 mL) was stirred at 90° C. for 16 hours. The reaction mixture was cooled to RT and the solid was filtered off. Solvent was removed in vacuo. The product was purified by flash chromatography (DCM, Rf 0.56) to give 0.44 g (44% yield). ¹H-NMR (CDCl₃, 400 MHz): δ 7.49-7.37 (2H, m), 7.04 (1H, t, J=7.5 Hz), 6.96 (1H, d, J=8.3 Hz), 4.79 (2H, s), 3.79 (3H, s), 1.38 (9H, s).

Step K2:

tert-butyl 5-(fluoromethyl)-3-(2-methoxyphenyl)isoxazole-4-carboxylate was prepared from tert-Butyl 5-(bromomethyl)-3-(2-methoxyphenyl)isoxazole-4-carboxylate by the method described in Sun, H.; DiMagno, S. G., *J. Am. Chem. Soc.* 2005, 127, 2050-2051. ¹H-NMR (CDCl₃, 400 MHz): δ 7.49-7.37 (2H, m), 7.08-7.01 (1H, m), 6.97 (1H, d, J=8.3 Hz), 5.72 (2H, d, J=47.2 Hz), 3.79 (3H, s), 1.35 (9H, s).

Step K3:

Treating tert-butyl 5-(fluoromethyl)-3-(2-methoxyphenyl)isoxazole-4-carboxylate with TFA/DCM (1:1) at room temperature for one hour followed by evaporation of DCM/TFA in vacuo provided the title compound. ¹H-NMR (CD₃OD, 400 MHz): δ 7.53-7.44 (1H, m), 7.42-7.35 (1H, m), 7.13-6.98 (2H, m), 5.74 (2H, d, J=47.2 Hz), 3.78 (3H, s).

Preparation L. (4-(5-amino-2-chloro-4-nitrophenyl)piperazin-1-yl)(3-(2-methoxyphenyl)-5-methylisoxazol-4-yl)methanone

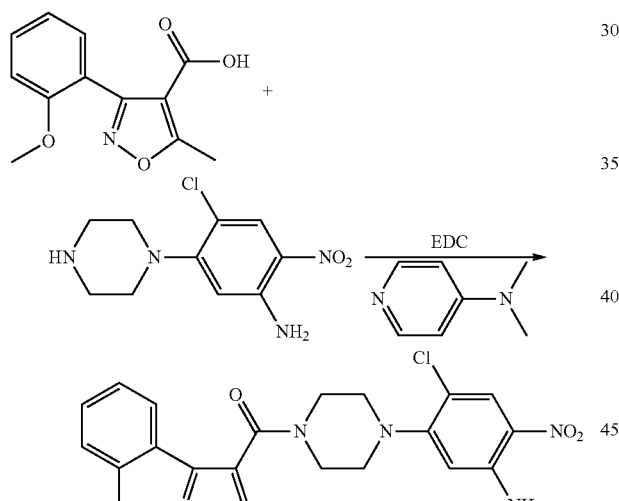

A mixture of 3-(2-methoxyphenyl)-5-methylisoxazole-4-carboxylic acid (363 mg, 1.558 mmol, Preparation A), 4-chloro-2-nitro-5-(piperazin-1-yl)aniline (400 mg, 1.558 mmol, prepared as described in [El-Abadelah, M. M.; Nazer, M. Z.; El-Abadla, N. S.; Awadallah, A. M. *Asian Journal of Chemistry* 1999, 11(4), 1463-1468.]), EDC (448 mg, 2.337 mmol), and N,N-dimethylpyridin-4-amine (571 mg, 4.67 mmol) in DCM (5 mL)/DMF (3 mL) was stirred overnight. The solution was diluted with DCM, then washed with water for three times. Purification via flash chromatography with 20% EtOAc in DCM provided the title compound (286 mg, 0.606 mmol, 38.9% yield). ¹H-NMR (CDCl₃, 400 MHz): δ8.11 (1H, s), 7.59 (1H, d, J=7.53 Hz), 7.47 (1H, t, J=8.53 Hz), 7.08 (1H, t, J=7.53 Hz), 6.99 (1H, d, J=7.28 Hz), 6.03 (1H, s), 3.80 (3H, s), 3.8 (2H, s) 3.22 (2H, s), 3.01 (2H, s), 2.57 (3H, s), 2.46 (2H, s).

Preparation M. (4-(5-amino-2,4-dichlorophenyl)piperazin-1-yl)(3-(2-methoxyphenyl)-5-methylisoxazol-4-yl)methanone

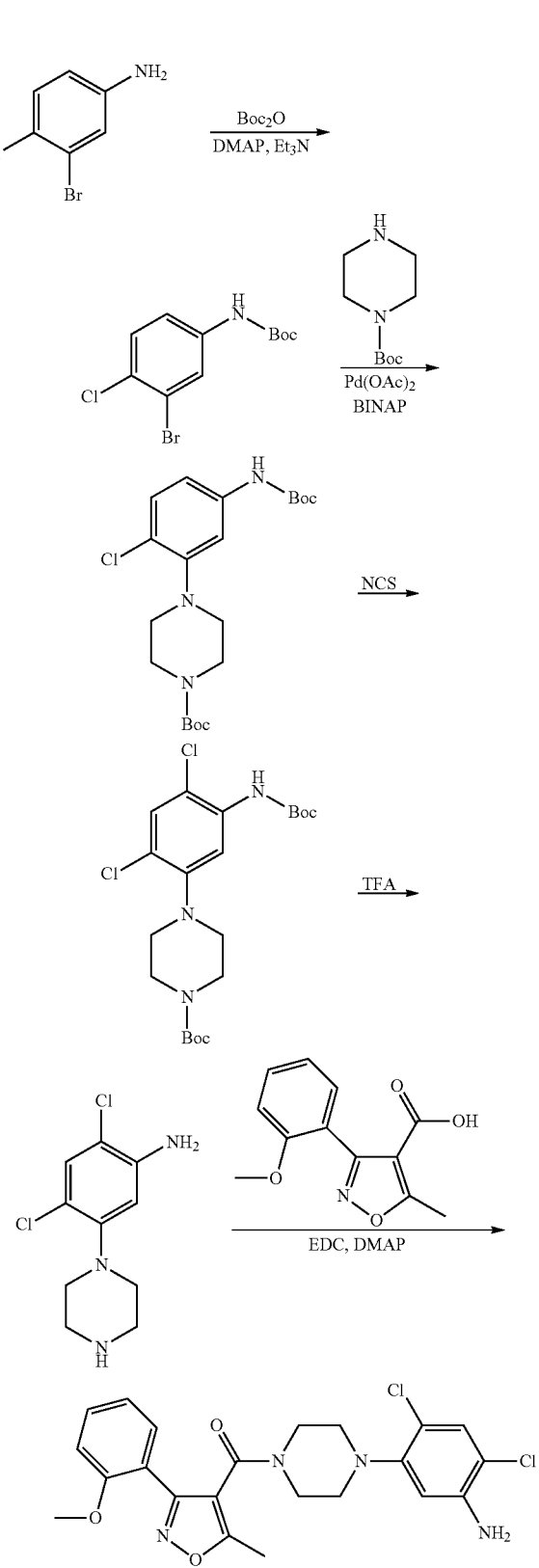

Step M1:

To a solution of 3-bromo-4-chloroaniline (2.26 g, 10.95 mmol) in DCM (20 mL) was added triethylamine (3.32 g, 32.8 mmol). The solution was cooled to 0° C., followed by the addition of di-tert-butyl dicarbonate (2.87 g, 13.14 mmol). The ice-water bath was removed and N,N-dimethylpyridin-4-amine (1.337 g, 10.95 mmol) was added. The resulted reaction mixture was stirred at RT overnight. The product was purified by flash chromatography (Hexanes/DCM, 1:1, Rf 0.45) to give 2.96 g (88% yield). $H^1$-NMR (CDCl$_3$, 400 MHz): δ 7.79 (1H, d, J=2.5 Hz), 7.34 (1H, d, J=8.8 Hz), 7.21 (1H, dd, J1=8.8 Hz, J2=2.5 Hz), 6.44 (1H, s), 1.53 (9H, s).

Step M2:

The reaction mixture of tert-butyl 3-bromo-4-chlorophenylcarbamate (1.39 g, 4.53 mmol), tert-butyl piperazine-1-carboxylate (1.689 g, 9.07 mmol), diacetoxypalladium (0.127 g, 0.567 mmol), 2,2'-bis(diphenylphosphino)-1,1'-binaphthyl (0.282 g, 0.453 mmol) and cesium carbonate (1.847 g, 5.67 mmol) in toluene (10 mL) was stirred at 110° C. overnight. Water (150 mL) was added after the reaction mixture was cooled to RT and the product was extracted with DCM (3×120 mL). The product was purified by flash chromatography (5% EtOAc/DCM, Rf 0.45) to give 1.11 g (59% yield). $H^1$-NMR (CDCl$_3$, 400 MHz): δ 7.27-7.22 (2H, m), 6.86 (1H, dd, J1=8.5 Hz, J2=2.5 Hz), 6.45 (1H, s), 3.60 (4H, t, J=5.0 Hz), 3.00 (4H, t, J=5.0 Hz), 1.52 (9H, s), 1.49 (9H, s).

Step M3:

To a solution of tert-butyl 4-(3-(tert-butoxycarbonylamino)-4-chlorophenyl)piperazine-1-carboxylate (570 mg, 1.384 mmol) in DCM (3 mL) and methanol (6 mL) at −40° C. was added a solution of trifluoroacetic acid (0.107 mL, 1.384 mmol) in 1.5 mL of DCM. NCS (222 mg, 1.661 mmol) was added and the temperature was allowed to rise to RT slowly. The reaction mixture was stirred at RT overnight. Saturated NaHCO$_3$ aqueous solution (50 mL) was added and the product was extracted with DCM (3×50 mL). The product was purified by flash chromatography (5% EtOAc/DCM, Rf 0.73) to give 0.452 g (73% yield). $H^1$-NMR (CDCl$_3$, 400 MHz): δ 7.98 (1H, s), 7.34 (1H, s), 6.94 (1H, s), 3.60 (4H, t, J=5.0 Hz), 3.01 (4H, t, J=5.0 Hz), 1.54 (9H, s), 1.49 (9H, s).

Step M4:

A solution of tert-butyl 4-(5-(tert-butoxycarbonylamino)-2,4-dichlorophenyl)piperazine-1-carboxylate (94.8 mg, 0.212 mmol) in trifluoroacetic acid (0.5 mL, 6.49 mmol) and DCM (0.5 mL) was stirred at RT for one hour. Solvent was evaporated to give 97 mg the product (96% yield). $H^1$-NMR (CD$_3$OD, 400 MHz): δ 7.23 (1H, s), 6.64 (1H, s), 3.37 (4H, t, J=5.0 Hz), 3.22 (4H, t, J=5.0 Hz).

Step M5:

The reaction mixture of 3-(2-methoxyphenyl)-5-methyl-isoxazole-4-carboxylic acid (0.131 g, 0.561 mmol), 2,4-dichloro-5-(piperazin-1-yl)aniline, 2 TFA (0.253 g, 0.534 mmol), EDC (0.123 g, 0.641 mmol) and DMAP (0.130 g, 1.07 mmol) in DCM (4 mL) was stirred at RT overnight. The crude product was purified by flash chromatography (MeOH/DCM, gradient 2%-4%, Rf 0.31 with 3% MeOH) to give 0.221 g of the title compound (90% yield). $^1$H-NMR (CD$_3$OD, 400 MHz): δ 7.57-7.50 (2H, m), 7.19 (1H, s), 7.18-7.07 (2H, m), 6.43 (1H, s), 3.81 (3H, s), 3.74 (2H, s), 3.24 (2H, s), 2.88 (2H, s), 2.53 (3H, s), 2.35 (2H, s).

Preparation N. (4-(5-amino-4-bromo-2-chlorophenyl)piperazin-1-yl)(3-(2-methoxyphenyl)-5-methyl-isoxazol-4-yl)methanone

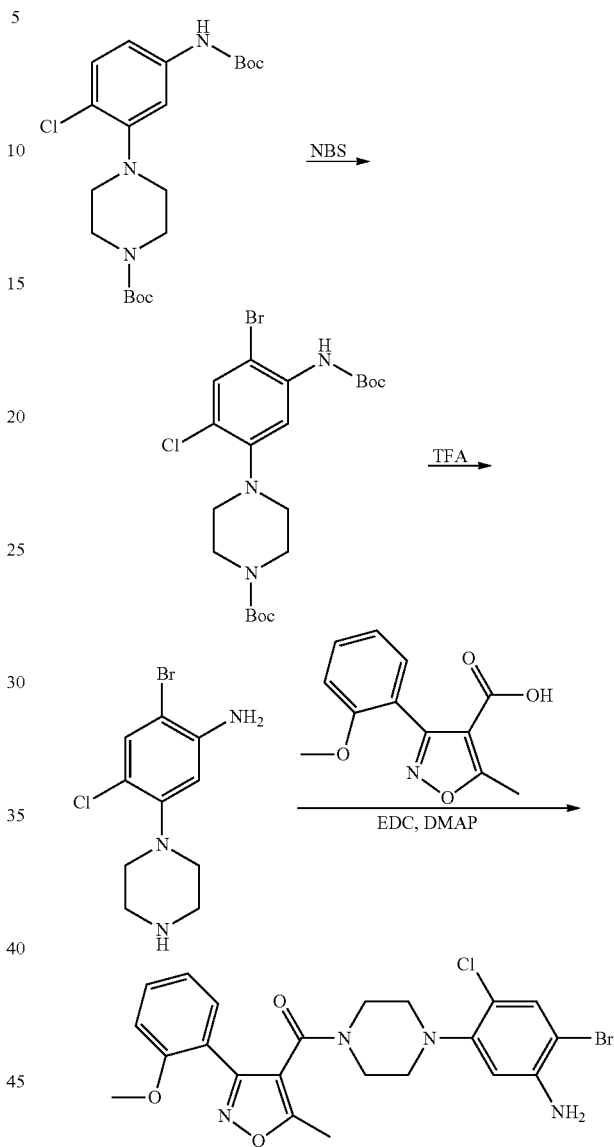

Step N1:

To the solution of tert-butyl 4-(5-(tert-butoxycarbonylamino)-2-chlorophenyl)piperazine-1-carboxylate (363 mg, 0.881 mmol, obtained via Step M2 of Preparation M) in DCM (10 mL) and methanol (5 mL) was added NBS (157 mg, 0.881 mmol). The resulted reaction mixture was stirred at RT for one hour. LCMS showed that the reaction was complete. Solvent was evaporated in vacuo and the product was purified by flash chromatography (5% EtOAc/DCM) to give 435 mg (82% yield).

$^1$H-NMR (CDCl$_3$, 400 MHz): δ 7.97 (1H, s), 7.50 (1H, s), 6.93 (1H, s), 3.60 (4H, t, J=5.0 Hz), 3.02 (4H, t, J=5.0 Hz), 1.54 (9H, s), 1.49 (9H, s).

Step N2:

This reaction was performed by analogy to Step M4 of Preparation M.

$H^1$-NMR (CD$_3$OD, 400 MHz): δ 7.37 (1H, s), 6.63 (1H, s), 3.37 (4H, t, J=5.0 Hz), 3.22 (4H, t, J=5.0 Hz).

Step N3:

This reaction was performed by analogy to Step M5 of Preparation M to provide the title compound.

$^1$H-NMR (CD$_3$OD, 400 MHz): δ 7.62-7.54 (1H, m), 7.50-7.40 (1H, m), 7.36 (1H, s), 7.11-6.95 (2H, m), 6.19 (1H, s), 3.80 (3H, s), 3.79 (2H, s), 3.20 (2H, s), 2.87 (2H, s), 2.56 (3H, s), 2.34 (2H, s).

Preparation O. N-(4-chloro-2-nitro-5-(piperazin-1-yl)phenyl)-4-(dimethylamino)benzamide

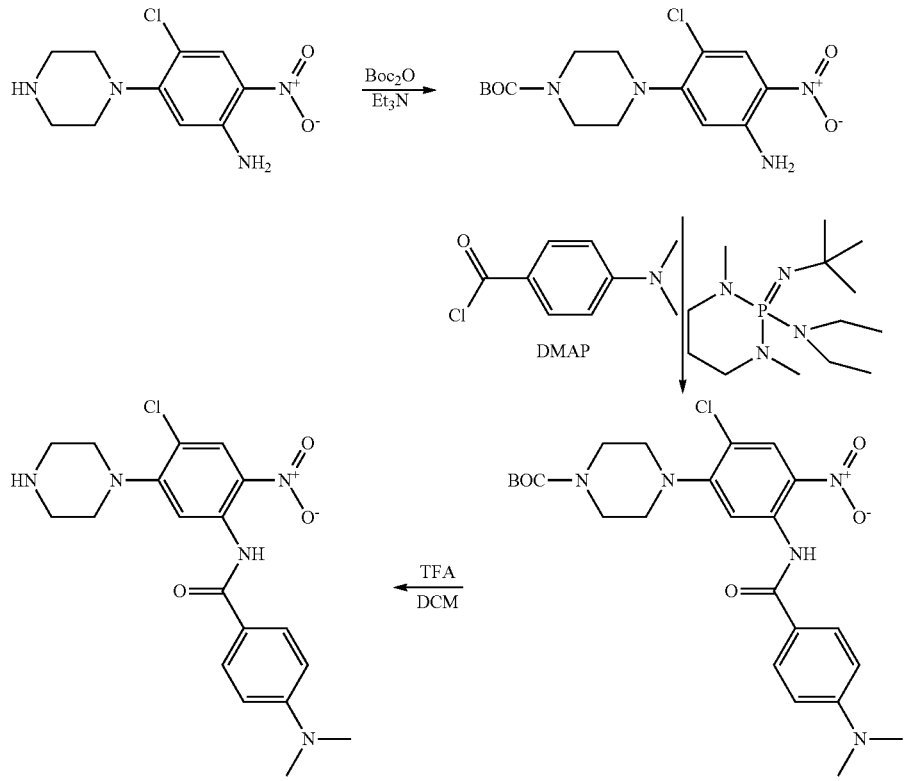

Step O1:

A mixture of 4-chloro-2-nitro-5-(piperazin-1-yl)aniline (1.4 g, 5.45 mmol, prepared as described in [El-Abadelah, M. M.; Nazer, M. Z.; El-Abadla, N. S.; Awadallah, A. M. *Asian Journal of Chemistry* 1999, 11(4), 1463-1468.]), di-tert-butyl dicarbonate (1.190 g, 5.45 mmol), and triethylamine (0.552 g, 5.45 mmol) in DCM (50 mL) was stirred for 2 h. After solvent was removed, the mixture was purified by silicon gel column with 2% EtOAc in DCM gave tert-butyl 4-(5-amino-2-chloro-4-nitrophenyl)piperazine-1-carboxylate (1.8 g, 91%). $^1$H-NMR (CDCl$_3$, 500 MHz): δ 8.16 (1H, s), 6.22 (1H, s), 3.61 (4H, m), 3.09 (4H, m), 1.49 (9H, s).

Step O2:

A mixture of tert-butyl 4-(5-amino-2-chloro-4-nitrophenyl)piperazine-1-carboxylate (1.2 g, 3.36 mmol), 4-(N,N-dimethylamino)benzoyl chloride (803 mg, 4.37 mmol), BEMP (1846 mg, 6.73 mmol), and DMAP (411 mg, 3.36 mmol) in DCE (Volume: 15 ml) was heated at 85° C. foe 4 h. Cooled down and treated with a few drops of piperidine for 1 h. After the solvent was removed and mixture was diluted with MeOH, a orange precipitate formed. Filtration and washing with MeOH gave tert-butyl 4-(2-chloro-5-(4-(dimethylamino)benzamido)-4-nitrophenyl)piperazine-1-carboxylate (1.2 g, 2.381 mmol, 70.8% yield). $^1$H-NMR (CDCl$_3$, 500 MHz): δ 11.53 (1H, s), 8.82 (1H, s), 8.31 (1H, s), 7.89 (2H, d, J=8.85 Hz), 6.74 (1H, d, J=8.85 Hz), 3.64 (4H, m), 3.27 (4H, m), 3.09 (6H, s), 1.50 (9H, s).

Step O3:

Tert-butyl 4-(2-chloro-5-(4-(dimethylamino)benzamido)-4-nitrophenyl)piperazine-1-carboxylate (1.2 g, 2.381 mmol) was stirred in TFA/DCM (50%, 10 ml) for 1 h. After the solvent was removed and the residue was dried in vacuum to give the title compound as its TFA salt (1.5 g, 2.374 mmol, 100%). $^1$H-NMR (CDCl$_3$, 500 MHz): M0.74 (1H, s), 8.89 (2H, s), 7.81 (2H, d, J=8.85 Hz), 6.81 (2H, d, J=8.85 Hz), 3.35 (8H, m), 3.03 (6H, s).

Preparation P. 2-amino-5-chloro-4-(4-(3-(2-methoxyphenyl)-5-methylisoxazole-4-carbonyl)piperazin-1-yl)benzonitrile

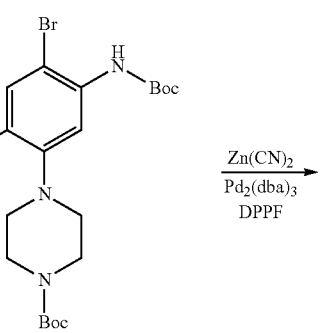

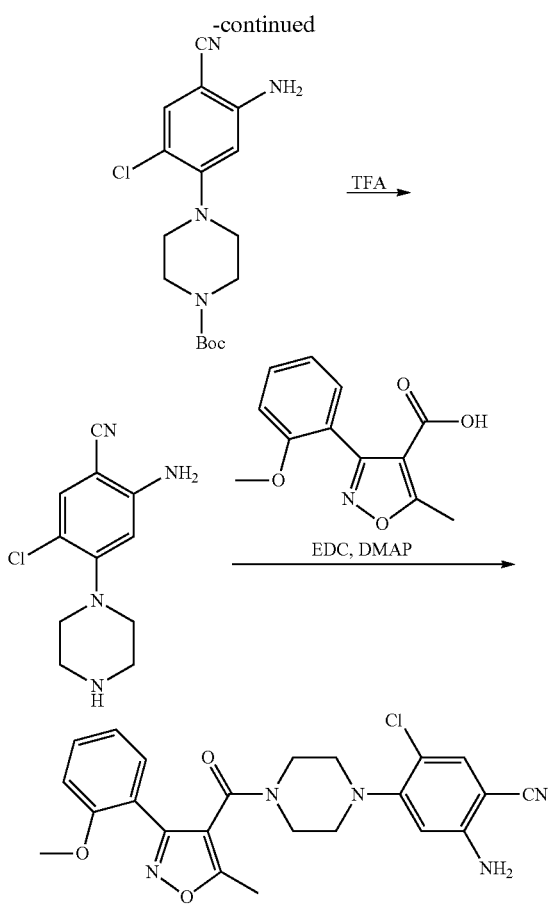

Step P1:

To a mixture of tert-butyl 4-(4-bromo-5-(tert-butoxycarbonylamino)-2-chlorophenyl)piperazine-1-carboxylate (1.11 g, 2.26 mmol, obtained via Step N1 of Preparation N) and dicyanozinc (159 mg, 1.36 mmol) was added DMF (22 mL) and Water (0.30 mL). Nitrogen was bubbled into the mixture for 5 min., followed by the addition of $Pd_2(dba)_3$ (2.69 mg, 2.94 mmol) and DPPF (2.0 mg, 3.61 μmol). The resulted mixture was heated at 120° C. for 4 hours. The product was purified by flash chromatography (EtOAc/DCM, gradient 5%40%) to give 0.35 g of the title compound (5% EtOAc/DCM, Rf 0.31). $^1$H-NMR (CDCl$_3$, 400 MHz): δ 7.35 (1H, s), 6.28 (1H, s), 4.38 (2H, s), 3.60 (4H, t, J=5.0 Hz), 3.03 (4H, t, J=5.0 Hz), 1.49 (9H, s).

Step P2:

A solution of tert-butyl 4-(5-amino-2-chloro-4-cyanophenyl)piperazine-1-carboxylate (14 mg, 0.042 mmol) and TFA (0.2 mL, 2.60 mmol) in DCM (0.2 mL) was stirred at room temperature for one hour. Solvent was evaporated in vacuo to give the product. $^1$H-NMR (CD$_3$OD, 400 MHz): δ 7.37 (1H, s), 6.54 (1H, s), 3.39 (4H, t, J=5.0 Hz), 3.31 (4H, m).

Step P3:

The reaction mixture of 3-(2-methoxyphenyl)-5-methylisoxazole-4-carboxylic acid (10.00 mg, 0.043 mmol), 2-amino-5-chloro-4-(piperazin-1-yl)benzonitrile, 2 TFA (16.6 mg, 0.036 mmol), EDC (9.59 mg, 0.050 mmol) and DMAP (8.73 mg, 0.071 mmol) in DCM (1 mL) was stirred at room temperature overnight. The product was purified by preparative HPLC (0.1% TFA MeOH/H$_2$O) to give 11 mg (52% yield) of the title compound. $^1$H-NMR (CDCl$_3$, 400 MHz): δ 7.59 (1H, dd, J1=7.5 Hz, J2=1.8 Hz), 7.52-7.46 (1H, m), 7.33 (1H, s), 7.13-6.97 (2H, m), 6.06 (1H, s), 3.84 (2H, s), 3.80 (3H, s), 3.25 (2H, s), 2.98 (2H, s), 2.57 (3H, s), 2.43 (2H, s).

Preparation Q. (4-(5-amino-2,4-dichlorophenyl)piperazin-1-yl)(5-(fluoromethyl)-3-(2-methoxyphenyl)isoxazol-4-yl)methanone

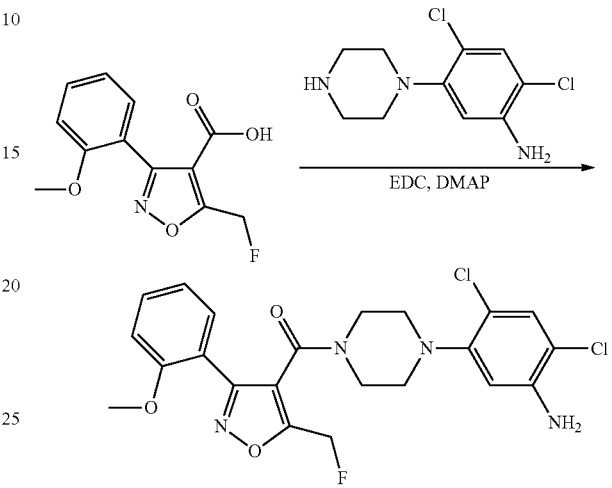

Preparation Q was synthesized by analogy to Step M5 of Preparation M, substituting Preparation K for 3-(2-methoxyphenyl)-5-methylisoxazole-4-carboxylic acid. $H^1$-NMR (CD$_3$OD, 400 MHz): δ 7.60-7.51 (2H, m), 7.20-7.07 (3H, m), 6.41 (1H, s), 5.57 (2H, d, J=47.4 Hz), 3.82 (3H, s), 3.75 (2H, m), 3.24 (2H, m), 2.89 (2H, m), 2.36 (2H, m).

Preparation R. 4-amino-5-chloro-2-(4-(3-(2-methoxyphenyl)-5-methylisoxazole-4-carbonyl)piperazin-1-yl)benzonitrile

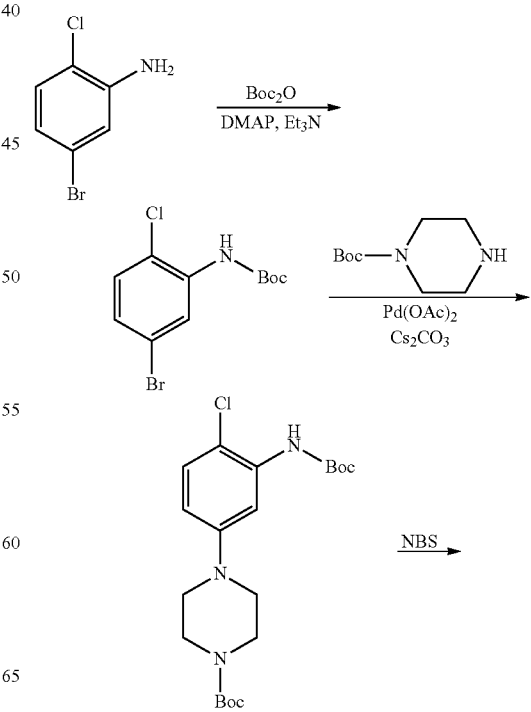

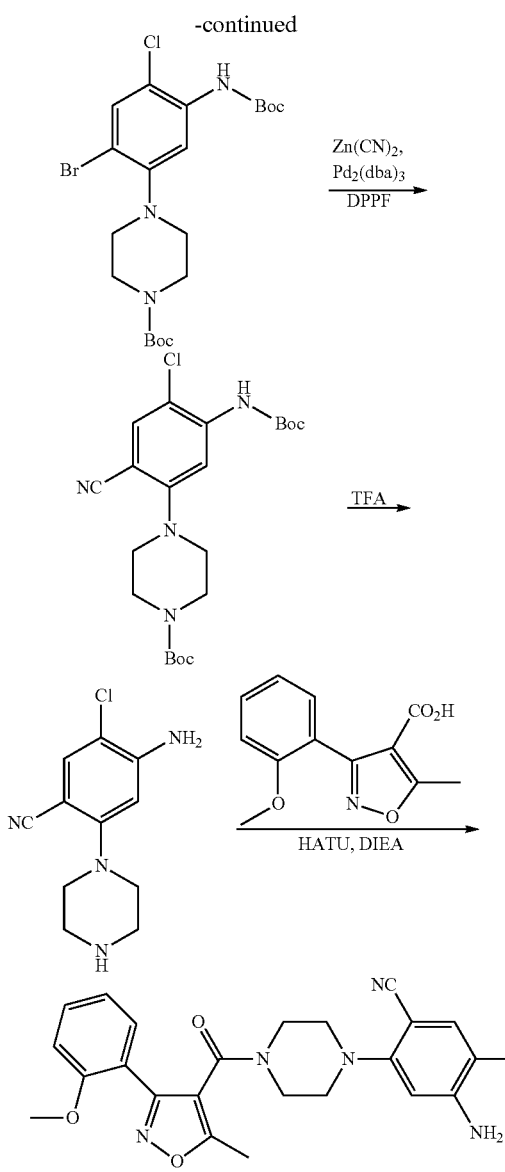

Step R1:

To 5-bromo-2-chloroaniline (2.917 g, 14.13 mmol) in DCM (15 mL) was added triethylamine (5.91 mL, 42.4 mmol). The reaction was cooled to 0° C., and di-tert-butyl dicarbonate (3.94 mL, 16.95 mmol) was added. The reaction was warmed to ambient temp., and DMAP (1.726 g, 14.13 mmol) was added. Violent bubbling and precipitate were observed within one minute. The reaction mixture was stirred at RT for 16 hours. The product was purified by flash chromatography (DCM/Hexanes 1:1, Rf 0.61) to give 4.21 g (97% yield). $^1$H-NMR (CDCl$_3$, 400 MHz): δ 8.43 (1H, d, J=2.0 Hz), 7.19 (1H, d, J=8.5 Hz), 7.09 (1H, dd, J1=8.5 Hz, J2=2.5 Hz), 6.99 (1H, s), 1.55 (9H, s).

Step R2:

The reaction mixture of tert-butyl 5-bromo-2-chlorophenylcarbamate (0.598 g, 1.951 mmol), tert-butyl piperazine-1-carboxylate (0.727 g, 3.90 mmol), diacetoxypalladium (0.055 g, 0.244 mmol), 2,2'-bis(diphenylphosphino)-1,1'-binaphthyl (0.121 g, 0.195 mmol) and cesium carbonate (0.794 g, 2.438 mmol) in toluene (15 mL) was stirred at 110° C. overnight. Water (150 mL) was added after the reaction mixture was cooled to RT and the product was extracted with DCM (3×120 mL). The product was purified by flash chromatography (5% EtOAc/DCM, Rf 0.45) to give 0.56 g (69% yield). $^1$H-NMR (CDCl$_3$, 400 MHz): δ 7.87 (1H, d, J=2.8 Hz), 7.19 (1H, d, J=9.0 Hz), 6.98 (1H, s), 6.52 (1H, dd, J1=9.0 Hz, J2=2.8 Hz), 3.57 (4H, t, J=5.3 Hz), 3.15 (4H, t, J=5.3 Hz), 1.54 (9H, s), 1.49 (9H, s).

Step R3:

The reaction mixture of tert-butyl 4-(3-(tert-butoxycarbonylamino)-4-chlorophenyl)piperazine-1-carboxylate (190 mg, 0.461 mmol) and NBS (82 mg, 0.461 mmol) in DCM (4 mL) and MeOH (2 mL) was stirred at room temperature for one hour. Solvent was evaporated and the product was purified by flash chromatography (5% EtOAc/DCM) to give 216 mg (95% yield). $^1$H-NMR (CDCl$_3$, 400 MHz): δ 7.99 (1H, s), 7.53 (1H, s), 6.94 (1H, s), 3.61 (4H, t, J=4.9 Hz), 3.00 (4H, t, J=4.9 Hz), 1.54 (9H, s), 1.49 (9H, s).

Step R4:

The procedure as described in [Maligres, P. E. *Tetrahedron Lett.* 1999, 40, 8193-8195.] was followed. The product was purified by preparative HPLC (0.1% TFA MeOH/H2O) to give 60 mg (42% yield). $^1$H-NMR (CD$_3$OD, 400 MHz): δ 7.42 (1H, s), 6.45 (1H, s), 3.63-3.53 (4H, m), 3.05 (4H, t, J=5.0 Hz), 1.48 (9H, s).

Step R5:

The solution of tert-butyl 4-(5-amino-4-chloro-2-cyanophenyl)piperazine-1-carboxylate (144 mg, 0.428 mmol) and TFA (2 mL, 26.0 mmol) in DCM (2 ml) was stirred at room temperature for one hour. Solvent was evaporated in vacuo to give the product. $^1$H-NMR (CD$_3$OD, 400 MHz): δ 7.47 (1H, s), 6.53 (1H, s), 3.42-3.37 (4H, m), 3.37-3.32 (4H, m).

Step R6:

To a mixture of 3-(2-methoxyphenyl)-5-methylisoxazole-4-carboxylic acid (25.09 mg, 0.108 mmol), 4-amino-5-chloro-2-(piperazin-1-yl)benzonitrile, 2 TFA (50 mg, 0.108 mmol) and HATU (49.1 mg, 0.129 mmol) in NMP (1.5 mL) was added DIEA (0.045 mL, 0.258 mmol). The reaction mixture was stirred at room temperature overnight.

The crude product was purified by preparative HPLC (0.1% TFA MeOH/H2O) to give 20 mg (41% yield) of the title compound. $^1$H-NMR (CDCl$_3$, 400 MHz): δ 7.58 (1H, dd, J=7.5, 1.5 Hz), 7.46 (1H, td, J=7.9, 1.8 Hz), 7.41 (1H, s), 7.07 (1H, t, J=7.5 Hz), 6.98 (1 H, d, J=8.3 Hz), 6.09 (1H, s), 3.80 (3H, s), 3.23 (2H, br. s.), 3.01 (2H, br. s.), 2.57 (3H, s), 2.50 (2H, br. s.).

Preparation S. (4-(5-amino-2-chloro-4-vinylphenyl)piperazin-1-yl)(3-(2-methoxyphenyl)-5-methylisoxazol-4-yl)methanone

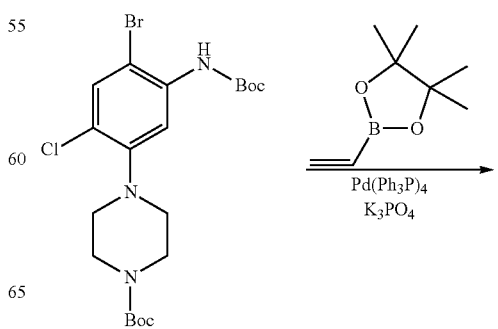

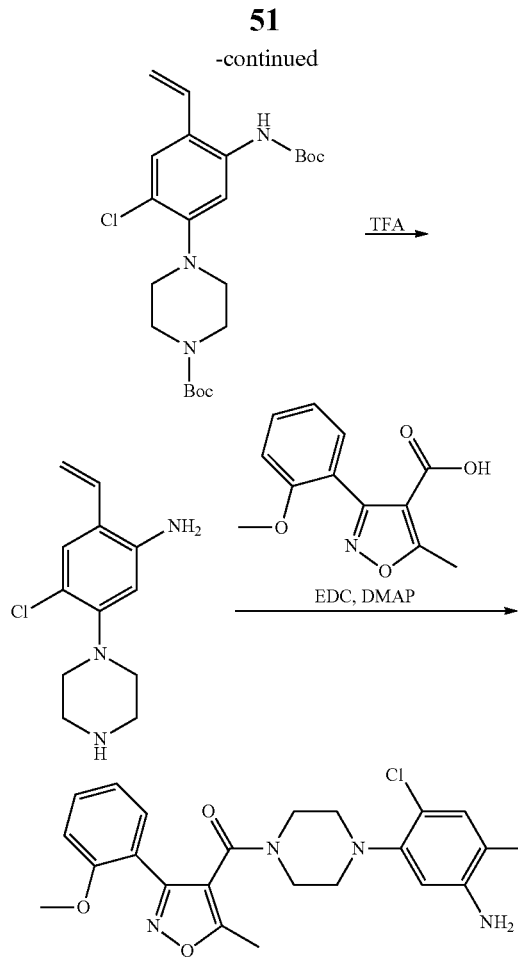

Step S1:

tert-Butyl 4-(4-bromo-5-(tert-butoxycarbonylamino)-2-chlorophenyl)piperazine-1-carboxylate (162 mg, 0.330 mmol, obtained via Step N1 of Preparation N) was dissolved in DMF (4 mL) in a 100-mL round bottom flask, followed by the addition of 4,4,5,5-tetramethyl-2-vinyl-1,3,2-dioxaborolane (50.8 mg, 0.330 mmol) and tripotassium phosphate (0.495 mL, 0.990 mmol). Nitrogen was bubbled through the solution for 10 min. Pd(Ph$_3$P)$_4$ (19.07 mg, 0.017 mmol) was added and the reaction mixture was stirred at 85° C. for 16 hours. The reaction mixture was cooled to RT, followed by the addition of 30 mL of water. The product was extracted with ethyl acetate (3×30 mL). The combined extract was dried over anhydrous sodium sulfate, which was removed by filtration.

The product was purified by flash chromatography (silica gel, 5% EtOAc/DCM, Rf 0.67) to give 75 mg (52% yield). $^1$H-NMR (CDCl$_3$, 400 MHz): δ 7.63 (1H, s), 7.37 (1H, s), 6.68 (1H, dd, J1=17.3 Hz, J2=11.0 Hz), 6.42 (1H, s), 5.60 (1H, d, J=17.3 Hz), 5.39 (1H, d, J=11.0 Hz), 3.60 (4H, t, J=5.0 Hz), 3.03 (4H, t, J=5.0 Hz), 1.52 (9H, s), 1.49 (9H, s).

Step S2:

tert-Butyl 4-(5-(tert-butoxycarbonylamino)-2-chloro-4-vinylphenyl)piperazine-1-carboxylate was treated with 1:1 mixture of trifluoroacetic acid and DCM at room temperature for one hour to give the deprotected product. $^1$H-NMR (CD$_3$OD, 400 MHz): δ7.61 (1H, s), 6.94 (1H, s), 6.80 (1H, dd, J1=17.3 Hz, J2=11.0 Hz), 5.76 (1H, d, J=17.1 Hz), 5.42 (1H, d, J=11.0 Hz), 3.41 (4H, t, J=5.0 Hz), 3.31 (4H, m).

Step S3:

To the mixture of 3-(2-methoxyphenyl)-5-methylisoxazole-4-carboxylic acid (0.182 g, 0.779 mmol), 4-chloro-5-(piperazin-1-yl)-2-vinylaniline, 2 TFA (0.279 g, 0.599 mmol) and HATU (0.296 g, 0.779 mmol) in a 100-mL round bottom flask was added NMP (5.5 mL) and triethylamine (0.145 g, 1.438 mmol). The resulted solution was stirred at room temperature for 13 hours. Water (50 mL) and DCM (50 mL) were added to the reaction mixture and the two phases were separated in a separatory funnel. The aqueous phase was extracted with DCM (2×40 mL). Solvent was evaporated by rotavap. The product was purified by preparative HPLC (acetonitrile/water–10 nM ammonium acetate) to give 0.146 g (54% yield) of the title compound.

$^1$H-NMR (CD$_3$OD, 400 MHz): δ 7.58-7.48 (2H, m), 7.22 (1H, s), 7.18-7.06 (2H, m), 6.74 (1H, dd, J1=17.3 Hz, J2=11.0 Hz), 6.28 (1H, s), 5.50 (1H, d, J=17.3 Hz), 5.17 (1H, d, J=11.0 Hz), 3.81 (3H, s), 3.74 (2H, s), 3.24 (2H, s), 2.89 (2H, s), 2.53 (3H, s), 2.35 (2H, s).

Preparation T. 4-(1H-1,2,4-triazol-1-yl)benzoyl chloride

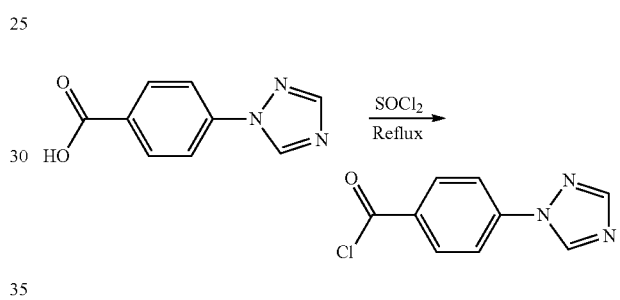

4-(1H-1,2,4-triazol-1-yl)benzoic acid (100 mg, 0.529 mmol) in sulfurous dichloride (2 ml) was refluxed at 110° C. for 2 h. After the excess SOCl$_2$ was removed, the residue was dried in vacuo to give 4-(1H-1,2,4-triazol-1-yl)benzoyl chloride (110 mg, 0.529 mmol, 100% yield) as a white solid which was used in subsequent reactions without further purification.

Preparation U. 4-(1H-tetrazol-1-yl)benzoyl chloride

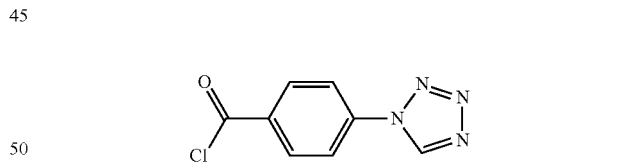

The title compound was prepared by analogy to Preparation T.

Preparation V.
4-(N-methylmethylsulfonamido)benzoyl chloride

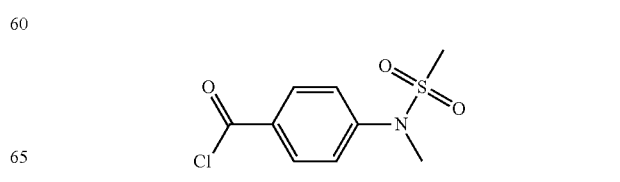

The title compound was prepared by analogy to Preparation T.

Preparation W.
4-(1,1-dioxidoisothiazolidin-2-yl)benzoyl chloride

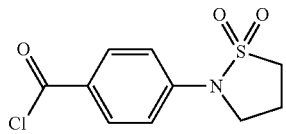 [SMILES: O=C(Cl)c1ccc(N2CCCS2(=O)=O)cc1]

The title compound was prepared by analogy to Preparation T.

Preparation X. 4-(1H-1,2,3-triazol-1-yl)benzoyl chloride

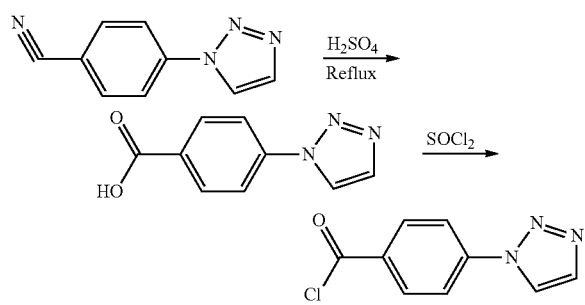

Step X1:

4-(1H-1,2,3-triazol-1-yl)benzonitrile (200 mg, 1.175 mmol, prepared as described in WO 2006/067462 PCT/GB2005/005007 Page 57) in sulfuric acid (3 mL, 0.00 µmol) (50%, 3 ml) was refluxed at 120° C. for 4 h. Cooled down, diluted with water and adjusted pH to 4 with NaOH and Na$_2$CO$_3$, then extracted with ethyl acetate. After the solvent was removed, a white solid was obtained 4-(1H-1,2,3-triazol-1-yl)benzoic acid (180 mg, 0.952 mmol, 81% yield). $^1$H-NMR (DMSO-d6, 500 MHz): δ8.80 (1H, s), 8.13 (2H, d, J=8.55 Hz), 8.01 (2H, d, J=8.55 Hz), 7.98 (1H, s).

Step X2:

The title compound was prepared by analogy to Preparation T.

Preparation Y. 4-(1H-1,2,4-triazol-1-yl)benzoyl chloride

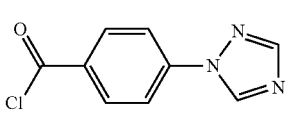 [SMILES: O=C(Cl)c1ccc(-n2cncn2)cc1]

The title compound was prepared by analogy to Preparation T.

Preparation Z.
4-(2,4-dioxoimidazolidin-1-yl)benzoyl chloride

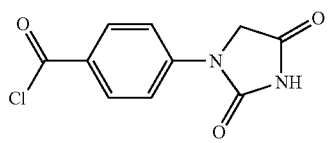 [SMILES: O=C1CN(c2ccc(C(=O)Cl)cc2)C(=O)N1]

The title compound was prepared by analogy to Preparation T.

Preparation AA. 4-(2H-1,2,3-triazol-2-yl)benzoyl chloride

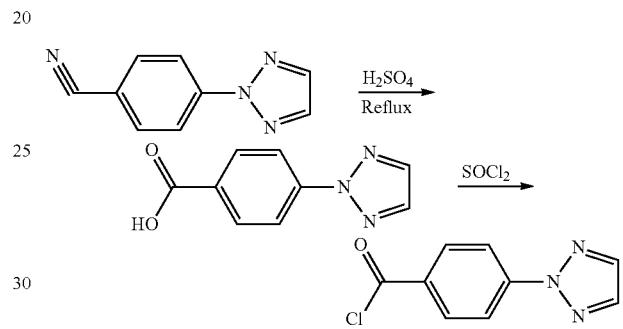

Step AA1:

4-(2H-1,2,3-triazol-2-yl)benzonitrile (170 mg, 0.999 mmol, prepared as described in WO 2006/067462 PCT/GB2005/005007 Page 57) in sulfuric acid (1 g, 5.10 mmol) (50%, 5 ml) was refluxed at 120° C. oil bath for 4 h. Cold down and poured the mixture into water and adjust pH to 3-4 with NaOH and Na$_2$CO$_3$. A white precipitate formed. Extracted with ethyl acetate and drained to give the title compound (170 mg, 0.899 mmol, 90% yield). $^1$H-NMR (CD$_3$OD-d4, 500 MHz): δ8.18 (4H, d, J=1.22 Hz), 7.89 (2H, s).

Step AA2:

The title compound was prepared by analogy to Preparation T.

Preparation AB. 4-(2-oxopyrrolidin-1-yl)benzoyl chloride

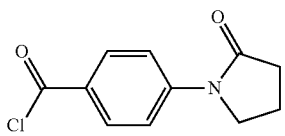 [SMILES: O=C(Cl)c1ccc(N2CCCC2=O)cc1]

To a suspension of 4-(2-oxopyrrolidin-1-yl)benzoic acid (19.94 mg, 0.097 mmol) in DCM (5 ml) was added oxalyl chloride (2M solution in DCM, 0.058 ml, 0.117 mmol) and 2 drops of DMF. The resulting mixture was stirred at r.t for 1 hr., then concentrated in vacuo. The residue (off white solid) was used in subsequent reactions without further purification.

Preparation AC: 4-(6-amino-3,5-dichloropyridin-2-yl)piperazin-1-yl)(3-(2-methoxyphenyl)-5-methyl-isoxazol-4-yl)methanone

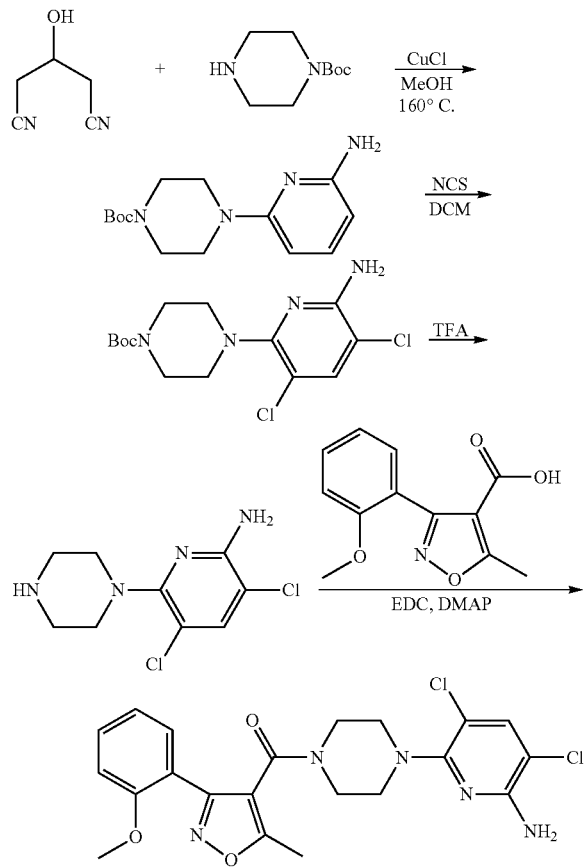

Step AC1:

A mixture of 3-hydroxypentanedinitrile (2555 mg, 23.20 mmol), tert-butyl piperazine-1-carboxylate (4322 mg, 23.20 mmol), and copper(I) chloride (150 mg, 1.515 mmol) in MeOH (9.5 ml) was heated at 160° C. in a sealed tube for 1.5 h. Dilute with MeOH and filtered through a celite to remove the CuCl. The filtration was concentrated and the residue was purified by silicon gel column with DCM, then 3% EtOAC/DCM to give a white solid, tert-butyl 4,4'-(pyridine-2,6-diyl)dipiperazine-1-carboxylate (2.5 g, 5.59 mmol, 24.07% yield). Flashed with 10% EtOAc/DCM to give tert-butyl 4-(6-aminopyridin-2-yl)piperazine-1-carboxylate as an oil. (1.8 g, 6.47 mmol, 27.9% yield). $^1$H-NMR (CD$_3$OD-d4, 500 MHz): δ7.67 (1H, t, J=8.55 Hz), 6.21 (1H, d, J=2.75 Hz), 6.19 (1H, d, J=2.75 Hz), 3.49 (4H, m), 3.31 (4H, m), 1.49 (9H, s).

Step AC2:

A mixture of tert-butyl 4-(6-aminopyridin-2-yl)piperazine-1-carboxylate (320 mg, 1.150 mmol) and NCS (307 mg, 2.299 mmol) in Carbon tetrachloride (10 mL)/CH$_2$Cl$_2$ (5.00 mL) was refluxed at 40° C. for 2 h. Purification on silicon gel column with DCM, then 2% EtOAc in DCM gave tert-butyl 4-(6-amino-3,5-dichloropyridin-2-yl)piperazine-1-carboxylate (110 mg, 0.305 mmol, 26.5% yield). $^1$H-NMR (CDCl$_3$, 500 MHz): δ 7.39 (1H, s), 4.71 (2H, s), 3.53 (4H, m), 3.21 (4H, m), 1.47 (9H, s).

Step AC3:

tert-butyl 4-(6-amino-3,5-dichloropyridin-2-yl)piperazine-1-carboxylate (110 mg, 0.305 mmol,) was treated with 50% TFA/DCM for 1 h, then drained and dried in vacuum to give 3,5-dichloro-6-(piperazin-1-yl)pyridin-2-amine (110 mg, 0.305 mmol). $^1$H-NMR (CD$_3$OD-d4, 500 MHz): δ7.51 (1H, s), 3.51 (4H, m), 3.31 (4H, m).

Step AC4:

A mixture of 3-(2-methoxyphenyl)-5-methylisoxazole-4-carboxylic acid (71.0 mg, 0.305 mmol, Preparation A), 3,5-dichloro-6-(piperazin-1-yl)pyridin-2-amine (110 mg, 0.305 mmol) EDC (76 mg, 0.396 mmol), and DMAP (112 mg, 0.914 mmol) in DCM (2 mL) was stirred for 3 h at RT. HPLC purification gave the title compound (91 mg, 0.193 mmol, white solid, 63.3% yield). $^1$H-NMR (CDCl$_3$, 500 MHz): δ 7.58 (1H, d, J=7.53 Hz), 7.46 (1H, t, J=7.53 Hz), 7.43 (1H, s), 7.06 (1H, t, J=7.53 Hz), 6.99 (1H, d, J=8.28 Hz), 3.80 (3H, s), 3.78 (2H, m), 3.23 (4H, m), 2.72 (2H, s), 2.56 (3H, s).

Preparation AD: (4-(5-amino-2-chloro-4-methylphenyl)piperazin-1-yl)(3-(2-methoxyphenyl)-5-methyl-isoxazol-4-yl)methanone

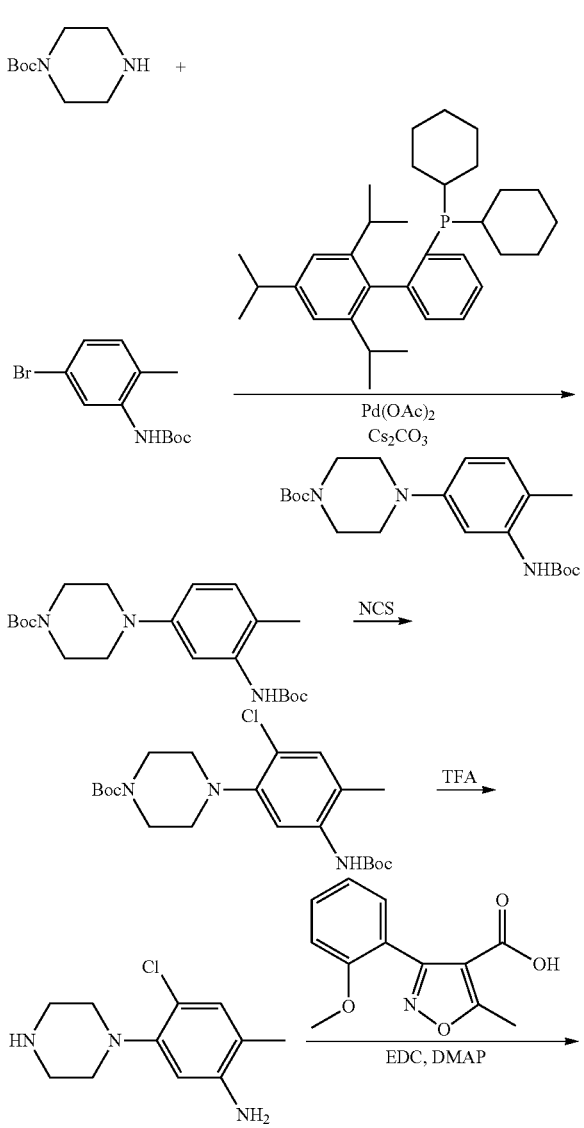

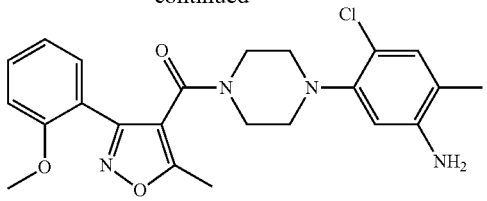

Step AD1:
A mixture of tert-butyl piperazine-1-carboxylate (5.47 g, 29.4 mmol), tert-butyl 5-bromo-2-methylphenylcarbamate (2.8 g, 9.78 mmol), dicyclohexyl(2',4',6'-triisopropylbiphenyl-2-yl)phosphine (0.233 g, 0.489 mmol), diacetoxypalladium (0.066 g, 0.294 mmol), and Reactant 5 (9.56 g, 29.4 mmol) (Cs$_2$CO$_3$) in Toluene (45 mL) was heated at 100-110° C. for 2 days. After the solvent was removed, the residue was dissolved in ethyl acetate and washed with water. After the EtOAc was removed, the residue was purified by column with DCM, then EtOAc/DCM (2%) to give tert-butyl 4-(3-(tert-butoxycarbonylamino)-4-methylphenyl)piperazine-1-carboxylate (2.5 g, 6.39 mmol, 65.3% yield, white solid). $^1$H-NMR (CDCl$_3$, 500 MHz): δ 7.57 (1H, s), 7.00 (1H, d, J=8.55 Hz), 6.55 (1H, d, J=8.24 Hz), 6.31 (1H, s), 3.56 (4H, m), 3.09 (4H, m), 2.15 (3H, s), 1.52 (9H, s), 1.48 (9H, s).

Step AD2:
A mixture of tert-butyl 4-(3-(tert-butoxycarbonylamino)-4-methylphenyl)piperazine-1-carboxylate (100 mg, 0.255 mmol) and NCS (37.5 mg, 0.281 mmol) in DCM (2 mL) was stirred overnight. HPLC purification gave tert-butyl 4-(5-(tert-butoxycarbonylamino)-2-chloro-4-methylphenyl)piperazine-1-carboxylate, TFA (100 mg, 0.185 mmol, 72.5% yield). $^1$H-NMR (CDCl$_3$, 500 MHz): δ 7.65 (1H, s), 7.13 (1H, s), 6.32 (1H, s), 3.59 (4H, m), 2.99 (4H, m), 2.16 (3H, s), 1.52 (9H, s), 1.48 (9H, s).

Step AD3:
tert-butyl 4-(5-(tert-butoxycarbonylamino)-2-chloro-4-methylphenyl)piperazine-1-carboxylate, TFA (100 mg, 0.185 mmol) was treated with 50% TFA/DCM for 1 h. After the solvent was removed, the residue was dried in vacuo.

Step AD4:
The title compound was prepared by analogy to Preparation L, substituting the product from Step AD3 for 4-chloro-2-nitro-5-(piperazin-1-yl)aniline. $^1$H-NMR (CDCl$_3$, 500 MHz): δ 8.25 (2H, s), 7.50 (1H, dd, J=7.63 Hz, 1.53 Hz), 7.41 (1H, td, J=8.24 Hz, 1.53 Hz), 7.13 (1H, s), 7.01 (1H, t, J=7.63 Hz), 6.94 (1H, d, J=8.55 Hz), 6.66 (1H, s), 3.77 (2H, s), 3.74 (3H, s), 3.20 (2H, s), 2.85 (2H, s), 2.49 (3H, s), 2.37 (2H, s), 2.15 (3H, s).

Preparation AE. (4-(5-amino-2-bromo-4-methylphenyl)piperazin-1-yl)(3-(2-methoxyphenyl)-5-methylisoxazol-4-yl)methanone

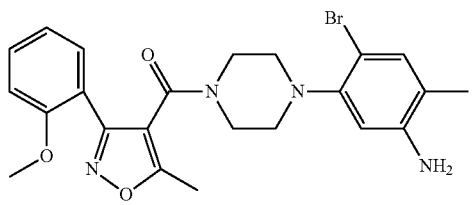 [SMILES: COc1ccccc1-c1noc(C)c1C(=O)N1CCN(c2cc(N)c(C)cc2Br)CC1]

Prepared by analogy to Preparation AD, substituting NBS for NCS in Step AD2. $^1$H-NMR (CDCl$_3$, 500 MHz): δ 8.44 (2H, s), 7.47 (1H, dd, J=7.63 Hz, 1.53 Hz), 7.40 (1H, td, J=8.24 Hz, 1.53 Hz), 7.35 (1H, s), 6.98 (1H, t, J=7.63 Hz), 6.94 (1H, d, J=8.55 Hz), 6.76 (1H, s), 3.74 (2H, s), 3.72 (3H, s), 3.20 (2H, s), 2.83 (2H, s), 2.46 (3H, s), 2.36 (2H, s), 2.16 (3H, s).

Preparation AF. (4-(6-amino-3-chloro-5-nitropyridin-2-yl)piperazin-1-yl)(3-(2-methoxyphenyl)-5-methylisoxazol-4-yl)methanone

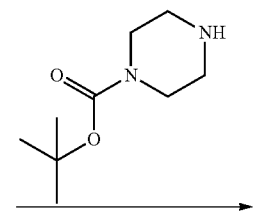

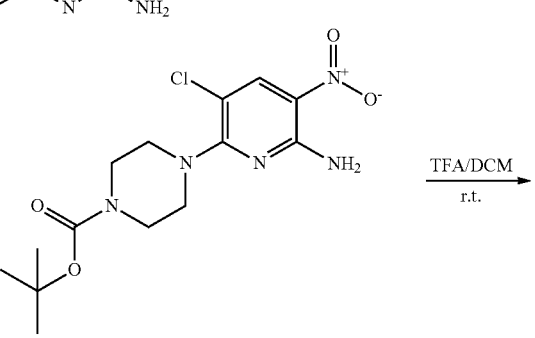

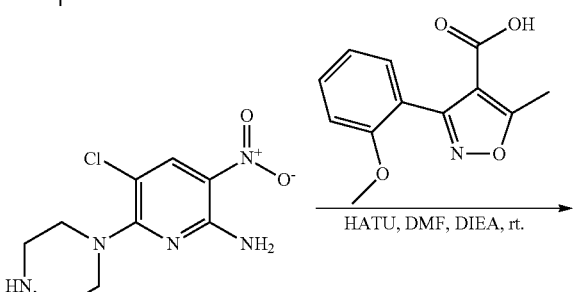

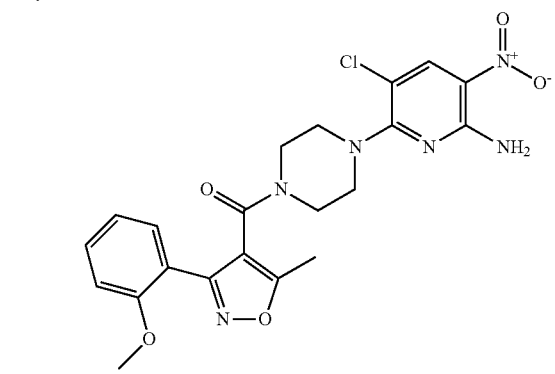

Step AF1:
To a mixture of 5,6-dichloro-3-nitropyridin-2-amine (40 mg, 0.192 mmol, prepared as described in: [Micheli, F.; Cugola, A.; Donati, D.; Missio, A.; Pecunioso, A.; Reggiani, A.; Tarzia, G. *Bioorg. Med. Chem.*, 1997, 5(12), 2129.]) and tert-butyl piperazine-1-carboxylate (43.0 mg, 0.231 mmol) was added CH$_2$Cl$_2$ (5 ml) followed by DIEA (0.050 ml, 0.288 mmol). The reaction mixture was stirred at room temperature for 3 h. The solvent was evaporated under reduced pressure and the product was used directly for next step without further purification. $^1$H NMR (500 MHz, MeOD) δ ppm 8.30 (1H, s), 3.64-3.71 (4H, m), 3.57 (4H, br. s.), 1.50 (9H, s).

Step AF2:

t-Butyl 4-(6-amino-3-chloro-5-nitropyridin-2-yl)piperazine-1-carboxylate (0.192 mmol) was treated with 50% TFA in dichloromethane (2 ml). The reaction mixture was stirred at room temperature for ½ h. The solvent was evaporated and the residue was dried under vacuum pump to give 5-chloro-3-nitro-6-(piperazin-1-yl)pyridin-2-amine, TFA salt. LCMS-Phenomenex Luna C18 3.0×50 mm S10, 0 to 100% B over 2.0 minute gradient, 1 minute hold time, A=10% acetonitrile/90% water/0.1% TFA, B=90% acetonitrile/10% water/0.1% TFA. Flow rate: 4 ml/min. Retention time: 0.630 min, m/e 258.02 (M+1)$^+$.

Step AF3:

To a solution of 5-chloro-3-nitro-6-(piperazin-1-yl)pyridin-2-amine, TFA (0.192 mmol) in DMF (2 ml) was added DIEA (0.134 ml, 0.768 mmol), 3-(2-methoxyphenyl)-5-methylisoxazole-4-carboxylic acid (44.8 mg, 0.192 mmol) and HATU (73.0 mg, 0.192 mmol). The reaction was stirred at room temperature for 1 h. The reaction mixture was purified by preparative HPLC to afford 69 mg (73.7% for 3 steps) of the title compound. $^1$H NMR (500 MHz, CDCl$_3$) δ ppm 8.25 (1H, s), 7.58 (1H, dd, J=7.5, 1.7 Hz), 7.52-7.39 (1H, m), 7.08-7.06 (1H, m), 6.97 (1H, d, J=7.9 Hz), 3.79 (3 H, s), 3.72 (2H, br. s.), 3.55 (2H, br. s.), 3.16 (2H, br. s.), 2.98 (2H, br. s.), 2.55 (3H, s).

Preparation AG. 4-amino-2-(4-(3-(2-methoxyphenyl)-5-methylisoxazole-4-carbonyl)piperazin-1-yl)-5-nitrobenzonitrile

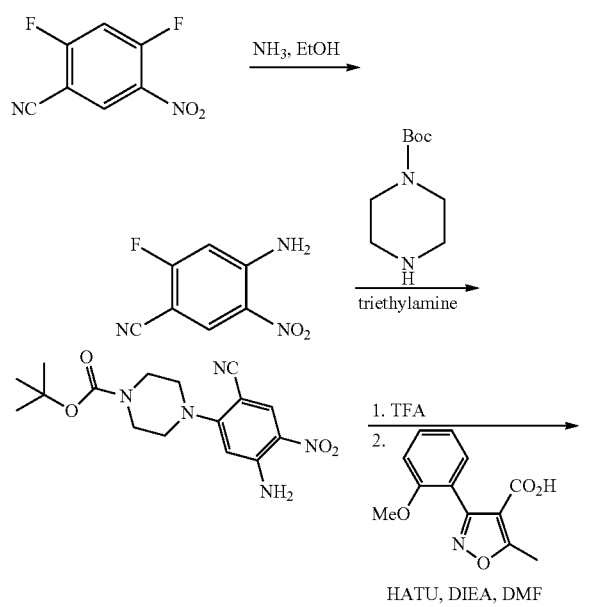

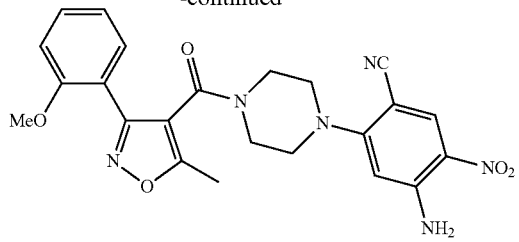

Step AG1:

To a mixture of 2,4-difluoro-5-nitrobenzonitrile (2 g, 10.86 mmol, prepared as described in: [Ohmori, J.; Sakamoto, S. et. al. *J. Med. Chem.*, 1994, 37(4), 467-475.]) in ethanol (1.25 ml) was added ammonia (6.25 mL, 10.86 mmol) at r.t. The mixture was stirred overnight. Filtered to collect the precipitate, washed w/H$_2$O (3×). The solid was dried in vacuo for 24 hrs to afford 1.9 g of 4-amino-2-fluoro-5-nitrobenzonitrile (1.8 g, 9.44 mmol, 87% yield), which was used in the next reaction without further purification. $^1$H-NMR (CD$_3$OD, 500 MHz): δ 8.55 (1H, s), 6.82 (1H, s). m/e (M+H): 182.1.

Step AG2:

To a solution of 4-amino-2-fluoro-5-nitrobenzonitrile (132 mg, 0.730 mmol) and tert-butyl piperazine-1-carboxylate (136 mg, 0.730 mmol) in DMF (3 ml) was added triethylamine (0.102 ml, 0.730 mmol). The mixture was heated to 80° C. in a Microwave reactor for 50 min., cooled to r.t., purified by prep-HPLC to afford tert-butyl 4-(5-amino-2-cyano-4-nitrophenyl)piperazine-1-carboxylate (120 mg, 0.328 mmol, 44.9% yield). $^1$H-NMR (CD$_3$OD, 500 MHz): δ 8.42 (1H, s), 6.45 (1H, s), 3.65-3.61 (4H, m), 3.28-3.25 (4H, m), 1.51 (9H, s). m/e (M+H): 348.3.

Step AG3:

4-amino-5-nitro-2-(piperazin-1-yl)benzonitrile was prepared by analogy to Step AF2 of Preparation AF, substituting t-butyl 4-(5-amino-2-cyano-4-nitrophenyl)piperazine-1-carboxylate for t-butyl 4-(6-amino-3-chloro-5-nitropyridin-2-yl)piperazine-1-carboxylate.

Step AG4:

The title compound was prepared by analogy to Step AF3 of Preparation AF, substituting 4-amino-5-nitro-2-(piperazin-1-yl)benzonitrile for 5-chloro-3-nitro-6-(piperazin-1-yl)pyridin-2-amine $^1$H-NMR (CD$_3$OD, 500 MHz): δ 8.38 (1H, s), 7.57-7.52 (2H, m), 7.17-7.11 (2H, m), 6.27 (1H, s), 3.80 (3H, s), 3.37 (4H, br. S), 3.25-3.19 (4H, m), 2.53 (3H, s). m/e (M+H): 463.1.

Preparation AH. N-(4-chloro-2-nitro-5-(piperazin-1-yl)phenyl)-4-(methylsulfonamido)benzamide

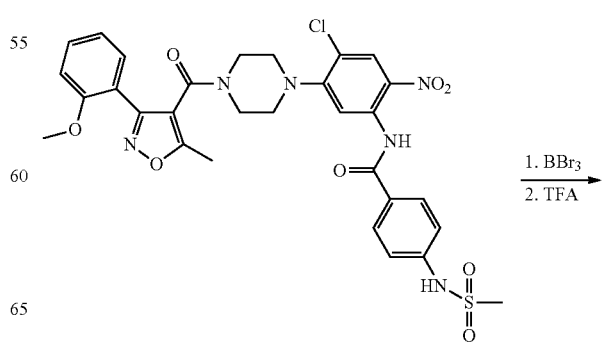

-continued

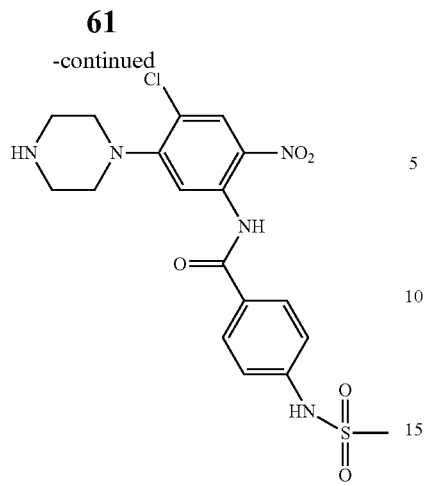

Step AH1:

N-(4-Chloro-5-(4-(3-(2-methoxyphenyl)-5-methylisoxazole-4-carbonyl)piperazin-1-yl)-2-nitrophenyl)-4-(methylsulfonamido)benzamide was prepared as described in Example 50. $^1$H-NMR (CDCl$_3$, 400 MHz) δ 11.56 (1H, s), 8.56 (1H, s), 8.29 (1H, s), 7.99 (2H, d, J=8.8 Hz), 7.59 (1H, dd, J=7.5, 1.8 Hz), 7.45-7.52 (1H, m), 7.36 (2H, d, J=8.5 Hz), 7.19 (1H, s), 7.11 (1H, t, J=7.5 Hz), 7.02 (1H, d, J=8.3 Hz), 3.83 (5H, s), 3.34-3.15 (4H, m), 3.13 (3H, s), 2.59 (5H, s).

Step AH2:

N-(4-Chloro-5-(4-(3-(2-methoxyphenyl)-5-methylisoxazole-4-carbonyl)piperazin-1-yl)-2-nitrophenyl)-4-(methylsulfonamido)benzamide was treated with boron tribromide as described in Example 117. The crude product (140 mg) was treated with 0.8 M trifluoroacetic acid in DCM (4.0 mL) at room temperature overnight. Solvent was evaporated in vacuo and the product was purified by preparative HPLC (0.1% TFA MeOH/H$_2$O) to give 53 mg (55% yield) of the title compound. H$^1$-NMR (500 MHz, CD$_3$OD) δ 8.57 (1H, s), 8.36 (1H, s), 7.98 (2H, d, J=8.9 Hz), 7.41 (2H, d, J=8.9 Hz), 3.48-3.53 (4H, m), 3.42-3.48 (4H, m), 3.08 (3H, s).

Preparation AI. tert-butyl 4-(5-amino-4-bromo-2-chlorophenyl)piperazine-1-carboxylate

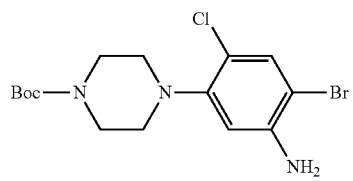 [SMILES: CC(C)(C)OC(=O)N1CCN(c2cc(N)c(Br)cc2Cl)CC1]

To the solution of 2-bromo-4-chloro-5-(piperazin-1-yl)aniline, 3 TFA (128 mg, 0.202 mmol, prepared as described in Step N2 of Preparation N) and DIEA (0.106 mL, 0.607 mmol) in DCM (4.5 mL) was added di-tert-butyl dicarbonate (0.047 mL, 0.202 mmol). The solution was stirred at room temperature for one hour. Solvent was evaporated and the product was purified by flash chromatography (10% ether/DCM, Rf 0.6) to give 55 mg (70% yield).

$^1$H NMR (CDCl$_3$, 400 MHz) δ 7.40 (1H, s), 6.41 (1H, s), 4.05 (2H, br. s.), 3.54-3.63 (4H, m), 2.88-2.98 (4H, m), 1.49 (9H, s).

Preparation AJ. tert-butyl 4-(chlorocarbonyl)phenylcarbamate

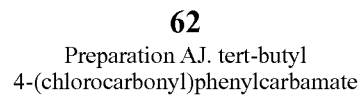

The title compound was prepared by analogy to Preparation AB.

Preparation AK. 4-(2-oxo-1,3-oxazinan-3-yl)benzoyl chloride

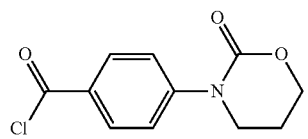 [SMILES: O=C(Cl)c1ccc(N2CCCOC2=O)cc1]

The title compound was prepared by analogy to Preparation AB.

Preparation AL. 4-(2-oxooxazolidin-3-yl)benzoyl chloride

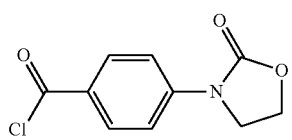

The title compound was prepared by analogy to Preparation AB.

Preparation AM. 4-(dimethylcarbamoyl)benzoyl chloride

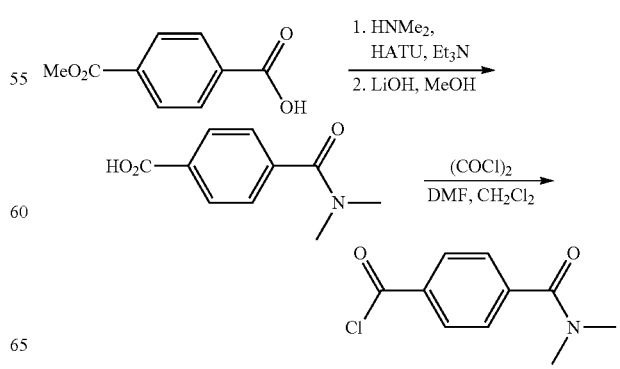

Step AM1:

To a soln. of 4-(methoxycarbonyl)benzoic acid (100 mg, 0.555 mmol) in THF (5 ml) was added HATU (211 mg, 0.555 mmol), dimethylamine (0.278 ml, 0.555 mmol) and triethylamine (0.077 ml, 0.555 mmol) at r.t. The mixture was stirred at r.t for 4 hrs. Evaporated to remove the solvent. The residue was dissolved in EtOAc (10 ml), washed w/water (3×), brine. Dried (Na$_2$SO$_4$), and evaporated to afford methyl 4-(dimethylcarbamoyl)benzoate (100 mg, 0.458 mmol, 83% yield) as solid. $^1$H-NMR (CD$_3$OD, 500 MHz): δ 8.10 (1H, d, J=6.4 Hz), 7.55 (1H, d, J=6.4 Hz), 3.94 (3H, s), 3.13 (3H, s), 2.99 (3H, s). m/e (M+H): 208.1

Step AM2:

To a soln. of methyl 4-(dimethylcarbamoyl)benzoate (100 mg, 0.483 mmol, crude from above preparation) in MeOH (4 ml) was added LiOH (1 ml, 3.00 mmol). The mixture was stirred at r.t for 1.5 hrs. Evaporated to remove the solvent. The residue was dissolved in water (3 ml), neutralized w/6M HCl to PH=3, extracted w/EtOAc (3×). The combined organic layer was dried (Na$_2$SO$_4$) and evaporated to afford 4-(dimethylcarbamoyl)benzoic acid (64 mg, 0.315 mmol, 65.2% yield) as solid, which was used for the next reaction directly.

Step AM3:

The title compound was prepared from the product of Step AM2 by analogy to Preparation AB.

Preparation AN. 4-(2-oxoimidazolidin-1-yl)benzoyl chloride

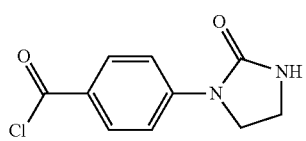 [SMILES: O=C(Cl)c1ccc(N2CCNC2=O)cc1]

The title compound was prepared by analogy to Preparation AB.

Preparation AO.
4-(5-methyl-1,3,4-oxadiazol-2-yl)benzoyl chloride

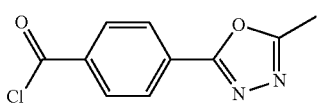

The title compound was prepared by analogy to Preparation T.

Preparation AP. 4-(2-oxopiperidin-1-yl)benzoyl chloride

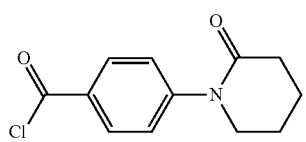 [SMILES: O=C(Cl)c1ccc(N2CCCCC2=O)cc1]

The title compound was prepared by analogy to Preparation AB.

Example 1

N-(4-chloro-5-(4-(3-(2-methoxyphenyl)-5-methylisoxazole-4-carbonyl)piperazin-1-yl)-2-nitrophenyl)-4-methoxybenzamide

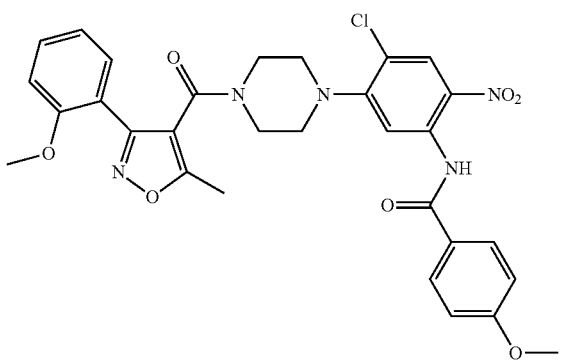

A mixture of (4-(5-amino-2-chloro-4-nitrophenyl)piperazin-1-yl)(3-(2-methoxyphenyl)-5-methylisoxazol-4-yl)methanone (16 mg, 0.034 mmol, Preparation L), 4-methoxybenzoyl chloride (12 mg, 0.068 mmol), DMAP (6 mg, 0.034 mmol), and BEMP (19 mg, 0.068 mmol) in DCE (1 mL) was heated at 80° C. for 3 h. Cooled down to RT, the mixture was treated with piperidine (0.3 ml) for 1 h and concentrated in vacuo. HPLC purification gave the title compound (15.7 mg, 0.025 mmol, 74.9% yield).

$^1$H-NMR (CDCl$_3$, 500 MHz): δ11.54 (1H, s), 8.59 (1H, s), 8.28 (1H, s), 7.96 (2H, d, J=8.85 Hz), 7.59 (1H, d, J=7.63 Hz), 7.50 (1H, t, J=8.53 Hz), 7.13 (1H, t, J=8.53 Hz), 7.04 (3H, m), 3.91 (3H, s), 3.83 (2H, s), 3.82 (3H, s), 3.53 (2H, s), 3.27 (2H, s), 3.18 (2H, s), 2.59 (3H, s). HPLC/MS (Method I): (ES+) m/z (M+H)$^+$=606; R$_t$=1.74 min.

Examples 2-40

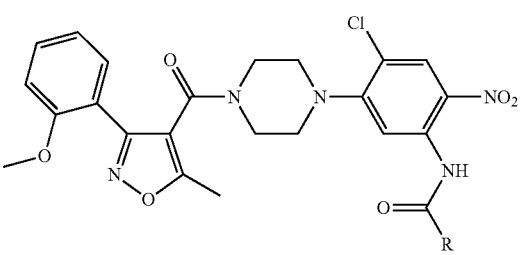

Examples 2-40 were Synthesized by Analogy to Example 1, Substituting the Appropriate Acid Chloride Preparation for 4-Methoxybenzoyl Chloride

| Example | R | Acid Chloride Preparation | MH⁺ | RT | LC/MS Method |
|---|---|---|---|---|---|
| 2 | phenyl | Commercial | 598 (MNa+) | 1.71 | I |
| 3 | 4-chlorophenyl | Commercial | 610 | 1.83 | I |
| 4 | thiophen-2-yl | Commercial | 604 (MNa+) | 1.66 | I |
| 5 | thiazol-2-yl | Commercial | 583 | 1.38 | I |
| 6 | cyclopentyl | Commercial | 568 | 1.48 | I |
| 7 | pyrid-2-yl | Commercial | 577 | 1.42 | I |
| 8 | fur-2-yl | Commercial | 566 | 1.62 | I |
| 9 | cyclobutyl | Commercial | 554 | 1.64 | I |
| 10 | 5-chlorothiophen-2-yl | Commercial | 638 (MNa+) | 1.83 | I |
| 11 | 4-methylthiophenyl | Commercial | 644 (MNa+) | 1.81 | I |
| 12 | cyclopropyl | Commercial | 540 | 1.52 | I |
| 13 | 4-difluoromethoxyphenyl | Commercial | 642 | 1.72 | I |
| 14 | 4-(N,N-dimethylamino)phenyl | Commercial | 641.26 (MNa+) | 1.77 | I |
| 15 | 4-ethoxyphenyl | Commercial | 620 | 1.81 | I |
| 16 | thiophen-3-yl | Commercial | 604 (MNa+) | 1.65 | I |
| 17 | 4-methyl-thiophen-2-yl | Commercial | 596 | 1.77 | I |
| 18 | 5-methylisoxazol-2-yl | Commercial | 603 (MNa+) | 1.63 | I |
| 19 | thiazol-4-yl | Commercial | 583 | 1.57 | I |
| 20 | p-CO2Me-phenyl | Commercial | 656 (MNa+) | 1.68 | I |
| 21 | pyrazin-2-yl | Commercial | 578 | 1.51 | I |
| 22 | 4-cyanophenyl | Commercial | 601 | 1.6 | I |
| 23 | 4-acetamidophenyl | Commercial | 633 | 1.45 | I |
| 24 | 4-methylphenyl | Commercial | 612 (MNa+) | 1.78 | I |
| 25 | 4-ethylphenyl | Commercial | 604 | 1.89 | I |
| 26 | 4-trifluoromethylphenyl | Commercial | 644 | 2.16 | J |
| 27 | 4-nitrophenyl | Commercial | 621 | 1.66 | I |
| 28 | 4-fluorophenyl | Commercial | 594 | 1.7 | I |
| 29 | 5-bromopyrid-2-yl | Commercial | 657 | 2.21 | J |
| 30 | 4-(N,N-diethylamino)phenyl | Commercial | 669 (MNa+) | 1.77 | I |
| 31 | 5-trifluoromethyl pyrid-2-yl | Commercial | 646 | 2.19 | M |
| 32 | 3-fluoro-4-methoxyphenyl | Commercial | 625 | 2.05 | M |
| 33 | 2,4-difluorophenyl | Commercial | 678 | 2.34 | M |
| 34 | 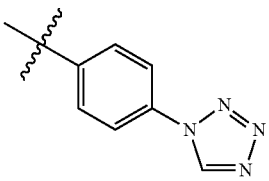 [SMILES: *c1ccc(-n2cnnn2)cc1] | U | 645 | 1.81 | M |
| 35 | 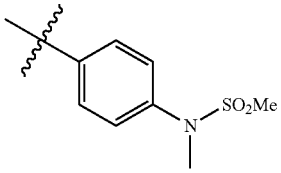 [SMILES: *c1ccc(N(C)S(C)(=O)=O)cc1] | V | 684 | 1.88 | M |

-continued

| Example | R | Acid Chloride Preparation | MH+ | RT | LC/MS Method |
|---|---|---|---|---|---|
| 36 | 4-(2,5-dioxoimidazolidin-1-yl)phenyl | Z | 675 | 1.73 | M |
| 37 | 4-(1H-1,2,4-triazol-1-yl)phenyl | T | 644 | 1.81 | M |
| 38 | 4-(5-methyl-1,3,4-oxadiazol-2-yl)phenyl | AO | 658 | 1.72 | I |
| 39 | benzo[1,3]dioxol-5-yl | Commercial | 620 | 2.09 | J |
| 40 | 4-(1,1-dioxidoisothiazolidin-2-yl)phenyl | W | 695 | 1.91 | M |
| 41 | 4-(2H-1,2,3-triazol-2-yl)phenyl | AA | 643 | 2.17 | J |
| 42 | 4-(1H-1,2,3-triazol-1-yl)phenyl | X | 643 | 1.81 | M |

Examples 43-46

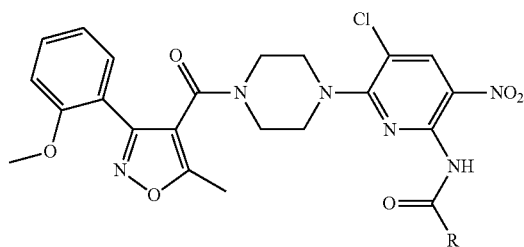

Examples 43-46 were Synthesized by Analogy to Example 1, Substituting Preparation AF for Preparation L, and the Appropriate Acid Chloride Preparation for 4-Methoxybenzoyl Chloride

| Example | R | Acid Chloride Preparation | MH+ | RT | LC/MS Method |
|---|---|---|---|---|---|
| 43 | 4-methoxyphenyl | Commercial | 607 | 2.04 | A |
| 44 | 4-(N,N-dimethylamino)phenyl | Commercial | 620 | 2.11 | A |
| 45 | pyrid-2-yl | Commercial | 578 | 2.88 | N |
| 46 | 4-acetamidophenyl | Commercial | 634 | 1.79 | C |

Example 47

N-(4-chloro-5-(4-(3-(2-methoxyphenyl)-5-methyl-isoxazole-4-carbonyl)piperazin-1-yl)-2-nitrophenyl)-4-(2-oxopyrrolidin-1-yl)benzamide

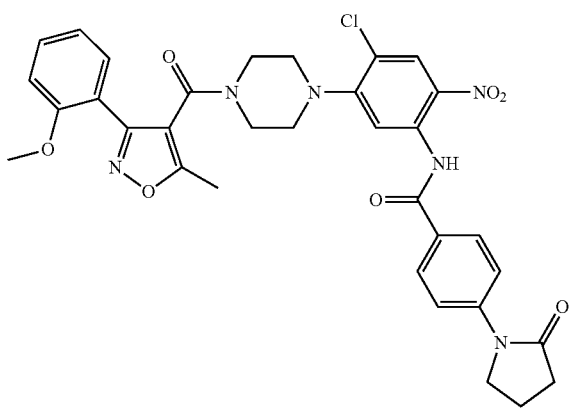 [SMILES: COc1ccccc1-c1noc(C)c1C(=O)N1CCN(c2cc(NC(=O)c3ccc(N4CCCC4=O)cc3)c([N+](=O)[O-])cc2Cl)CC1]

To a soln. of (4-(5-amino-2-chloro-4-nitrophenyl)piperazin-1-yl)(3-(2-methoxyphenyl)-5-methylisoxazol-4-yl)methanone (Preparation L, 27 mg, 0.046 mmol) and 4-(2-oxopyrrolidin-1-yl)benzoic acid (18.91 mg, 0.092 mmol) in acetonitrile (3 ml) was added trichlorophosphine (12.66 mg, 0.092 mmol). The resulting mixture was heated to 150° C. in a Microwave reactor for 50 min. Cooled to room temperature, and quenched with water, evaporated to remove the solvent. The residue was taken up in EtOAc, extracted w/EtOAc (3x). The combined organic layer was dried and evaporated, purified by Pre-HPLC to afford N-(4-chloro-5-(4-(3-(2-methoxyphenyl)-5-methylisoxazole-4-carbonyl)piperazin-1-yl)-2-nitrophenyl)-4-(2-oxopyrrolidin-1-yl)benzamide, TFA (7.8 mg, 9.58 μmol, 20.80% yield). $^1$H-NMR (500 MHz, CD3OD), δ: 11.59 (s, 1H), 8.60 (s, 1H), 8.31 (s, 1H), 8.04 (d, J=9 Hz, 2H), 7.81-7.94 (m, 2H), 7.61 (dd, J=7.5, 1.8 Hz, 1H), 7.51 (td, J=7.9, 1.8 Hz, 1H), 7.14 (t, J=7.5 Hz, 1H), 7.04 (d, J=8.0 Hz, 1H), 3.98 (t, J=7.2 Hz, 2H), 3.84 (s, 3H), 3.35-3.21 (m, 8H), 2.76 (t, J=8.2 Hz, 2H), 2.60 (s, 3H), 2.31-2.23 (m, 2H). HPLC/MS (Method F): (ES+) m/z (M+H)$^+$=659; R$_t$=3.42 min.

Example 48

N-(4-chloro-5-(4-(3-(2-methoxyphenyl)-5-methyl-isoxazole-4-carbonyl)piperazin-1-yl)-2-nitrophenyl)-4-(pyrrolidin-1-yl)benzamide

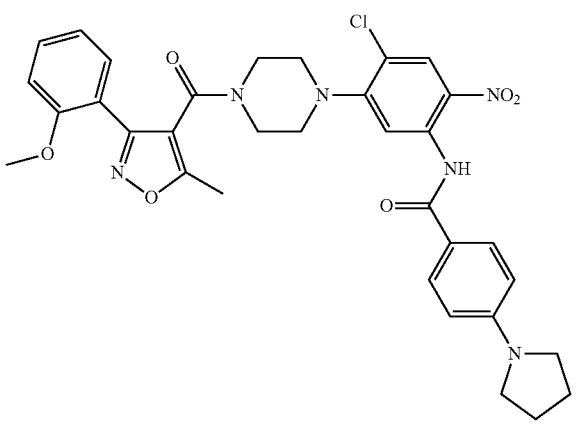 [SMILES: COc1ccccc1-c1noc(C)c1C(=O)N1CCN(c2cc(NC(=O)c3ccc(N4CCCC4)cc3)c([N+](=O)[O-])cc2Cl)CC1]

Example 48 was synthesized by analogy to Example 47, substituting 4-(pyrrolidin-1-yl)benzoic acid for 4-(2-oxopyrrolidin-1-yl)benzoic acid. HPLC/MS (Method D): (ES+) m/z (M+H)$^+$=645; R$_t$=2.12 min.

Example 49

N-(4-chloro-5-(4-(3-(2-methoxyphenyl)-5-methyl-isoxazole-4-carbonyl)piperazin-1-yl)-2-nitrophenyl)-4-(2,5-dioxopyrrolidin-1-yl)benzamide

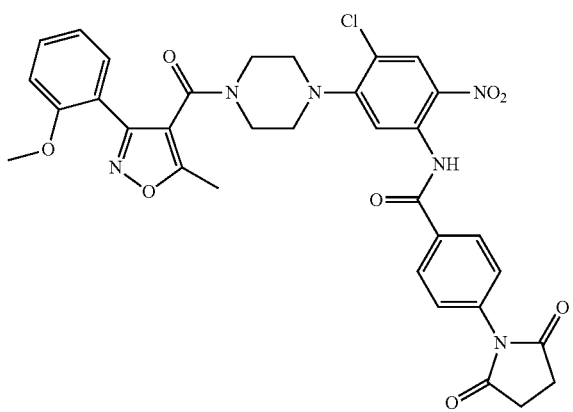 [SMILES: COc1ccccc1-c1noc(C)c1C(=O)N1CCN(c2cc(NC(=O)c3ccc(N4C(=O)CCC4=O)cc3)c([N+](=O)[O-])cc2Cl)CC1]

Example 49 was synthesized by analogy to Example 47, substituting 4-(2,5-dioxopyrrolidin-1-yl)benzoic acid for 4-(2-oxopyrrolidin-1-yl)benzoic acid. HPLC/MS (Method D): (ES+) m/z (M+H)$^+$=673; $R_t$=1.71 min.

Example 50

N-(4-chloro-5-(4-(3-(2-methoxyphenyl)-5-methyl-isoxazole-4-carbonyl)piperazin-1-yl)-2-nitrophenyl)-4-(methylsulfonamido)benzamide

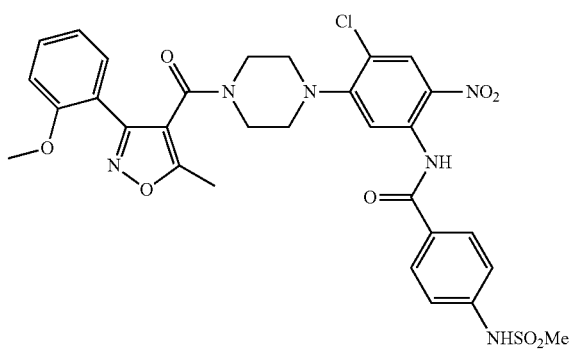

Example 50 was synthesized by analogy to Example 47, substituting 4-(methylsulfonamido)benzoic acid for 4-(2-oxopyrrolidin-1-yl)benzoic acid. HPLC/MS (Method H): (ES+) m/z (M+H)$^+$=669; $R_t$=1.87 min.

Examples 51-68

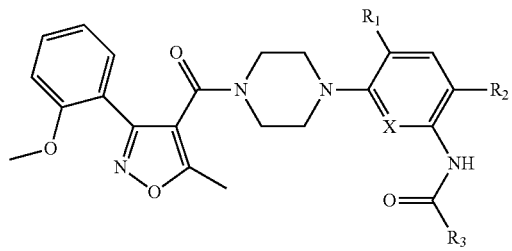

Examples 51-68 were Synthesized by Analogy to Example 1, Substituting the Appropriate Amine Preparation for Preparation L and the Appropriate Acid Chloride Preparation for 4-Methoxybenzoyl Chloride

| Example | X | $R_1$ | $R_2$ | $R_3$ | Amine Preparation | Acid Chloride Preparation | MH$^+$ | RT | LC/MS Method |
|---|---|---|---|---|---|---|---|---|---|
| 51 | N | Cl | Cl | thiazol-2-yl | AC | Commercial | 573 | 1.53 | I |
| 52 | N | Cl | Cl | 4-(N,N-dimethylamino)phenyl | AC | Commercial | 631 (MNa+) | 1.43 | I |
| 53 | CH | Cl | CH$_3$ | 4-(N,N-dimethylamino)phenyl | AD | Commercial | 588 | 1.85 | M |
| 54 | CH | Br | CH$_3$ | 4-(N,N-dimethylamino)phenyl | AE | Commercial | 632, 634 | 1.91 | J |
| 55 | CH | Cl | Cl | 4-(N,N-dimethylamino)phenyl | M | Commercial | 608 | 2.35 | G |
| 56 | CH | Cl | Cl | thiazol-2-yl | M | Commercial | 572 | 2.80 | B |
| 57 | CH | Cl | Cl | 4-(acetamido)phenyl | M | Commercial | 622 | 2.16 | B |
| 58 | CH | Cl | Br | 4-(N,N-dimethylamino)phenyl | N | Commercial | 652 | 2.04 | H |
| 59 | CH | Cl | Br | phenyl | N | Commercial | 609 | 1.50 | K |
| 60 | CH | Cl | Br | 4-methoxyphenyl | N | Commercial | 639 | 2.77 | E |
| 61 | CH | Cl | Br | 4-ethoxyphenyl | N | Commercial | 653 | 2.86 | E |
| 62 | CH | Cl | Br | thiazol-2-yl | N | Commercial | 616 | 3.66 | L |
| 63 | CH | Cl | Br | fur-2-yl | N | Commercial | 599 | 3.42 | L |
| 64 | CH | Cl | Br | 4-acetamidophenyl | N | Commercial | 666 | 1.84 | H |
| 65 | CH | Cl | CN | 4-(N,N-dimethylamino)phenyl | P | Commercial | 599 | 1.85 | H |
| 66 | CH | CN | Cl | 4-methoxyphenyl | R | Commercial | 586 | 1.88 | H |
| 67 | CH | Cl | CN | 4-(2-oxopyrrolidin-1-yl)phenyl | P | AB | 639 | 1.71 | H |
| 68 | CH | CN | NO$_2$ | 4-(N,N-dimethylamino)phenyl | AG | Commercial | 610 | 1.92 | L |

Example 69

N-(2,4-dichloro-5-(4-(5-(fluoromethyl)-3-(2-methoxyphenyl)isoxazole-4-carbonyl)piperazin-1-yl)phenyl)-4-(dimethylamino)benzamide

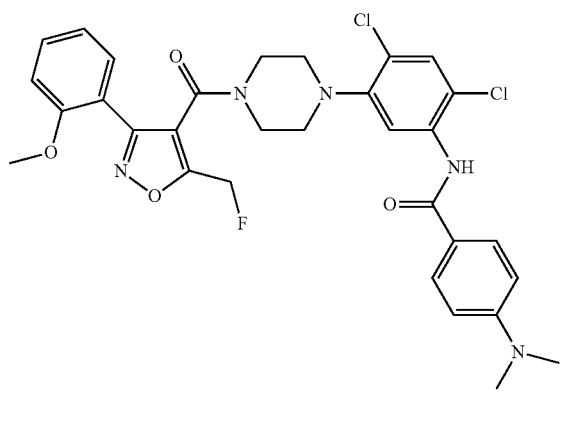

Example 69 was synthesized by analogy to Example 1, substituting Preparation Q for Preparation L and 4-(N,N-dimethylamino)benzoyl chloride for 4-methoxybenzoyl chloride. HPLC/MS (Method H): (ES+) m/z (M+H)$^+$=626; R$_t$=2.02 min.

Example 70

N-(4-chloro-5-(4-(3-(2-methoxyphenyl)-5-methyl-1H-pyrazole-4-carbonyl)piperazin-1-yl)-2-nitrophenyl)-4-(dimethylamino)benzamide

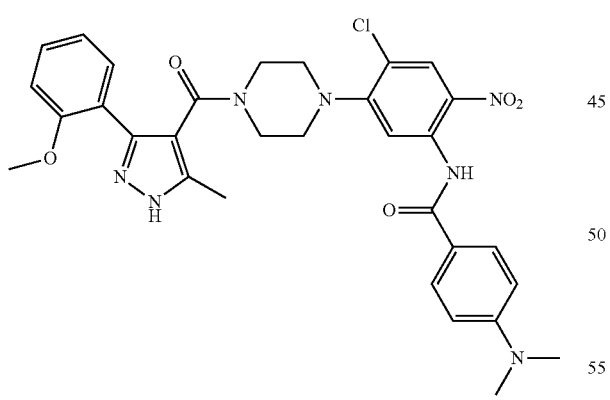

To a solution of N-(4-chloro-2-nitro-5-(piperazin-1-yl)phenyl)-4-(dimethylamino)benzamide, 2 TFA (Preparation D, 35 mg, 0.055 mmol) in DMF (2 ml) was added 3-(2-methoxyphenyl)-5-methyl-1H-pyrazole-4-carboxylic acid (Preparation O, 15.44 mg, 0.066 mmol), HATU (25.3 mg, 0.066 mmol), followed by DIEA (0.048 ml, 0.277 mmol). The reaction was stirred at r.t. for 10 mins. Purified by prep-HPLC to afford 14 mg (33%) of the title compound. HPLC/MS (Method SZ6): (ES+) m/z (M+H)$^+$=618; R$_t$=2.98 min.

Examples 71-76

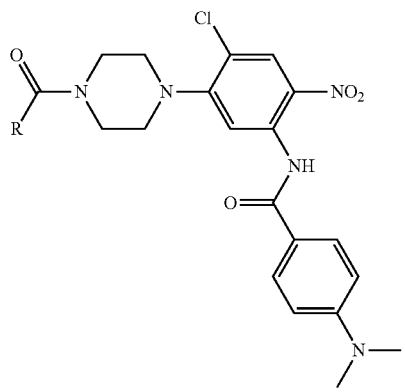

Examples 71-76 were Prepared by Analogy to Example 70, Substituting the Appropriate Heterocycle Preparation for Preparation D

| Example | R | Heterocycle Preparation | MH$^+$ | RT | LC/MS Method |
|---------|---|---|---|---|---|
| 71 | 2-chlorophenyl-3-methyl-1H-pyrazol-4-yl | E | 622 | 3.07 | E |
| 72 | 2-chlorophenyl-4-methyl-1H-pyrrol-3-yl | F | 621 | 3.18 | E |
| 73 | 1-(2-methoxyphenyl)-4-methyl-1H-pyrazol-5-yl | G | 618 | 2.11 | D |
| 74 | 4-phenyl-1-methyl-1H-1,2,3-triazol-5-yl | Commercial | 589 | 2.09 | D |

75

-continued

| Example | R | Heterocycle Preparation | MH+ | RT | LC/MS Method |
|---|---|---|---|---|---|
| 75 | | J | 620 | 3.69 | F |
| 76 | | C | 653 | 2.54 | G |

Example 77

N-(4-chloro-5-(4-(5-methyl-3-(naphthalen-1-yl)isoxazole-4-carbonyl)piperazin-1-yl)-2-nitrophenyl)-4-methoxybenzamide

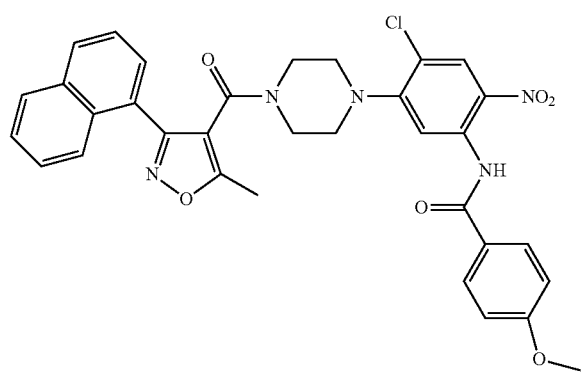 [SMILES: COc1ccc(C(=O)Nc2cc(N3CCN(C(=O)c4c(-c5cccc6ccccc56)noc4C)CC3)c(Cl)cc2[N+](=O)[O-])cc1]

Step 77A (4-(5-amino-2-chloro-4-nitrophenyl)piperazin-1-yl)(5-methyl-3-(naphthalen-1-yl)isoxazol-4-yl)methanone

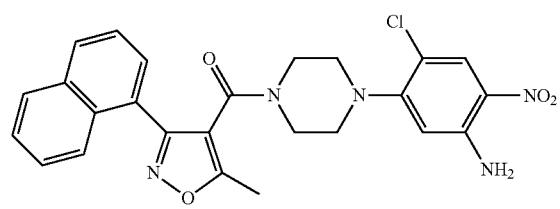 [SMILES: Cc1onc(-c2cccc3ccccc23)c1C(=O)N1CCN(c2cc(N)c([N+](=O)[O-])cc2Cl)CC1]

A mixture of 3-(1-naphthyl)-5-methylisoxazole-4-carboxylic acid (394 mg, 1.558 mmol), 4-chloro-2-nitro-5-(piperazin-1-yl)aniline (400 mg, 1.558 mmol, prepared as described in [El-Abadelah, M. M.; Nazer, M. Z.; El-Abadla, N. S.; Awadallah, A. M. *Asian Journal of Chemistry* 1999, 11(4), 1463-1468.]), EDC (448 mg, 2.337 mmol), and DMAP (571 mg, 4.67 mmol) in DCM (5 mL)/DMF (3 mL) was stirred overnight.

Step 77B

Example 77 was synthesized by analogy to Example 1, substituting the product from Step 77A for Preparation L. HPLC/MS (Method J): (ES+) m/z (M+H)+=626; $R_t$=2.22 min.

Example 78

N-(4-chloro-5-(4-(5-methyl-3-(naphthalen-1-yl)isoxazole-4-carbonyl)piperazin-1-yl)-2-nitrophenyl)thiazole-2-carboxamide

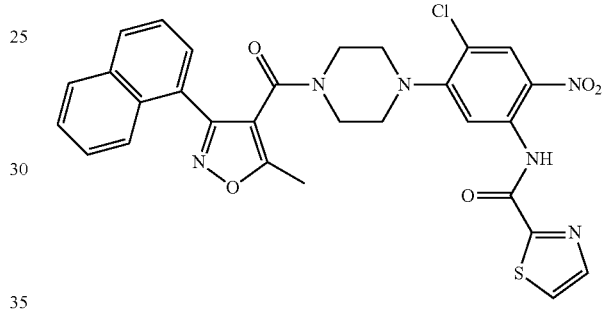

Example 78 was synthesized by analogy to Example 77, substituting thiazole-2-carbonyl chloride for p-methoxylbenzoyl chloride in Step 77B. HPLC/MS (Method J): (ES+) m/z (M+H)+=603; $R_t$=2.16 min.

Example 79

N-(4-chloro-5-(4-(3-(4-fluorophenyl)-5-methylisoxazole-4-carbonyl)piperazin-1-yl)-2-nitrophenyl)-4-(dimethylamino)benzamide

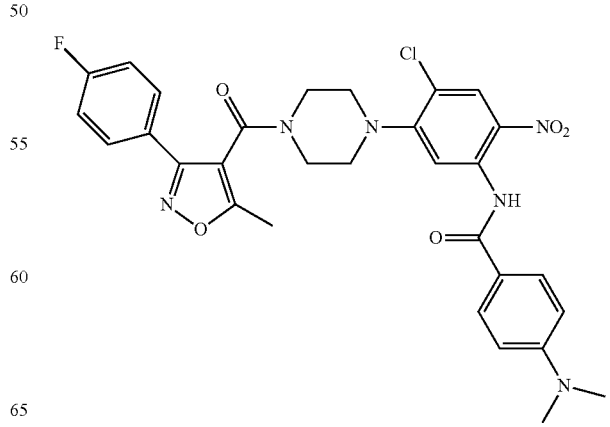

Step 79A (4-(5-amino-2-chloro-4-nitrophenyl)piperazin-1-yl)(3-(4-fluorophenyl)-5-methylisoxazol-4-yl)methanone

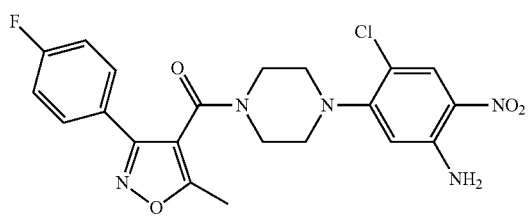 [SMILES: Cc1onc(-c2ccc(F)cc2)c1C(=O)N1CCN(c2cc(N)c([N+](=O)[O-])cc2Cl)CC1]

Step 79A was performed by analogy to Step 77A, substituting 3-(4-fluorophenyl)-5-methylisoxazole-4-carboxylic acid for 3-(1-naphthyl)-5-methylisoxazole-4-carboxylic acid.

Step 79B

Example 79 was synthesized by analogy to Example 1, substituting the product from Step 79A for Preparation L and 4-(N,N-dimethylamino)benzoyl chloride for p-methoxybenzoyl chloride. HPLC/MS (Method I): (ES+) m/z (M+Na)$^+$= 629; $R_t$=1.82 min.

Examples 80-83

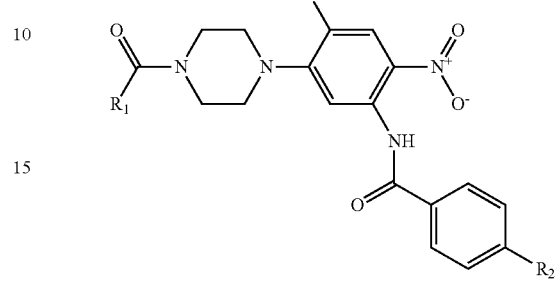

Examples 80-83 were Synthesized by Analogy to Example 79, Substituting the Appropriate Heterocycle Preparation for 3-(4-fluorophenyl)-5-methylisoxazole-4-carboxylic acid and the Appropriate Commercially Available Acid Chloride for 4-(N,N-dimethylamino)benzoyl chloride

| Example | R$_1$ | R$_2$ | Heterocycle Preparation | MH$^+$ | RT | LC/MS Method |
|---|---|---|---|---|---|---|
| 80 | 2-fluorophenyl-1-methylimidazolyl | N,N-dimethylamino | I | 606 | 2.07 | D |
| 81 | 2-methoxyphenyl-1-methylimidazolyl | N,N-dimethylamino | H | 618 | 1.79 | J |
| 82 | 2-methoxyphenyl-methylpyrazolyl | methoxy | D | 605 | 3.27 | F |
| 83 | 2-methoxyphenyl-methylpyrazolyl | acetamido | D | 632 | 2.78 | F |

Example 84

N-(4-chloro-5-(4-(4-(2-methoxyphenyl)-1-methyl-1H-1,2,3-triazole-5-carbonyl)piperazin-1-yl)-2-nitrophenyl)-4-(2-oxopyrrolidin-1-yl)benzamide

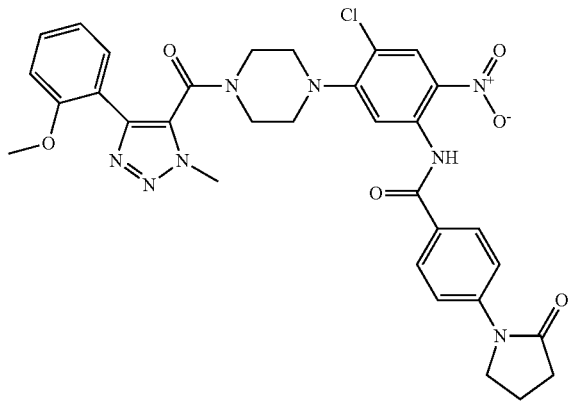 [SMILES: COc1ccccc1-c1nnn(C)c1C(=O)N1CCN(c2cc(NC(=O)c3ccc(N4CCCC4=O)cc3)c([N+](=O)[O-])cc2Cl)CC1]

Step 84A

N-(4-chloro-2-nitro-5-(piperazin-1-yl)phenyl)-4-(2-oxopyrrolidin-1-yl)benzamide

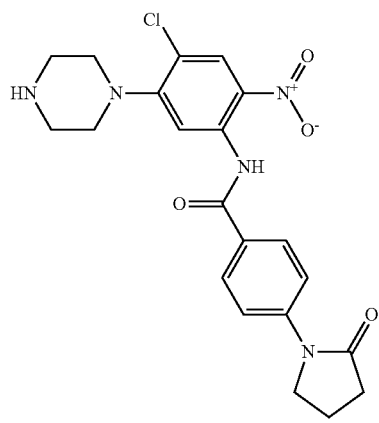 [SMILES: O=C(Nc1cc(N2CCNCC2)c(Cl)cc1[N+](=O)[O-])c1ccc(N2CCCC2=O)cc1]

N-(4-chloro-2-nitro-5-(piperazin-1-yl)phenyl)-4-(2-oxopyrrolidin-1-yl)benzamide was prepared by analogy to Preparation O, substituting Preparation AB for 4-(N,N-dimethylamino)benzoyl chloride.

Step 84B

The title compound was prepared by analogy to Example 70, substituting Preparation J for Preparation D. HPLC/MS (Method F): (ES+) m/z (M+H)$^+$=660; $R_t$=3.24 min.

Examples 85-99

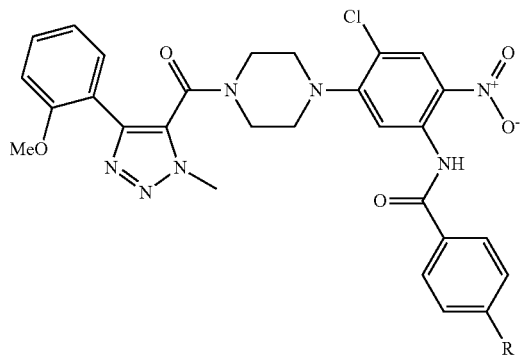

Examples 85-99 were Prepared by Analogy to Example 84, Substituting the Appropriate Acid Chloride Preparation for Preparation AB in Step 84A

| Example | R | Acid Chloride Preparation | MH$^+$ | RT | LC/MS Method |
|---|---|---|---|---|---|
| 85 | methoxy | Commercial | 607 | 3.51 | F |
| 86 | acetamido | Commercial | 648 | 2.99 | F |
| 87 | N(Me)SO$_2$Me | V | 683 | 1.79 | M |
| 88 | N-methylamino | AJ | 605 | 3.38 | F |
| 89 | tetrazolyl | U | 644 | 1.71 | M |
| 90 | tetrahydro-2H-1,3-oxazin-2-one-yl | AK | 675 | 1.76 | D |
| 91 | 1,2,4-triazolyl | T | 643 | 1.87 | J |
| 92 | isothiazolidine-1,1-dioxide | W | 695 | 1.82 | J |
| 93 | oxazolidin-2-one-yl | AL | 661 | 1.81 | D |
| 94 | 1,2,3-triazol-1-yl | AA | 643 | 1.96 | M |
| 95 | 1,2,3-triazol-1-yl | X | 643 | 1.83 | J |
| 96 | C(O)NMe$_2$ | AM | 647 | 2.95 | F |

-continued

| Example | R | Acid Chloride Preparation | MH+ | RT | LC/MS Method |
|---|---|---|---|---|---|
| 97 | 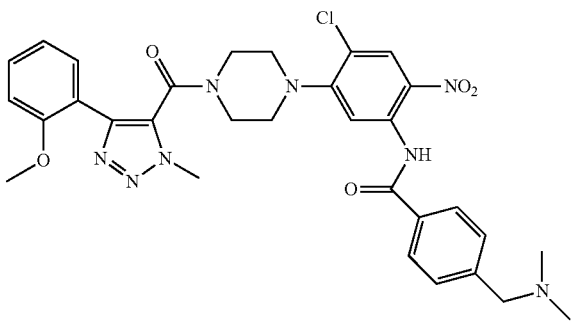 | AN | 660 | 2.98 | F |

Example 98

N-(4-chloro-5-(4-(4-(2-methoxyphenyl)-1-methyl-1H-1,2,3-triazole-5-carbonyl)piperazin-1-yl)-2-nitrophenyl)-4-((dimethylamino)methyl)benzamide

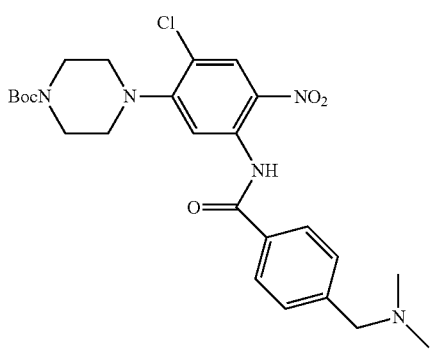 [SMILES: CN(C)Cc1ccc(C(=O)Nc2cc(N3CCN(C(=O)OC(C)(C)C)CC3)c(Cl)cc2[N+](=O)[O-])cc1]

Step 98A tert-butyl 4-(2-chloro-5-(4-((dimethylamino)methyl)benzamido)-4-nitrophenyl)piperazine-1-carboxylate A mixture of tert-butyl 4-(5-amino-2-chloro-4-nitrophenyl)piperazine-1-carboxylate (100 mg, 0.280 mmol), 4-(chloromethyl)benzoyl chloride (106 mg, 0.561 mmol), BEMP (154 mg, 0.561 mmol), and DMAP (34 mg, 0.28 mmol) in acetonitrile (2 mL) was heated overnight at 80° C. Cooled down, treated with 0.5 ml of dimethylamine in water (40%) for 2 h. HPLC purification gave tert-butyl 4-(2-chloro-5-(4-((dimethylamino)methyl)benzamido)-4-nitrophenyl)piperazine-1-carboxylate (94 mg, 0.165 mmol).

Step 98B

N-(4-chloro-2-nitro-5-(piperazin-1-yl)phenyl)-4-((dimethylamino)methyl)benzamide

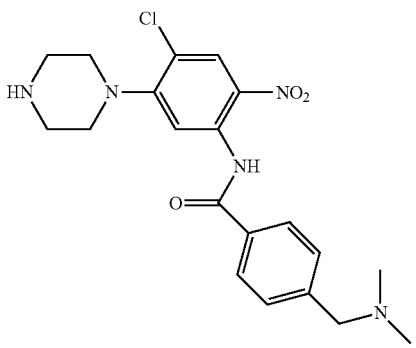 [SMILES: CN(C)Cc1ccc(C(=O)Nc2cc(N3CCNCC3)c(Cl)cc2[N+](=O)[O-])cc1]

tert-butyl 4-(2-chloro-5-(4-((dimethylamino)methyl)benzamido)-4-nitrophenyl)piperazine-1-carboxylate was stirred in TFA/DCM (50%) for 1 h. After solvent was removed, the residue was dried in vacuo overnight.

Step 98C

A mixture of 4-(2-methoxyphenyl)-1-methyl-1H-1,2,3-triazole-5-carboxylic acid (44.7 mg, 0.192 mmol), N-(4-chloro-2-nitro-5-(piperazin-1-yl)phenyl)-4-((dimethylamino)methyl)benzamide (85 mg, 0.160 mmol), HATU (79 mg, 0.208 mmol), and DMAP (78 mg, 0.639 mmol) in NMP (2 mL) was stirred for 3 h. HPLC purification, then silica column purification afforded the title compound (28 mg, 0.041 mmol). $^1$H-NMR (CDCl$_3$, 500 MHz): δ11.62 (1H, s), 8.57 (1H, s), 8.31 (1H, s), 8.06 (2H, d, J=8.24 Hz), 7.81 (1H, d, J=7.24 Hz), 7.69 (2H, d, J=7.93 Hz), 7.43 (1H, t, J=8.24 Hz), 7.13 (1H, t, J=7.32 Hz), 7.01 (1H, d, J=7.24 Hz), 4.28 (2H, s), 4.20 (2H, s), 3.94 (2H, m), 3.83 (3H, s), 3.25 (4H, s), 2.83 (6H, s), 2.68 (2H, m). HPLC/MS (Method J): (ES+) m/z (M+H)$^+$=633; R$_t$=1.52 min.

Example 99

4-(azetidin-1-ylmethyl)-N-(4-chloro-5-(4-(4-(2-methoxyphenyl)-1-methyl-1H-1,2,3-triazole-5-carbonyl)piperazin-1-yl)-2-nitrophenyl)benzamide

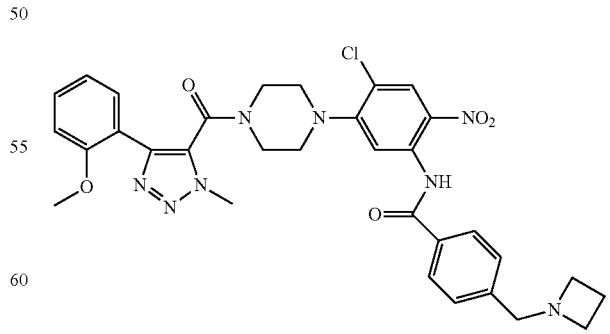

The title compound was synthesized by analogy to Example 98, substituting azetidine for dimethylamine in Step 98A. HPLC/MS (Method M): (ES+) m/z (M+H)$^+$=645; R$_t$=1.36 min.

Examples 100-106

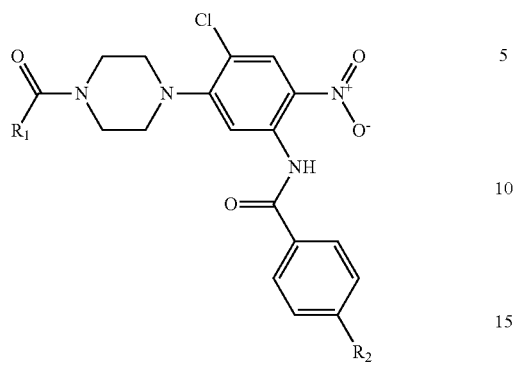

Examples 100-106 were Prepared by Analogy to Example 84, Substituting the Appropriate Acid Chloride Preparation for Preparation AB and the Appropriate Heterocycle Preparation for Preparation J

| Example | R₁ | R₂ | Heterocycle Preparation | Acid Chloride Preparation | MH+ | RT | LC/MS Method |
|---|---|---|---|---|---|---|---|
| 100 | 3-(2-methoxyphenyl)-5-methyl-1H-pyrazol-4-yl | pyrrolidin-2-one-1-yl | D | AB | 659 | 2.99 | F |
| 101 | 4-(2-methoxyphenyl)-1-methyl-1H-imidazol-5-yl | pyrrolidin-2-one-1-yl | H | AB | 659 | 2.59 | F |
| 102 | 4-(2-methoxyphenyl)-1-methyl-1H-imidazol-5-yl | methoxy | H | Commercial | 605 | 2.73 | F |
| 103 | 3-(2-chlorophenyl)-5-methyl-1H-pyrazol-4-yl | N,N-dimethylcarbamoyl | E | AM | 650 | 2.86 | F |
| 104 | 3-(2-chlorophenyl)-5-methyl-1H-pyrazol-4-yl | piperidin-2-one-1-yl | E | AP | 676 | 3.01 | F |

-continued

| Example | R₁ | R₂ | Heterocycle Preparation | Acid Chloride Preparation | MH+ | RT | LC/MS Method |
|---|---|---|---|---|---|---|---|
| 105 | 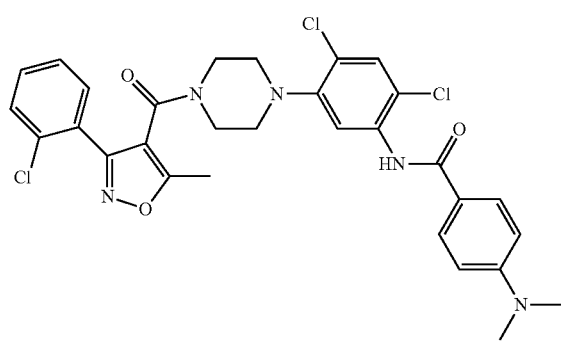 | | E | AB | 662 | 3.14 | F |
| 106 | | | E | U | 647 | 2.16 | J |

Example 107

N-(2,4-dichloro-5-(4-(3-(2-chlorophenyl)-5-methyl-isoxazole-4-carbonyl)piperazin-1-yl)phenyl)-4-(dimethylamino)benzamide

Step 107A

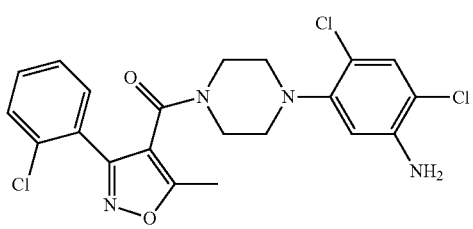 [SMILES: Cc1onc(-c2ccccc2Cl)c1C(=O)N1CCN(c2cc(N)c(Cl)cc2Cl)CC1]

(4-(5-amino-2,4-dichlorophenyl)piperazin-1-yl)(3-(2-chlorophenyl)-5-methylisoxazol-4-yl)methanone was prepared by analogy to Preparation M, substituting 3-(2-chlorophenyl)-5-methylisoxazole-4-carboxylic acid for 3-(2-methoxyphenyl)-5-methylisoxazole-4-carboxylic acid in Step M5.

Step 107B

The title compound was prepared by analogy to Example 1, substituting N,N-dimethylaminobenzoyl chloride for p-methoxybenzoyl chloride.

$^1$H-NMR (CD$_3$OD, 400 MHz) δ 7.89 (2H, d, J=9.0 Hz), 7.59-7.63 (1H, m), 7.46-7.58 (5H, m), 6.87 (2H, d, J=9.0 Hz), 3.74 (2H, br. s.), 3.40 (2H, br. s.), 3.09 (6H, s), 2.93 (2H, br. s.), 2.58 (3H, s), 2.43 (2H, br. s.). HPLC/MS (Method H): (ES+) m/z (M+Na)$^+$=612; R$_t$=2.12 min.

Example 108

N-(4-chloro-5-(4-(3-(2-methoxyphenyl)-5-methyl-isoxazole-4-carbonyl)piperazin-1-yl)-2-nitrophenyl)-4-((dimethylamino)methyl)benzamide

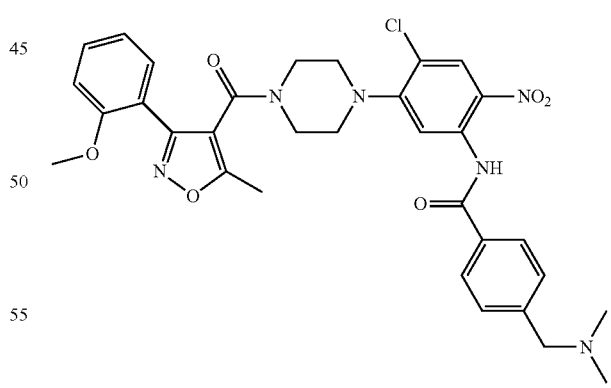

A mixture of Preparation L (20 mg, 0.042 mmol), 4-(chloromethyl)benzoyl chloride (16 mg, 0.084 mmol), BEMP (23 mg, 0.084 mmol) and DMAP (5.2 mg, 0.042 mmol) in DCE (1 mL) was heated for 4 h. The mixture was cooled to room temperature, treated with dimethylamine (0.3 mL, 50% in water) and stirred for 3 h. HPLC purification afforded the title compound as its TFA salt (20.6 mg, 0.027 mmol, 64.4% yield). $^1$H-NMR (CD$_3$OD, 500 MHz): δ8.26 (1H, s), 8.25

(1H, s), 8.12 (2H, d, J=8.24 Hz), 7.74 (1H, d, J=8.24 Hz), 7.54 (2H, m), 7.16 (2H, m), 7.04 (3H, m), 4.45 (2H, s), 3.82 (3H, s), 3.80 (2H, s), 3.31 (4H, s), 3.15 (2H, s), 2.91 (6H, s), 2.55 (3H, s). HPLC/MS (Method M): (ES+) m/z (M+H)$^+$=634; R$_t$=1.39 min.

Example 109

N-(4-chloro-5-(4-(3-(2-methoxyphenyl)-5-methyl-isoxazole-4-carbonyl)piperazin-1-yl)-2-nitrophenyl)-4-((methylamino)methyl)benzamide

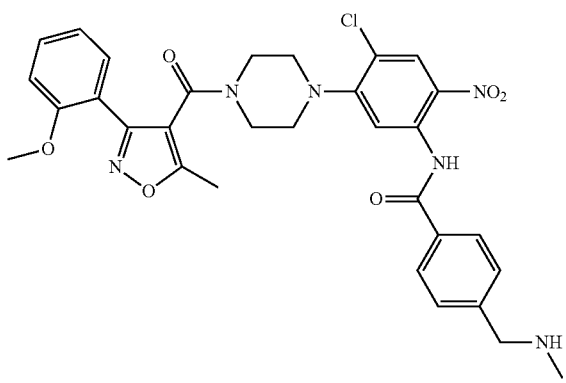

The title compound was prepared by analogy to Example 108, substituting methylamine for dimethylamine HPLC/MS (Method M): (ES+) m/z (M+H)$^+$=619; R$_t$=1.33 min.

Example 110

4-(azetidin-1-yl)-N-(4-chloro-5-(4-(3-(2-methoxyphenyl)-5-methylisoxazole-4-carbonyl)piperazin-1-yl)-2-nitrophenyl)-3-fluorobenzamide

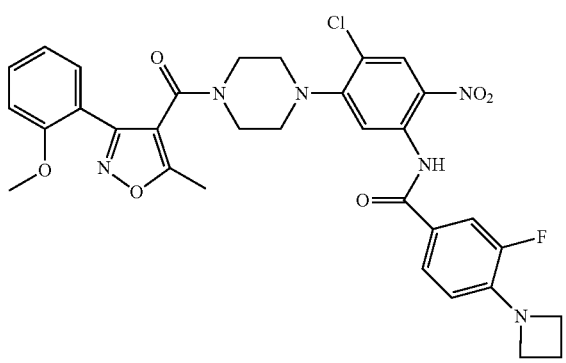 [SMILES: COc1ccccc1-c1noc(C)c1C(=O)N1CCN(c2cc(NC(=O)c3ccc(N4CCC4)c(F)c3)c([N+](=O)[O-])cc2Cl)CC1]

A mixture of Preparation L (12 mg, 0.025 mmol), 3,4-difluorobenzoyl chloride (22.45 mg, 0.127 mmol), BEMP (34.9 mg, 0.127 mmol), and DMAP (3.11 mg, 0.025 mmol) in DCE (1 mL) was heated for 3 h. The reaction mixture was cooled down and treated with azetidine (72.6 mg, 1.271 mmol) overnight. HPLC purification gave the title compound as its TFA salt (4.5 mg, 5.78 μmol, 22.73% yield).

$^1$H-NMR (CDCl$_3$, 500 MHz): δ11.47 (1H, s), 8.56 (1H, s), 8.28 (1H, s), 7.61 (3H, m), 7.50 (1H, t, J=8.85 Hz), 7.13 (1H, t, J=7.32 Hz), 7.03 (1H, d, J=8.24 Hz), 6.47 (1H, t, J=8.85), 4.17 (4H, t, J=9.2 Hz), 3.83 (2H, s), 3.82 (3H, s), 3.35 (2H, s), 3.27 (2H, s), 3.17 (2H, s), 2.59 (3H, s), 2.45 (2H, m). HPLC/MS (Method J): (ES+) m/z (M+H)$^+$=649; R$_t$=2.26 min.

Example 111

N-(4-chloro-5-(4-(3-(2-methoxyphenyl)-5-methyl-isoxazole-4-carbonyl)piperazin-1-yl)-2-nitrophenyl)-4-(dimethylamino)-3-fluorobenzamide

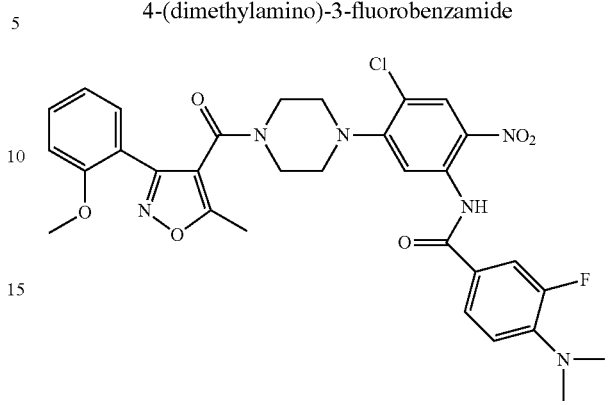

The title compound was prepared by analogy to Example 110, substituting dimethylamine for azetidine. HPLC/MS (Method M): (ES+) m/z (M+H)$^+$=637; R$_t$=2.18 min.

Example 112

N-(4-chloro-5-(4-(3-(2-methoxyphenyl)-5-methyl-isoxazole-4-carbonyl)piperazin-1-yl)-2-nitrophenyl)-4-(dimethylamino)-2,5-difluorobenzamide

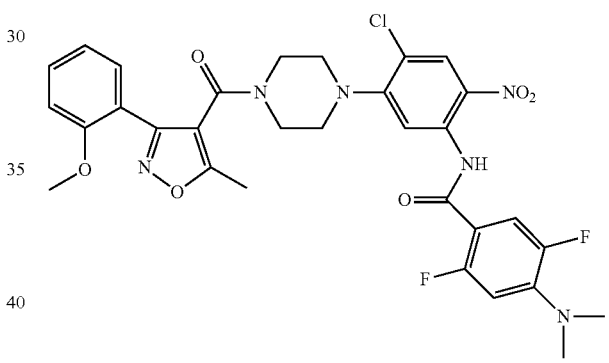

The title compound was prepared by analogy to Example 110, substituting 3,4,6-trifluorobenzoyl chloride for 3,4-difluorobenzoyl chloride and dimethylamine for azetidine. HPLC/MS (Method J): (ES+) m/z (M+H)$^+$=655; R$_t$=2.25 min.

Example 113

N-(4-chloro-5-(4-(3-(2-methoxyphenyl)-5-methyl-isoxazole-4-carbonyl)piperazin-1-yl)-2-nitrophenyl)-2,5-difluoro-4-(methylamino)benzamide

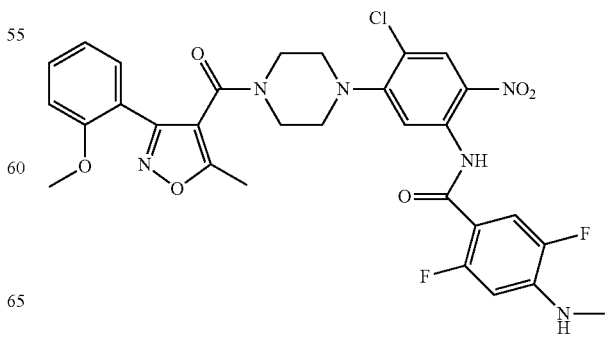

The title compound was prepared by analogy to Example 112, substituting methylamine for dimethylamine HPLC/MS (Method J): (ES+) m/z (M+H)⁺=641; R_t=2.17 min.

Example 114

N-(4-chloro-5-(4-(3-(2-methoxyphenyl)-5-methyl-isoxazole-4-carbonyl)piperazin-1-yl)-2-nitrophenyl)-2,5-difluoro-4-(pyrrolidin-1-yl)benzamide

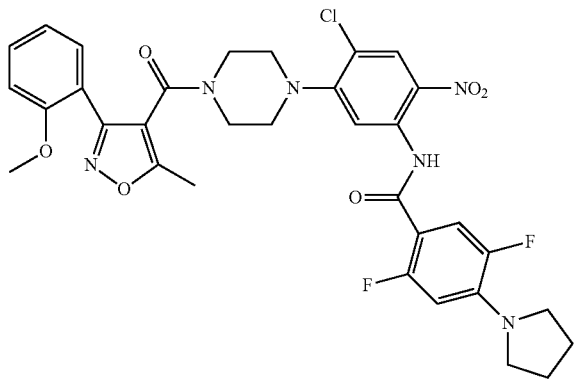 [SMILES: COc1ccccc1-c1noc(C)c1C(=O)N1CCN(c2cc(NC(=O)c3cc(F)c(N4CCCC4)cc3F)c([N+](=O)[O-])cc2Cl)CC1]

The title compound was prepared by analogy to Example 112, substituting Pyrrolidine for dimethylamine. HPLC/MS (Method J): (ES+) m/z (M+H)⁺=681; R_t=2.37 min.

Example 115

N-(4-chloro-2-formyl-5-(4-(3-(2-methoxyphenyl)-5-methylisoxazole-4-carbonyl)piperazin-1-yl)phenyl)-4-(dimethylamino)benzamide

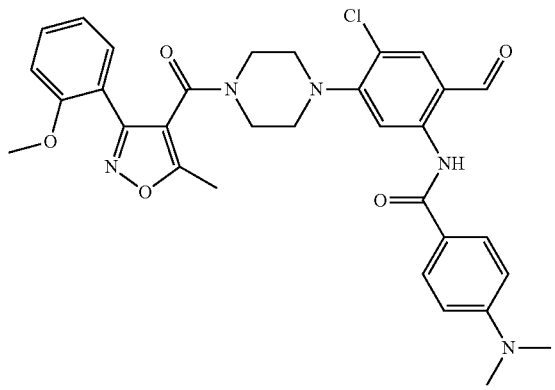

Step 115A

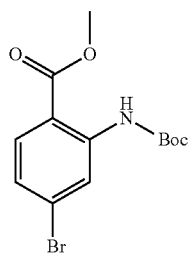 [SMILES: COC(=O)c1ccc(Br)cc1NC(=O)OC(C)(C)C]

Methyl 2-amino-4-bromobenzoate (1.26 g) was Boc-protected as described in Step M1 of Preparation M to give 0.86 g of methyl 4-bromo-2-(tert-butoxycarbonylamino)benzoate. ¹H-NMR (CDCl₃, 400 MHz): δ 10.32 (1H, s), 8.72 (1H, d, J=2.0 Hz), 7.85 (1H, d, J=8.5 Hz), 7.14 (1H, dd, J1=8.5 Hz, J2=2.0 Hz), 3.92 (3H, s), 1.54 (9H, s).

Step 115B

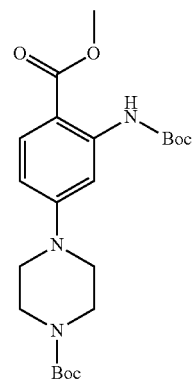 [SMILES: COC(=O)c1ccc(N2CCN(C(=O)OC(C)(C)C)CC2)cc1NC(=O)OC(C)(C)C]

Nitrogen was bubbled into a mixture of methyl 4-bromo-2-(tert-butoxycarbonylamino)benzoate (0.62 g, 1.878 mmol), tert-butyl piperazine-1-carboxylate (0.350 g, 1.878 mmol), dicyclohexyl(2',4',6'-triisopropylbiphenyl-2-yl)phosphine (0.045 g, 0.094 mmol) and cesium carbonate (1.835 g, 5.63 mmol) in toluene (4 mL) for 10 min., followed by the addition of diacetoxypalladium (0.013 g, 0.056 mmol). The reaction mixture was stirred at 110° C. for two hours. The reaction mixture was cooled to RT. Water and ethyl acetate (30 mL/30 mL) were added. The two layers were separated in a separatory funnel The aqueous layer was extracted one more time with 30 mL of ethyl acetate. The product was purified by flash chromatography (1% EtOAc/DCM, Rf 0.44) to give 0.56 g (69% yield) of tert-Butyl 4-(3-(tert-butoxycarbonylamino)-4-(methoxycarbonyl)phenyl)piperazine-1-carboxylate. ¹H-NMR (CDCl₃, 400 MHz): δ 10.48 (1H, s), 8.01 (1H, d, J=2.5 Hz), 7.87 (1H, d, J=9.0 Hz), 6.46 (1H, dd, J1=9.0 Hz, J2=2.5 Hz), 3.86 (3H, s), 3.57 (4H, t, J=5.0 Hz), 3.36 (4H, t, J=5.0 Hz), 1.53 (9H, s), 1.49 (9H, s).

Step 115C

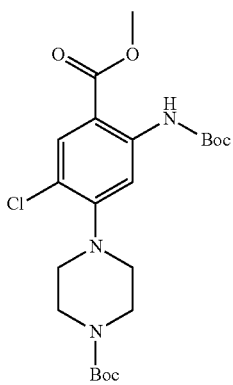 [SMILES: COC(=O)c1cc(Cl)c(N2CCN(C(=O)OC(C)(C)C)CC2)cc1NC(=O)OC(C)(C)C]

To a solution of tert-butyl 4-(3-(tert-butoxycarbonylamino)-4-(methoxycarbonyl)phenyl)piperazine-1-carboxylate (360 mg, 0.827 mmol) in DCM (4 mL) at −78° C. was added TFA (0.064 mL, 0.827 mmol). The reaction mixture was warmed to 0° C., followed by the addition of NCS (110 mg, 0.827 mmol) and MeOH (2.000 mL). The resulted reaction mixture was stirred at RT for 16 hours. The product was purified by flash chromatography (2% EtOAc/DCM, Rf 0.50) to give 150 mg (77% yield) of tert-Butyl 4-(5-(tert-butoxycarbonylamino)-2-chloro-4-(methoxycarbonyl)phenyl)piperazine-1-carboxylate. ¹H-NMR (CDCl₃, 400 MHz): δ 10.31 (1H, s), 8.18 (1H, s), 7.98 (1H, s), 3.90 (3H, s), 3.61 (4H, t, J=4.8 Hz), 3.14 (4H, t, J=4.8 Hz), 1.53 (9H, s), 1.49 (9H, s).

Step 115D

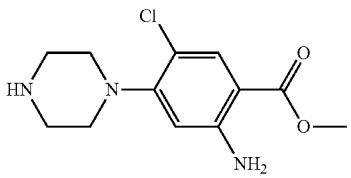 [SMILES: COC(=O)c1cc(Cl)c(N2CCNCC2)cc1N]

A solution of tert-butyl 4-(5-(tert-butoxycarbonylamino)-2-chloro-4-(methoxycarbonyl)phenyl)piperazine-1-carboxylate (130 mg, 0.277 mmol) and TFA (0.4 mL, 5.19 mmol) in DCM (0.4 mL) was stirred at RT for one hour. Solvent was evaporated in vacuo to give 89 mg of methyl 2-amino-5-chloro-4-(piperazin-1-yl)benzoate. HPLC/MS showed MS (ESI+) (m/z) 270 ([M+H]$^+$).

Step 115E

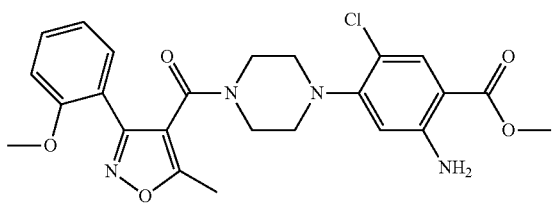

3-(2-Methoxyphenyl)-5-methylisoxazole-4-carboxylic acid and methyl 2-amino-5-chloro-4-(piperazin-1-yl)benzoate (TFA salt) were coupled under the conditions described in Preparation M to give methyl 2-amino-5-chloro-4-(4-(3-(2-methoxyphenyl)-5-methylisoxazole-4-carbonyl)piperazin-1-yl)benzoate. $^1$H-NMR (CDCl$_3$, 400 MHz): δ 7.82 (1H, s), 7.60-7.47 (2H, m), 7.13-6.97 (2H, m), 6.01 (1H, s), 3.85 (3H, s), 3.84 (2H, s), 3.80 (3H, s), 3.25 (2H, s), 2.99 (2H, s), 2.58 (3H, s), 2.42 (2H, s).

Step 115F

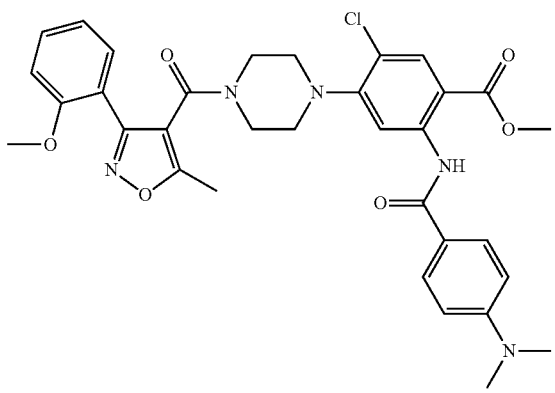

The reaction mixture of methyl 2-amino-5-chloro-4-(4-(3-(2-methoxyphenyl)-5-methylisoxazole-4-carbonyl)piperazin-1-yl)benzoate (27.5 mg, 0.057 mmol), 4-(dimethylamino)benzoyl chloride (52.1 mg, 0.284 mmol), N,N-dimethylpyridin-4-amine (0.693 mg, 5.67 μmol) and 2-tert-Butylimino-2-diethylamino-1,3-dimethyl-perhydro-1,3,2-diazaphosphorine (78 mg, 0.284 mmol) in DCE (1.5 mL) was stirred at 80° C. for 6 hours. The product was purified by preparative HPLC (0.1% TFA MeOH/H$_2$O) to give 25 mg (49% yield) of methyl 5-chloro-2-(4-(dimethylamino)benzamido)-4-(4-(3-(2-methoxyphenyl)-5-methylisoxazole-4-carbonyl)piperazin-1-yl)benzoate. $^1$H-NMR (CDCl$_3$, 400 MHz): δ 12.06 (1H, s), 8.53 (1H, s), 8.05-7.99 (3H, m), 7.59 (1H, dd, J1=7.5 Hz, J2=1.5 Hz), 7.53-7.46 (1H, m), 7.15-6.99 (4H, m), 3.95 (3H, s), 3.84 (2H, s), 3.82 (3H, s), 3.28 (2H, s), 3.15 (6H, s), 2.59 (3H, s).

Step 115G

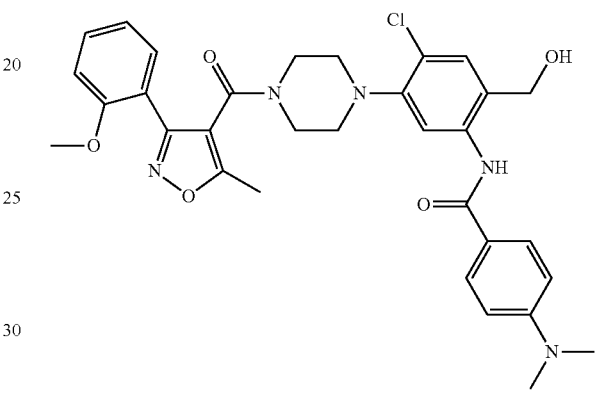

To a solution of methyl 5-chloro-2-(4-(dimethylamino)benzamido)-4-(4-(3-(2-methoxyphenyl)-5-methylisoxazole-4-carbonyl)piperazin-1-yl)benzoate (108 mg, 0.171 mmol) in MeOH (1 mL) and THF (3 mL) at room temperature was added sodium borohydride (32.3 mg, 0.854 mmol). The resulting reaction mixture was stirred at 40° C. for 2 hours. The product was purified by preparative HPLC(CH$_3$CN/H2O-10 nM ammonium acetate) to give 90 mg (81% yield) of N-(4-Chloro-2-(hydroxymethyl)-5-(4-(3-(2-methoxyphenyl)-5-methylisoxazole-4-carbonyl)piperazin-1-yl)phenyl)-4-(dimethylamino)benzamide. $^1$H-NMR (CDCl$_3$, 400 MHz): δ 9.39 (1H, s), 8.03 (1H, s), 7.84 (2H, d, J=8.8 Hz), 7.58 (1H, dd, J1=7.5 Hz, J2=1.8 Hz), 7.52-7.45 (1H, m), 7.14 (1H, s), 7.11-6.99 (2H, m), 6.74 (2H, d, J=9.0 Hz), 4.71 (2H, s), 3.82 (3H, s), 3.77 (2H, s), 3.23 (2H, s), 2.97 (2H, s), 3.07 (6H, s), 2.57 (3H, s), 2.46 (2H, s).

Step 115H

A solution of N-(4-chloro-2-(hydroxymethyl)-5-(4-(3-(2-methoxyphenyl)-5-methylisoxazole-4-carbonyl)piperazin-1-yl)phenyl)-4-(dimethylamino)benzamide (60 mg, 0.099 mmol) in DCM (1.2 mL) was added to PCC (300 mg, 0.278 mmol) in an 8-mL vial. The reaction mixture was stirred at RT for 40 min. PCC on basic alumina was removed by filtration. The crude product was purified by flash chromatography (EtOAc/DCM, 20% gradient to 40%, Rf 0.66) to give 11.0 mg of the title compound. $^1$H-NMR (CDCl$_3$, 400 MHz): δ 12.00 (1H, s), 9.77 (1H, s), 8.58 (1H, s), 7.97 (2H, d, J=9.0 Hz), 7.61-7.56 (2H, m), 7.52-7.45 (1H, m), 7.15-6.99 (2H, m), 6.77 (2H, d, J=9.0 Hz), 3.83 (3H, s), 3.80 (2H, s), 3.26 (2H, s), 3.17 (2H, s), 3.09 (6H, s), 2.59 (3H, s). HPLC/MS (Method H): (ES+) m/z (M+H)$^+$=602; R$_t$=2.07 min.

Example 116

(E)-N-(4-chloro-2-((hydroxyimino)methyl)-5-(4-(3-(2-methoxyphenyl)-5-methylisoxazole-4-carbonyl)piperazin-1-yl)phenyl)-4-(dimethylamino)benzamide

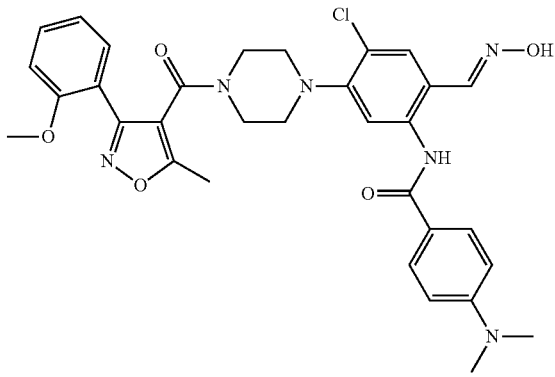 [SMILES: COc1ccccc1-c1noc(C)c1C(=O)N1CCN(c2cc(NC(=O)c3ccc(N(C)C)cc3)c(/C=N/O)cc2Cl)CC1]

The reaction mixture of N-(4-chloro-2-formyl-5-(4-(3-(2-methoxyphenyl)-5-methylisoxazole-4-carbonyl)piperazin-1-yl)phenyl)-4-(dimethylamino)benzamide (Example 115, 7.7 mg, 0.013 mmol), hydroxylamine hydrochloride (1.8 mg, 0.026 mmol) and triethylamine (3.6 µL, 0.026 mmol) in DMF (1.2 mL), MeOH (0.240 mL) and DCM (0.240 mL) was stirred at RT overnight. The product was purified by preparative HPLC (10 mM NH$_4$OAc AcCN/H2O) to give 2.7 mg of the title compound. $^1$H-NMR (DMSO-d$_6$, 400 MHz) δ 11.46 (1H, br. s.), 8.48 (1H, s), 8.31 (1H, s), 7.87 (2H, d, J=9.0 Hz), 7.58 (1H, s), 7.55-7.44 (2H, m), 7.18 (1H, d, J=8.3 Hz), 7.10 (1H, t, J=7.5 Hz), 6.81 (2H, d, J=9.0 Hz), 3.75 (3H, s), 3.03 (6H, s). HPLC/MS (Method H): (ES+) m/z (M+H)$^+$=617; R$_t$=1.98 min.

Example 117

N-(4-chloro-5-(4-(3-(2-hydroxyphenyl)-5-methylisoxazole-4-carbonyl)piperazin-1-yl)-2-nitrophenyl)-4-(dimethylamino)benzamide

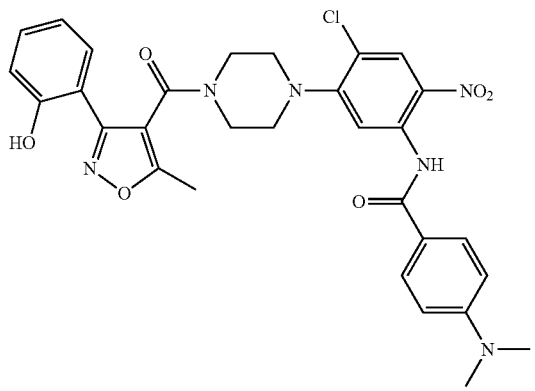 [SMILES: Cc1onc(-c2ccccc2O)c1C(=O)N1CCN(c2cc(NC(=O)c3ccc(N(C)C)cc3)c([N+](=O)[O-])cc2Cl)CC1]

To N-(4-chloro-5-(4-(3-(2-methoxyphenyl)-5-methylisoxazole-4-carbonyl)piperazin-1-yl)-2-nitrophenyl)-4-(dimethylamino)benzamide (Example 14, 50 mg, 0.081 mmol) in 7 mL of DCM at −78° C. was added 0.24 mL of 1.0 M boron tribromide in DCM. The solution was stirred at room temperature for 16 hours. Solvent was evaporated in vacuo and the product was purified by preparative HPLC (acetonitrile/water, 10 mM NH$_4$OAc) to give 42 mg of the title compound. $^1$H-NMR (CDCl$_3$, 400 MHz): δ 11.52 (1H, s), 8.70 (1H, s), 8.30 (1H, s), 7.90 (2H, d, J=9.0 Hz), 7.45-7.33 (2H, m), 7.15-7.07 (1H, m), 7.04-6.95 (1H, m), 6.88 (2H, d, J=8.8 Hz), 4.07-4.00 (2H, m), 3.38 (4H, s), 3.12 (6H, s), 2.99 (2H, s), 2.57 (3H, s). HPLC/MS (Method G): (ES+) m/z (M+H)$^+$=605; R$_t$=2.29 min.

Example 118

N-(4-chloro-5-(4-(3-(2-ethoxyphenyl)-5-methylisoxazole-4-carbonyl)piperazin-1-yl)-2-nitrophenyl)-4-(dimethylamino)benzamide

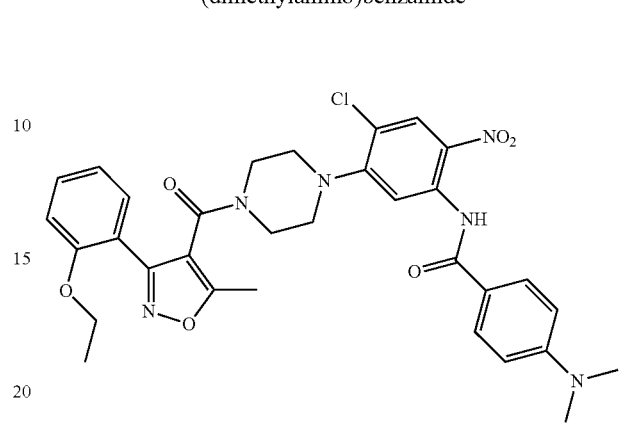

To the solution of N-(4-chloro-5-(4-(3-(2-hydroxyphenyl)-5-methylisoxazole-4-carbonyl)piperazin-1-yl)-2-nitrophenyl)-4-(dimethylamino)benzamide (Example 117, 17 mg, 0.028 mmol), ethanol (2.461 µL, 0.042 mmol) and tri-n-butyl phosphine (10.40 µL, 0.042 mmol) in THF (2 mL) at 0° C. was added DIAD (8.19 µL, 0.042 mmol). The reaction mixture was stirred at 0° C. for 3 min. and at RT overnight.

The solvent was evaporated in vacuo. The product was purified by preparative HPLC (0.1% TFA, MeOH/H$_2$O) to give 6 mg of the title compound. $^1$H-NMR (CDCl$_3$, 400 MHz): δ 11.48 (1H, s), 8.61 (1H, s), 8.27 (1H, s), 7.90 (2H, d, J=9.0 Hz), 7.58-7.43 (2H, m), 7.14-6.98 (2H, m), 6.78 (2H, d, J=9.0 Hz), 3.79 (2H, s), 3.25-3.12 (4H, m), 3.10 (6H, s), 2.60 (3H, s), 2.47 (2H, s). HPLC/MS (Method B): (ES+) m/z (M+H)$^+$=633; R$_t$=2.94 min.

Example 119

N-(5-(4-(3-(2-butoxyphenyl)-5-methylisoxazole-4-carbonyl)piperazin-1-yl)-4-chloro-2-nitrophenyl)-4-(dimethylamino)benzamide

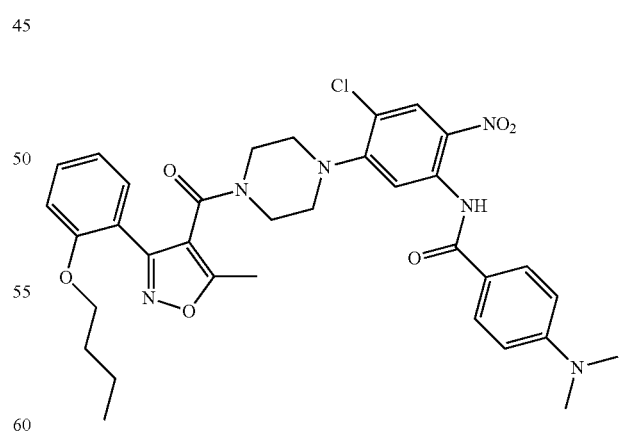

The title compound was synthesized by analogy to Example 118, substituting n-butanol for ethanol. HPLC/MS (Method B): (ES+) m/z (M+H)$^+$=647; R$_t$=3.14 min. J=9.0 Hz), 3.79 (2H, s), 3.25-3.12 (4H, m), 3.10 (6H, s), 2.60 (3H, s), 2.47 (2H, s). HPLC/MS (Method B): (ES+) m/z (M+H)$^+$=633; R$_t$=2.94 min.

Example 120

N-(4-chloro-5-(4-(4-(2-methoxyphenyl)-1-methyl-1H-1,2,3-triazole-5-carbonyl)piperazin-1-yl)-2-bromophenyl)-4-(1,1-dioxidoisothiazolidin-2-yl)benzamide

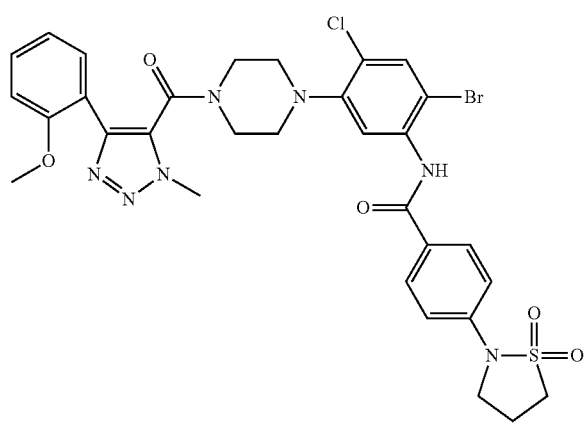 [SMILES: COc1ccccc1-c1nnn(C)c1C(=O)N1CCN(c2cc(NC(=O)c3ccc(N4CCCS4(=O)=O)cc3)c(Br)cc2Cl)CC1]

Step 120A

N-(4-chloro-2-bromo-5-(piperazin-1-yl)phenyl)-4-(1,1-dioxidoisothiazolidin-2-yl)benzamide

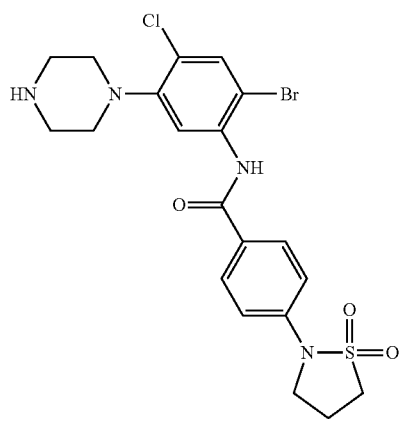 [SMILES: O=C(Nc1cc(N2CCNCC2)c(Cl)cc1Br)c1ccc(N2CCCS2(=O)=O)cc1]

N-(4-chloro-2-bromo-5-(piperazin-1-yl)phenyl)-4-(1,1-dioxidoisothiazolidin-2-yl)benzamide was prepared by analogy to Preparation O, substituting Preparation AI for the product from Step O1 and Preparation W for 4-(N,N-dimethylamino)benzoyl chloride.

Step 120B

The title compound was prepared by analogy to Example 70, substituting Preparation J for Preparation D. HPLC/MS (Method J): (ES+) m/z (M+Na)$^+$=730; R$_t$=1.75 min.

Example 121

N-(2-bromo-4-chloro-5-(4-(4-(2-methoxyphenyl)-1-methyl-1H-1,2,3-triazole-5-carbonyl)piperazin-1-yl)phenyl)-4-(1H-1,2,4-triazol-1-yl)benzamide

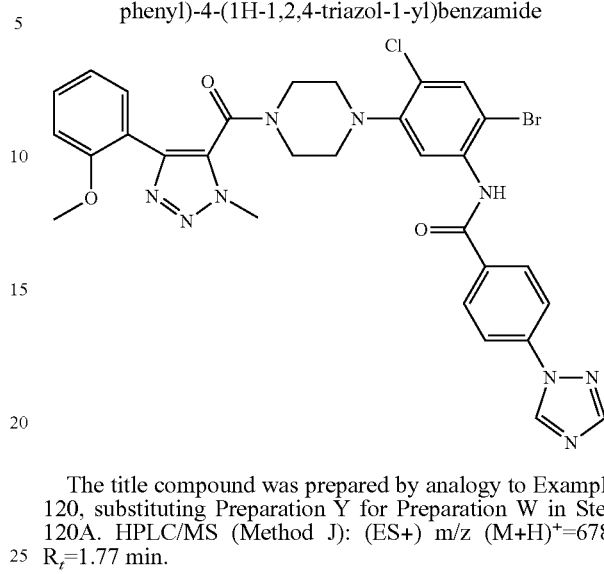

The title compound was prepared by analogy to Example 120, substituting Preparation Y for Preparation W in Step 120A. HPLC/MS (Method J): (ES+) m/z (M+H)$^+$=678; R$_t$=1.77 min.

Example 122

N-(4-cyano-5-(4-(4-(2-methoxyphenyl)-1-methyl-1H-1,2,3-triazole-5-carbonyl)piperazin-1-yl)-2-nitrophenyl)-4-(2-oxopyrrolidin-1-yl)benzamide

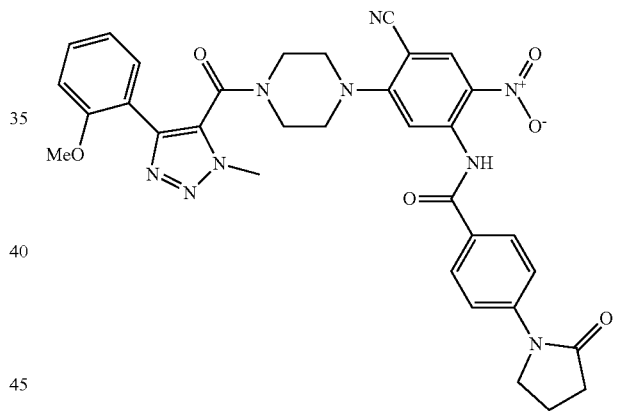

Step 122A

N-(4-cyano-2-nitro-5-(piperazin-1-yl)phenyl)-4-(2-oxopyrrolidin-1-yl)benzamide

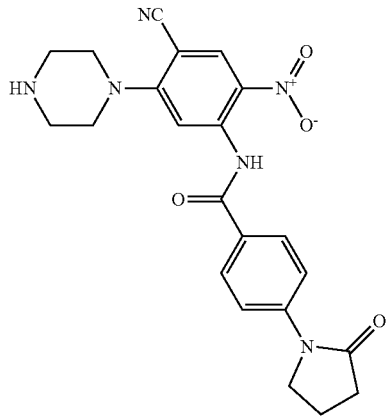 [SMILES: N#Cc1cc([N+](=O)[O-])c(NC(=O)c2ccc(N3CCCC3=O)cc2)cc1N1CCNCC1]

N-(4-cyano-2-nitro-5-(piperazin-1-yl)phenyl)-4-(2-oxopyrrolidin-1-yl)benzamide was prepared by analogy to Preparation O, substituting the product from Step AG2 of Preparation AG for the product from Step O1 and Preparation AB for N,N-dimethylbenzoyl chloride.

Step 122B

The title compound was prepared by analogy to Example 70, substituting Preparation J for Preparation D. HPLC/MS (Method F): (ES+) m/z (M+H)$^+$=651; $R_t$=2.93 min.

Examples 123-124

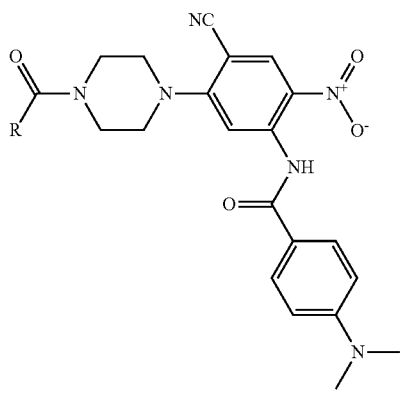

Examples 123-124 were Prepared by Analogy to Example 122, Substituting 4-(N,N-dimethylamino)benzoyl chloride for Preparation AB and the Appropriate Heterocycle Preparation for Preparation J

| Example | R | Heterocycle Preparation | MH+ | RT | LC/MS Method |
|---|---|---|---|---|---|
| 123 | (2-methoxyphenyl-methylpyrazole) | D | 609 | 3.12 | F |
| 124 | (2-methoxyphenyl-imidazole) | H | 609 | 2.68 | F |

Example 125

N-(4-chloro-5-(4-(3-(2-methoxyphenyl)-5-methyl-isoxazole-4-carbonyl)piperazin-1-yl)-2-vinylphenyl)-4-(dimethylamino)benzamide

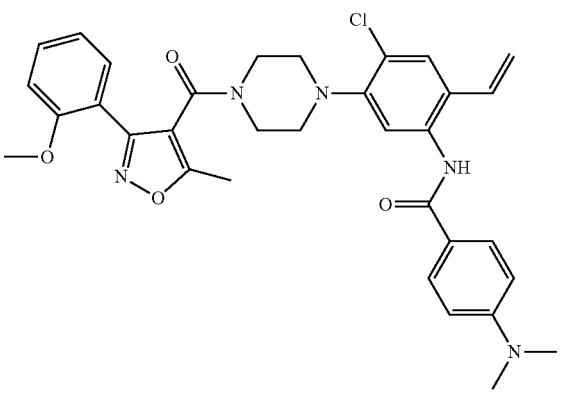

The title compound was synthesized by analogy to Example 1, substituting Preparation S for Preparation O and 4-(N,N-dimethylamino)benzoyl chloride for 4-methoxybenzoyl chloride. HPLC/MS (Method H): (ES+) m/z (M+H)$^+$=600; $R_t$=1.88 min.

Example 126

N-(4-chloro-5-(4-(3-(2-chlorophenyl)-5-methyl-1H-pyrazole-4-carbonyl)piperazin-1-yl)-2-nitrophenyl)-4-(methylsulfonamido)benzamide

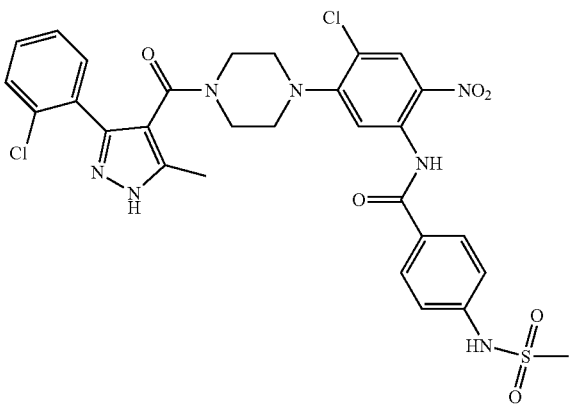 [SMILES: Cc1[nH]nc(-c2ccccc2Cl)c1C(=O)N1CCN(c2cc(NC(=O)c3ccc(NS(C)(=O)=O)cc3)c([N+](=O)[O-])cc2Cl)CC1]

The title compound was prepared by analogy to Example 70, substituting Preparation AH for Preparation O and Preparation E for Preparation D. HPLC/MS (Method H): (ES+) m/z (M+H)$^+$=670; $R_t$=1.76 min.

Example 127

N-(4-chloro-5-(4-(4-(2-methoxyphenyl)-1-methyl-1H-1,2,3-triazole-5-carbonyl)piperazin-1-yl)-2-nitrophenyl)-4-(methylsulfonamido)benzamide

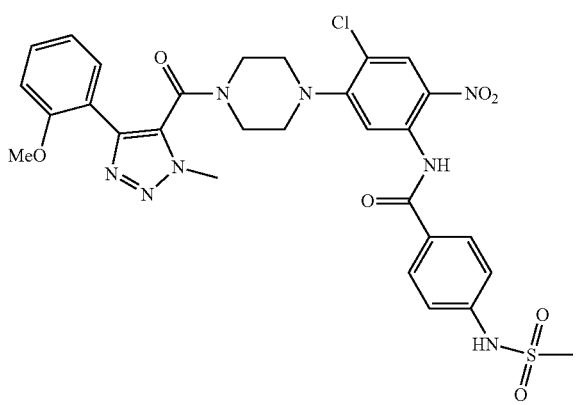 [SMILES: COc1ccccc1-c1nnn(C)c1C(=O)N1CCN(c2cc(NC(=O)c3ccc(NS(C)(=O)=O)cc3)c([N+](=O)[O-])cc2Cl)CC1]

The title compound was prepared by analogy to Example 126, substituting Preparation J for Preparation E. HPLC/MS (Method H): (ES+) m/z (M+H)$^+$=669; R$_f$=1.82 min.

Example 128

N-(4-chloro-5-(4-(4-(2-methoxyphenyl)-1-methyl-1H-1,2,3-triazole-5-carbonyl)piperazin-1-yl)-2-nitrophenyl)thiazole-2-carboxamide

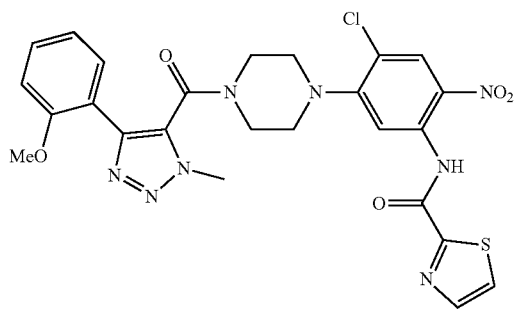 [SMILES: COc1ccccc1-c1nnn(C)c1C(=O)N1CCN(c2cc(NC(=O)c3nccs3)c([N+](=O)[O-])cc2Cl)CC1]

The title compound was prepared by analogy to Example 84, substituting thiazole-2-carbonyl chloride for Preparation AB in Step 84A. HPLC/MS (Method J): (ES+) m/z (M+H)$^+$= 583; R$_f$=1.91 min.

Materials and Methods

Cells and Virus

Madin Darby canine kidney (MDCK) cells and influenza A/WSN/33 were obtained from ATCC. Influenza A/Solomon Islands/3/06 and influenza A/Brisbane/10/2007 were obtained from the CDC.

Compounds

Test compounds, at 100× the final test concentration, were serially diluted in DMSO in 3-fold steps. One ul of diluted compound was added to each well of a 96-well plate.

Antiviral Assays

For antiviral assays, MDCK cells were re-suspended in assay media (MEM with pen/strep plus 0.125% BA (bovine albumin) and 1 ug/ml TPCK-treated trypsin) at 4.5×10$^5$ cells per ml. Virus was added for final multiplicity of infection (MOI) of 0.001 plaque forming units per cell and 100 ul was added to each well of a 96-well plate (1 ul of compound/well). For cytotoxicity assays, only cells were added to the assay plates. 48 hrs post infection, viral replication in the presence of inhibitor was determined by measuring viral neuraminidase (NA) activity via activation of the quenched substrate 2'-(4-Methylunbelliferyl)-α-D-N-acetylneuraminic acid (MUNANA). A 5× substrate solution was added to yield a final concentration of 100 uM MUNANA, 50 mM MES, 2 mM CaCl$_2$ and 0.25% NP-40. After a 30 minute incubation at 37° C. the plates were read on a fluorescence plate reader set at 360 nm excitation and 460 nm emission. Cytotoxicity was ascertained via crystal violet staining of treated cells. Cells were washed once with PBS, stained for 20 min with 0.5% crystal violet in 20% methanol, washed with water and air dried. 50 ul of methanol was added to each well to solubilize the crystal violet and 50 ul PBS was added before the absorbance was read at 540 nM.

REFERENCES

Chen J, Deng Y M. 2009. Influenza virus antigenic variation, host antibody production and new approach to control epidemic. Virol J. March 13; 6:30.

Deyde V M, Sheu T G, Trujillo A A, Okomo-Adhiambo M, Garten R, Klimov A I, Gubareva L V. 2010. Detection of molecular markers of drug resistance in 2009 pandemic influenza A (H1N1) viruses by pyrosequencing. Antimicrob Agents Chemother. March; 54(3):1102-10.

Moscona A. 2009. Global transmission of oseltamivir-resistant influenza. N Engl J. Med. March 5; 360(10):953-6.

Soepandi P Z, Burhan E, Mangunnegoro H, Nawas A, Aditama T Y, Partakusuma L, Isbaniah F, Malik S, Benamore R, Baird J K, Taylor W R. 2010. Clinical course of H5N1 avian influenza in patients at the Persahabatan Hospital, Jakarta, Indonesia, 2005-2008. Chest 09-2644.

Zimmer S M, Burke D S. 2009. Historical perspective—Emergence of influenza A (H1N1) viruses. N Engl J. Med. July 16; 361(3):279-85.

| | Activity Table 1 | | |
|---|---|---|---|
| Example | A/H1N1/WSN Activity | A/H1N1/ Solomon Islands Activity | A/H3N2/ Brisbane Activity |
| 1 | +++ | +++ | ++ |
| 5 | +++ | +++ | ++ |
| 9 | +++ | ++ | + |
| 14 | +++ | +++ | +++ |
| 24 | +++ | +++ | + |
| 35 | +++ | +++ | ++ |
| 37 | +++ | +++ | ++ |
| 38 | ++ | ++ | +++ |
| 43 | ++ | ++ | +++ |
| 47 | +++ | +++ | ++ |
| 52 | ++ | ++ | + |
| 54 | ++ | ++ | + |
| 55 | +++ | +++ | ++ |
| 56 | ++ | + | + |
| 65 | +++ | ++ | + |
| 66 | + | + | + |
| 68 | ++ | +++ | +++ |
| 69 | ++ | ++ | + |
| 70 | +++ | ++ | + |
| 72 | +++ | +++ | ++ |
| 73 | ++ | +++ | ++ |
| 81 | +++ | +++ | + |
| 84 | +++ | +++ | +++ |

-continued

Activity Table 1

| Example | A/H1N1/WSN Activity | A/H1N1/ Solomon Islands Activity | A/H3N2/ Brisbane Activity |
|---|---|---|---|
| 92 | +++ | +++ | ++ |
| 93 | +++ | +++ | ++ |
| 102 | +++ | ++ | + |
| 120 | ++ | ++ | + |
| 122 | ++ | ++ | ++ |
| 124 | +++ | +++ | +++ |
| 125 wherein

L is H, halogen, cyano, hydroxyl, amino, alkyl, alkoxy, alkylamino, or amido;

M is H, halogen, cyano, hydroxyl, amino, alkyl, alkoxy, alkylamino, or amido;

Q is H, halogen, cyano, hydroxyl, amino, alkyl, alkoxy, alkylamino, or amido;

U is H, halogen, cyano, hydroxyl, amino, alkyl, alkoxy, alkylamino, or amido;

$X_1$ is O, NH, N-alkyl, N-aryl, S or $CH_2$; and $Y_1$ is O, NH, N-alkyl, N-aryl, S or $CH_2$.

5. The compound of claim 4, wherein Ar is

6. The compound of claim 5, wherein said Ar is substituted with methoxy or hydroxyl.

7. The compound of claim 1, wherein W is —$NO_2$, —Cl, —Br, or —CN.

8. The compound of claim 1, wherein X is —Cl or —CN.

9. The compound of claim 1, wherein Y is —CH or —N and Ar is phenyl substituted with methoxy or hydroxyl.

10. The compound of claim 1, wherein Z is substituted aryl or substituted heteroaryl which is selected from the group of:

-continued

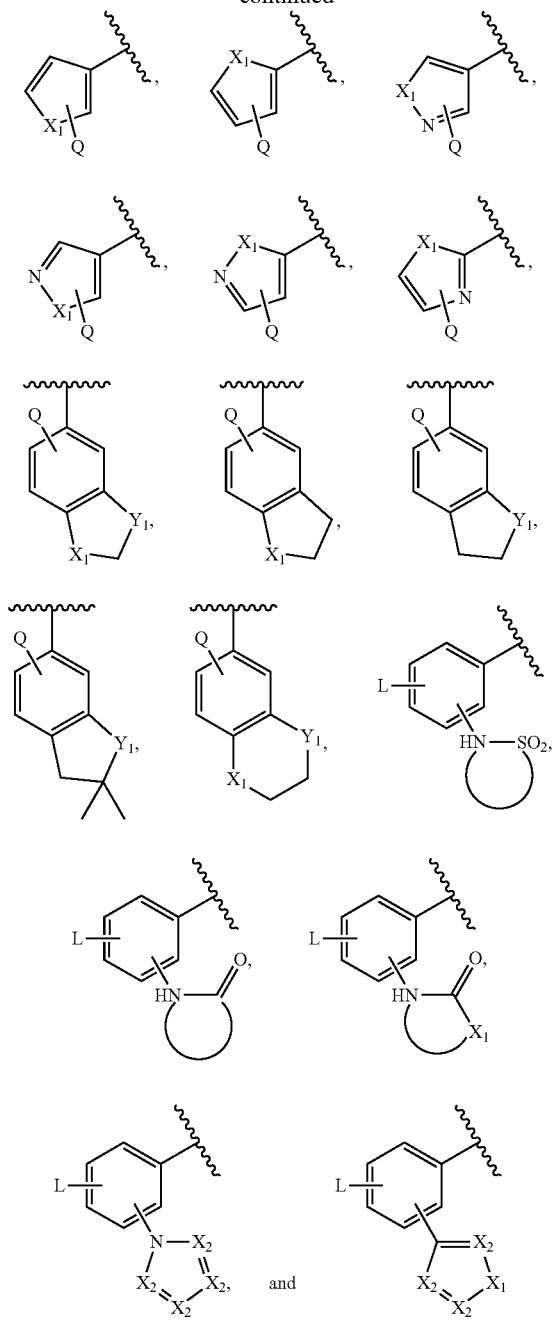

wherein

L is H, halogen, cyano, hydroxyl, amino, alkyl, alkoxy, alkylamino, or amido;

M is H, halogen, cyano, hydroxyl, amino, alkyl, alkoxy, alkylamino, or amido;

Q is H, halogen, cyano, hydroxyl, amino, alkyl, alkoxy, alkylamino, or amido;

U is H, halogen, cyano, hydroxyl, amino, alkyl, alkoxy, alkylamino, or amido;

$X_1$ is O, NH, N-alkyl, N-aryl, S or $CH_2$;

$X_2$ is N or CH; and $Y_1$ is O, NH, N-alkyl, N-aryl, S or $CH_2$.

11. The compound of claim 10, wherein Z is selected from

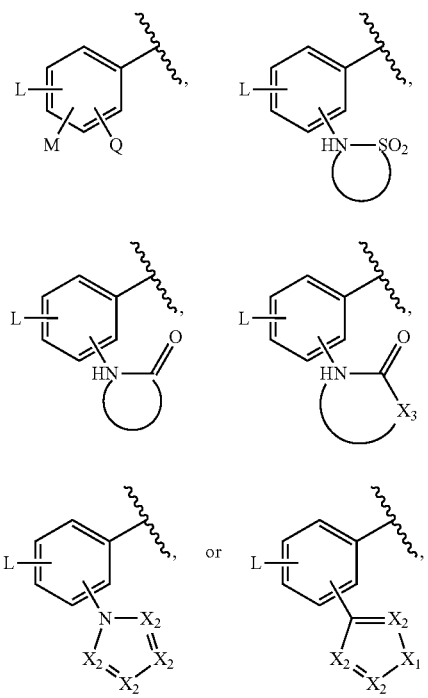

12. The compound of claim 11, wherein said Z is substituted with cyano, amino, alkylamino, or amido.

13. The compound of claim 1, wherein R is —$CH_3$ or —$CH_2F$.

14. The compound of claim 2, wherein Het is selected from the group of:

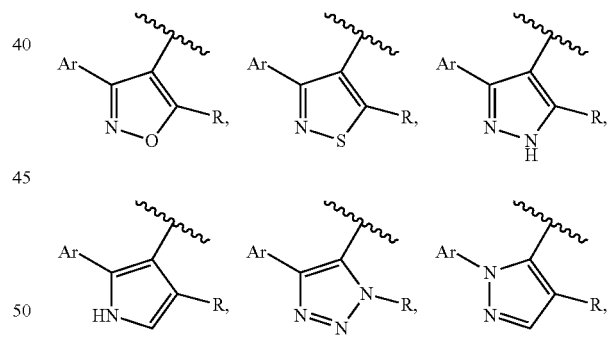

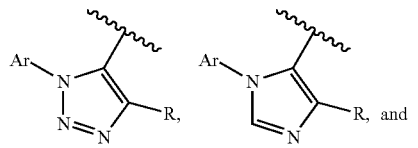

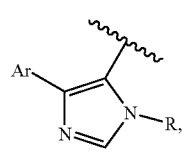

15. The compound of claim 4, wherein Ar is selected from the group of:

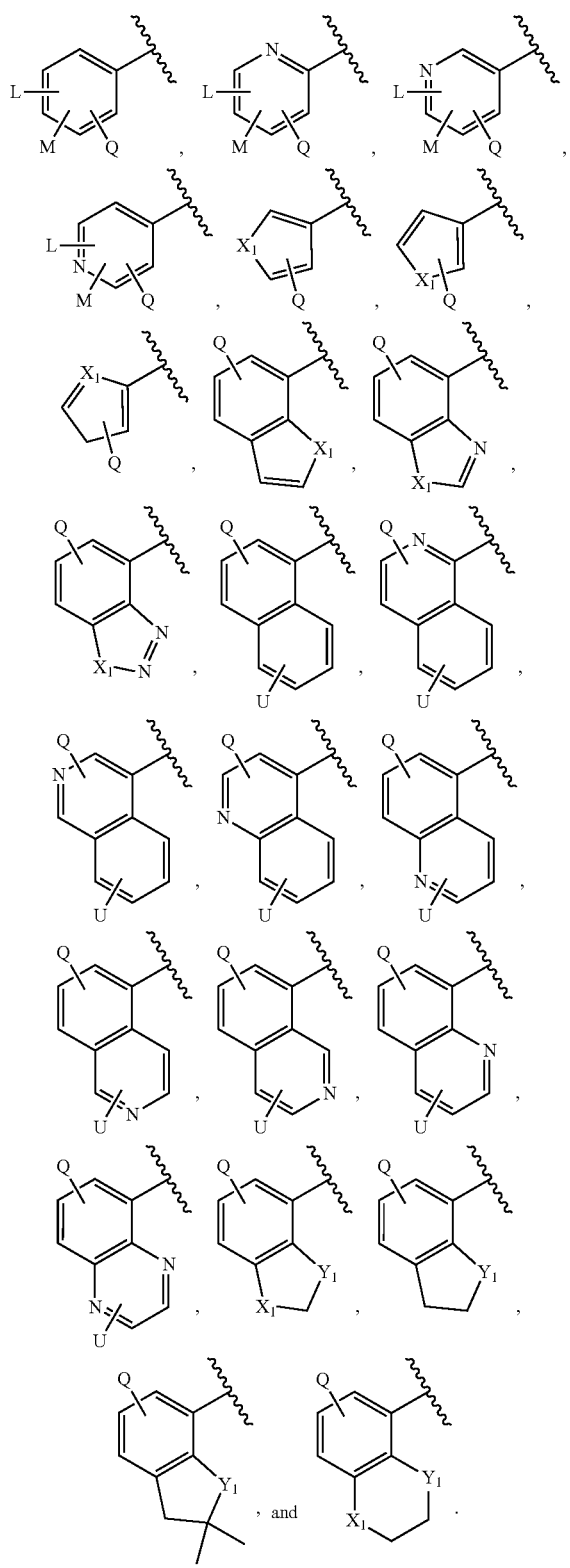
16. The compound of claim 7, wherein W is —NO$_2$, —Cl, or —Br.
17. The compound of claim 8, wherein X is —Cl.
18. The compound of claim 9, wherein Y is —CH or N.
19. The compound of claim 13, wherein R is —CH$_3$.
20. The compound of claim 14, wherein Het is selected from the group of:
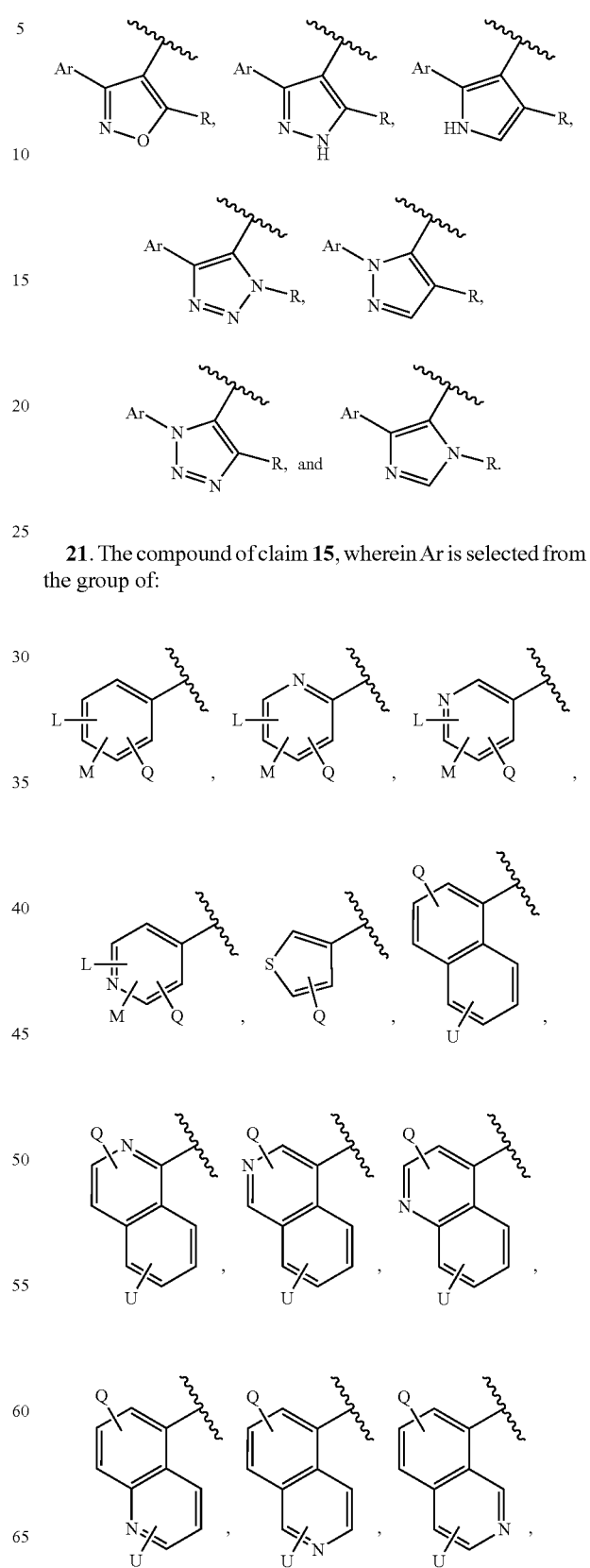
21. The compound of claim 15, wherein Ar is selected from the group of:

-continued
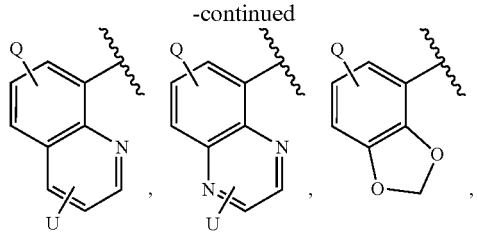
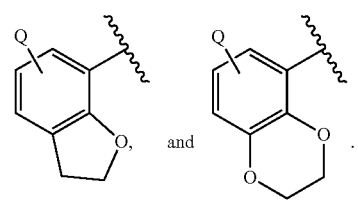
and
22. The compound of claim 21, wherein Ar is
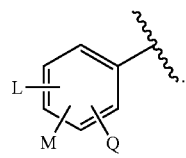
23. The compound of claim 22, wherein said Ar is substituted with methoxy or hydroxyl.
24. The compound of claim 16, wherein W is —NO₂ or —Br.
25. The compound of claim 18, wherein Y is —CH.
26. A compound which is selected from the group consisting of:
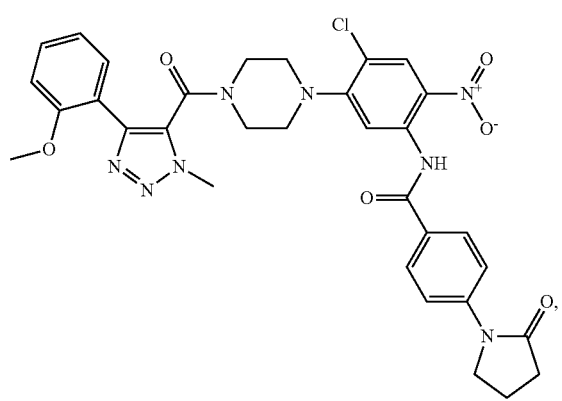
-continued
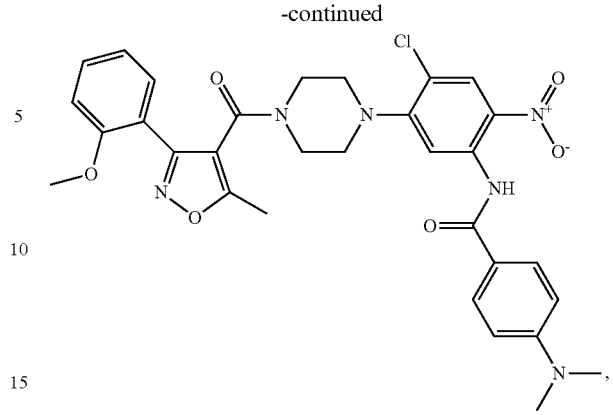
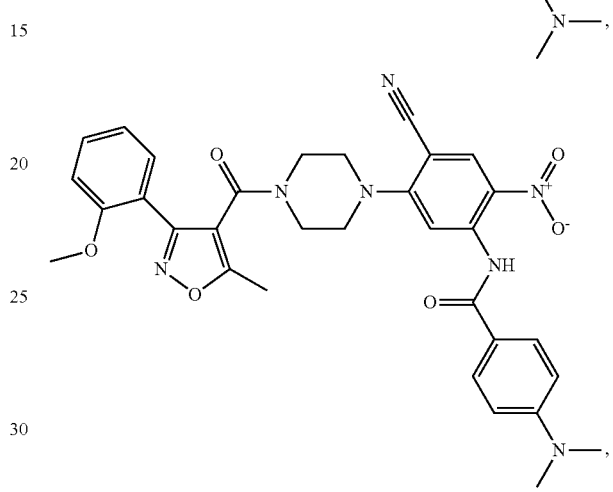
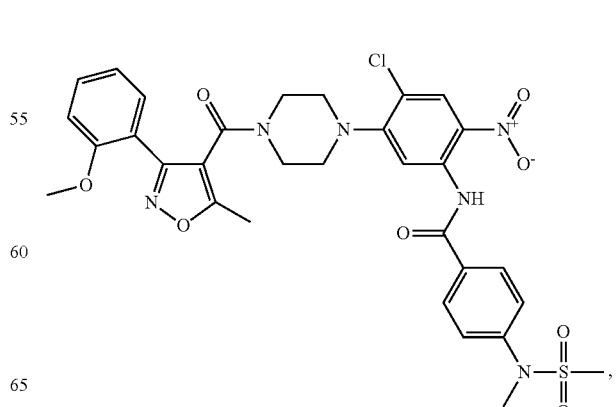

111
-continued
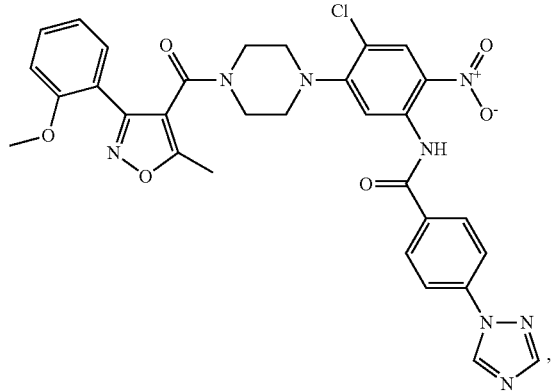
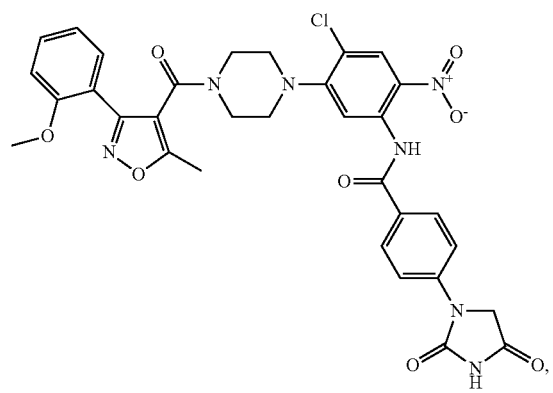
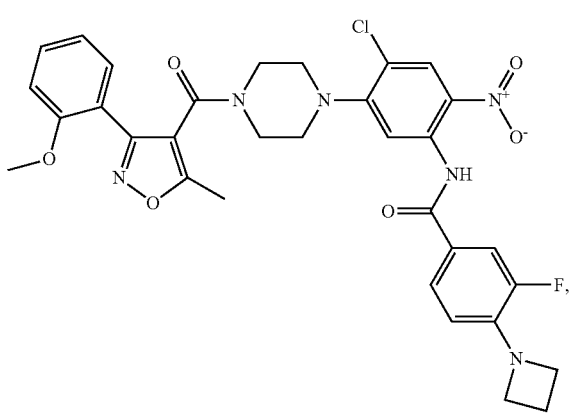
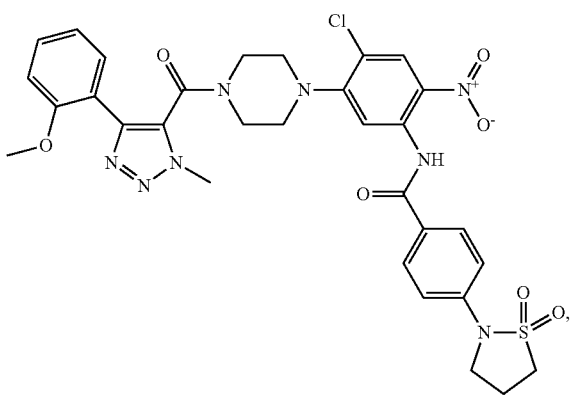
112
-continued
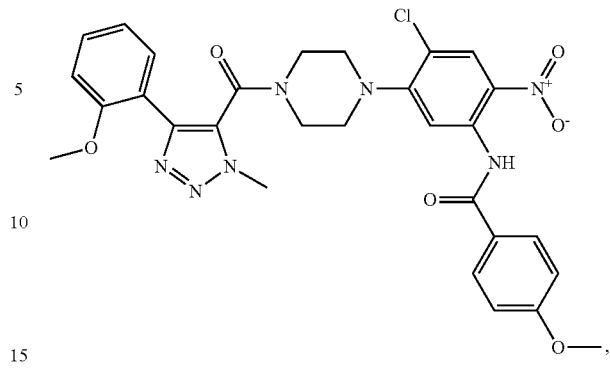
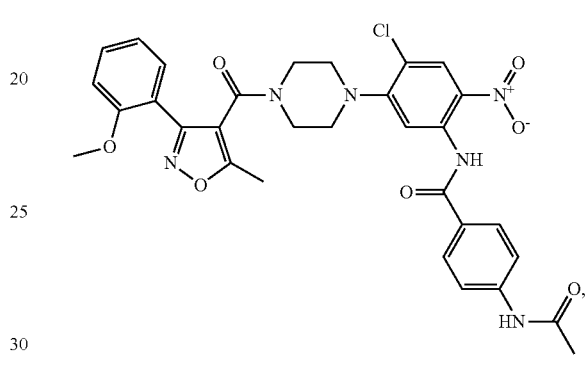
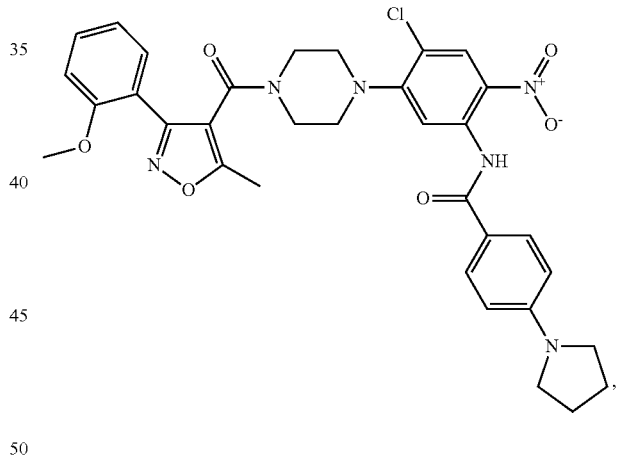
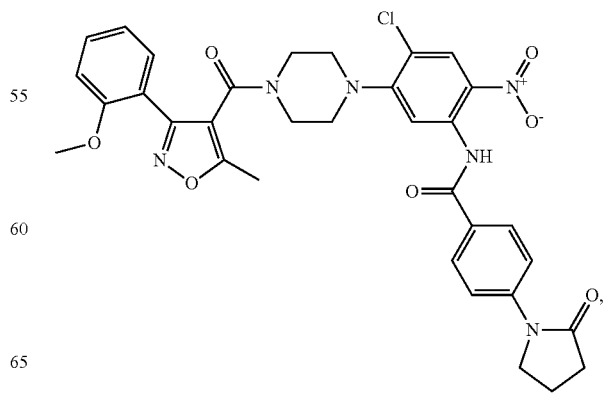

113
-continued

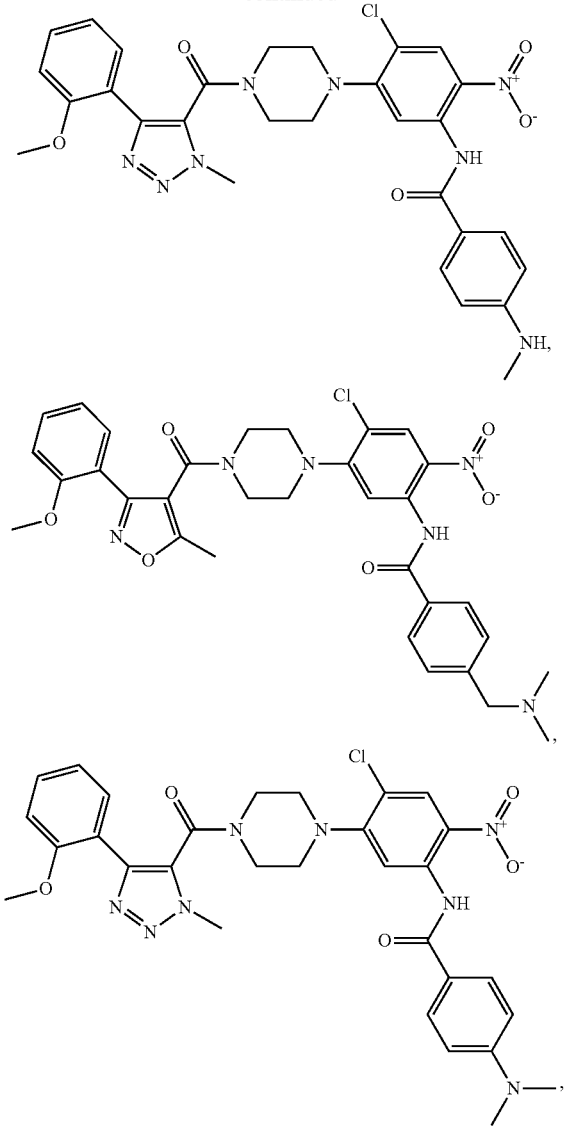

114
-continued

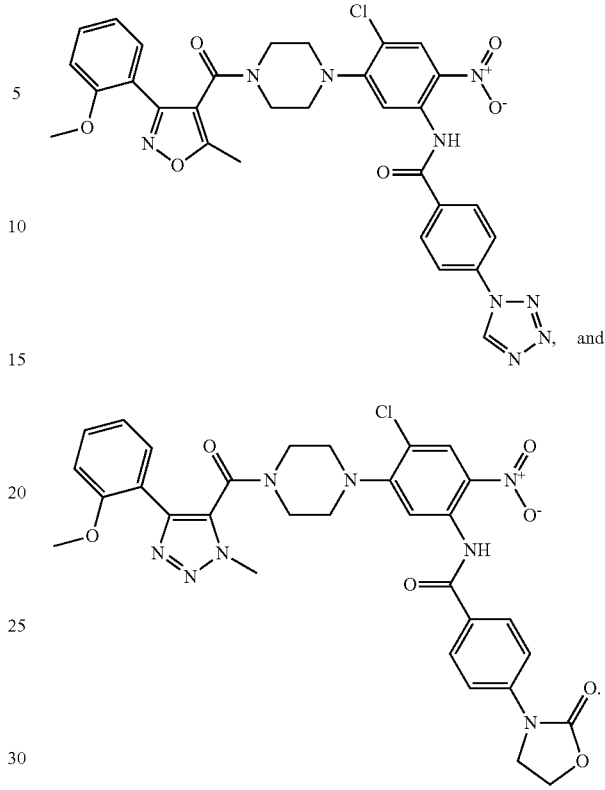

27. A pharmaceutical composition which comprises an antiviral effective amount of one or more of the compounds of Formula I as claimed in claim 1, together with one or more pharmaceutically acceptable carriers, excipients or diluents.

28. A method for treating influenza virus in a mammal infected with influenza virus comprising administering to said mammal an antiviral effective amount of a compound of Formula I as claimed in claim 1, and one or more pharmaceutically acceptable carriers, excipients or diluents.

* * * * *